United States Patent
Wei et al.

(10) Patent No.: US 6,670,162 B2
(45) Date of Patent: Dec. 30, 2003

(54) ISOLATED HUMAN KINASE PROTEINS, NUCLEIC ACID MOLECULES ENCODING HUMAN KINASE PROTEINS, AND USES THEREOF

(75) Inventors: Ming-Hui Wei, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/135,689

(22) Filed: May 1, 2002

(65) Prior Publication Data

US 2002/0123121 A1 Sep. 5, 2002

Related U.S. Application Data

(62) Division of application No. 09/729,995, filed on Dec. 6, 2000, now Pat. No. 6,426,206.
(60) Provisional application No. 60/247,031, filed on Nov. 13, 2000.
(51) Int. Cl.[7] ............................. C12N 9/12; C12N 1/12; C12N 15/00; C07K 1/00; C12Q 1/68
(52) U.S. Cl. ................. 435/194; 435/252.3; 435/320.1; 435/325; 435/6; 530/350
(58) Field of Search ............................. 435/194, 320.1, 435/252.3, 6, 325; 530/350

(56) References Cited

PUBLICATIONS

Tokumitsu H et al. "Characterization of a CA2+/Calmodulin–Dependent Protein Kinase Cascade." Journal of Biological Chemistry, American Society of Biological Chemists, Baltimore, MD, US. vol. 270, No. 33, pp. 19320–19324. Aug. 18, 1995. XP002910043.

Okuno S et al. "Evidence for the Existence of CA2+/Calmodulin–Dependent Protein Kinase IV Kinase Isoforms in Rat Brain." Journal of Biological Chemistry, American Society of Biological Chemists, Baltimore, MD, US. vol. 119, 1996, pp. 1176–1181. XP002910042.

Lawson N et al. "Modulation of a Calcium/Calmoduli–dependent Protein Kinase Cascade by Retinoic Acid During Neutrophil Maturation." Experimental Hematology. vol. 27, 1999, pp. 1682–1690. XP002220530.

International Search Report dated Nov. 28, 2002.

Primary Examiner—Maryam Monshipouri
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

8 Claims, 24 Drawing Sheets

```
   1 CGCCCGCGGG CTGAGCTCGG CGATCTGGGC CCCAGCGAGG CGGTGGGGCG
  51 GGGCGGGGCG GGGCGGGGCG CGCAGCAGGA GCGAGTGGGG CCGCCCGCCG
 101 GGCCACGGAC ACTGTCGCCC GGCGCCCAGG TTCCCAACAA GGCTACGCAG
 151 AAGAACCCCC TTGACTGAAG CAATGGAGGG GGGTCCAGCT GTCTGCTGCC
 201 AGGATCCTCG GGCAGAGCTG GTAGAACGGG TGGCAGCCAT CGATGTGACT
 251 CACTTGGAGG AGGCAGATGG TGGCCCAGAG CCTACTAGAA ACGGTGTGGA
 301 CCCCCCACCA CGGGCCAGAG CTGCCTCTGT GATCCCTGGC AGTACTTCAA
 351 GACTGCTCCC AGCCCGGCCT AGCCTCTCAG CCAGGAAGCT TTCCCTACAG
 401 GAGCGGCCAG CAGGAAGCTA TCTGGAGGCG CAGGCTGGGC CTTATGCCAC
 451 GGGGCCTGCC AGCCACATCT CCCCCCGGGC CTGGCGGAGG CCCACCATCG
 501 AGTCCCACCA CGTGGCCATC TCAGATGCAG AGGACTGCGT GCAGCTGAAC
 551 CAGTACAAGC TGCAGAGTGA GATTGGCAAG GGTGCCTACG TGTGGTGAG
 601 GCTGGCCTAC AACGAAAGTG AAGACAGACA CTATGCAATG AAAGTCCTTT
 651 CCAAAAAGAA GTTACTGAAG CAGTATGGCT TTCCACGTCG CCCTCCCCCG
 701 AGAGGGTCCC AGGCTGCCCA GGGAGGACCA GCCAAGCAGC TGCTGCCCCT
 751 GGAGCGGGTG TACCAGGAGA TTGCCATCCT GAAGAAGCTG GACCACGTGA
 801 ATGTGGTCAA ACTGATCGAG GTCCTGGATG ACCCAGCTGA GGACAACCTC
 851 TATTTGGTGT TTGACCTCCT GAGAAAGGGG CCCGTCATGG AAGTGCCCTG
 901 TGACAAGCCC TTCTCGGAGG AGCAAGCTCG CCTCTACCTG CGGGACGTCA
 951 TCCTGGGCCT CGAGTACTTG CACTGCCAGA AGATCGTCCA CAGGGACATC
1001 AAGCCATCCA ACCTGCTCCT GGGGGATGAT GGGCACGTGA AGATCGCCGA
1051 CTTTGGCGTC AGCAACCAGT TTGAGGGGAA CGACGCTCAG CTGTCCAGCA
1101 CGGCGGGAAC CCCAGCATTC ATGGCCCCCG AGGCCATTTC TGATTCCGGC
1151 CAGAGCTTCA GTGGGAAGGC CTTGGATGTA TGGGCCACTG GCGTCACGTT
1201 GTACTGCTTT GTCTATGGGA AGTGCCCATT CATCGACGAT TTCATCCTGG
1251 CCCTCCACAG GAAGATCAAG AATGAGCCCG TGGTGTTTCC TGAGGAGCCA
1301 GAAATCAGCG AGGAGCTCAA GGACCTGATC CTGAAGATGT TAGACAAGAA
1351 TCCCGAGACG AGAATTGGGG TGCCAGACAT CAAGTTGCAC CCTTGGGTGA
1401 CCAAGAACGG GGAGGAGCCC CTTCCTTCGG AGGAGGAGCA CTGCAGCGTG
1451 GTGGAGGTGA CAGAGGGGGA GGTTAAGAAC TCAGTCAGGC TCATCCCCAG
1501 CTGGACCACG GTGATCCTGG TGAAGTCCAT GCTGAGGAAG CGTTCCTTTG
1551 GGAACCCGTT TGAGCCCCAG GCACGGAGGG AAGAGCGATC CATGTCTGCT
1601 CCAGGAAACC TACTGGTGAA AGAAGGGTTT GGTGAAGGGG GCAAGAGCCC
1651 AGAGCTCCCC GGCGTCCAGG AAGACGAGGC TGCATCCTGA GCCCCTGCAT
1701 GCACCCAGGG CCACCCGGCA GCACACTCAT CCCGCGCCTC CAGAGGCCCA
1751 CCCCTCATGC AACAGCCGCC CCCGCAGGCA GGGGCTGGG GACTGCAGCC
1801 CCACTCCCGC CCCTCCCCCA TCGTGCTGCA TGACCTCCAC GCACGCACGT
1851 CCAGGGACAG ACTGGAATGT ATGTCATTTG GGGTCTTGGG GGCAGGGCTC
1901 CCACGAGGCC ATCCTCCTCT TCTTGGCCCT CCTTGGCCTG ACCCATTCTG
1951 TGGGGAAACC GGGTGCCCAT GGAGCCTCAG AAATGCCACC CGGCTGGTTG
2001 GCATGGCCTG GGGCAGGAGG CAGAGGCAGG AGACCAAGAT GGCAGGTGGA
2051 GGCCAGGCTT ACCACAACGG AAGAGACCTC CCGCTGGGGC CGGGCAGGCC
2101 TGGCTCAGCT GCCACAGGCA TATGGTGGAG AGGGGGGTAC CCTGCCCACC
2151 TTGGGGTGGT GGCACCAGAG CTCTTGTCTA TTCAGACGCT (SEQ ID NO:1)
```

FEATURES:
5'UTR:       1 - 172
Start Codon: 173
Stop Codon:  1688
3'UTR:       1691

FIGURE 1A

Homologous proteins:
Top BLAST Hits

```
                                                               Score    E
gi|1836161|gb|AAB46910.1|  (S83194) Ca2+/calmodulin-dependent pr...  965  0.0
gi|2143629|pir||A57156 Ca2+/calmodulin-dependent protein kinase...   959  0.0
gi|9256525|ref|NP_061371.1| calcium calmodulin dependent protei...   946  0.0
gi|3882295|dbj|BAA34507.1| (AB018330) KIAA0787 protein [Homo sa...   594  e-169
gi|4877951|gb|AAD31507.1|AF140507_1 (AF140507) Ca2+/calmodulin-...    584  e-166
gi|7446417|pir||JC5669 Ca2+/calmodulin-dependent protein kinase...   581  e-165
gi|5729895|ref|NP_006540.1| calcium/calmodulin-dependent protei...   577  e-163
gi|7446362|pir||T37317 probable Ca2+/calmodulin-dependent prote...   409  e-113
gi|7289880|gb|AAF45480.1| (AE002612) CG17698 gene product [Dros...   343  3e-93
gi|3859986|gb|AAC72943.1| (AF091074) unknown [Homo sapiens]          249  7e-65
gi|1711543|sp|P50526|SSP1_SCHPO SERINE/THREONINE-PROTEIN KINASE...   231  2e-59
gi|5053103|gb|AAD38851.1|AF156028_1 (AF156028) calcium/calmodul...    203  4e-51
gi|6320976|ref|NP_011055.1| DNA polymerase alpha suppressing pr...   199  7e-50
gi|6911862|emb|CAB72162.1| (AL138649) serine/threonine-protein ...    193  3e-48
gi|6321259|ref|NP_011336.1| Ygl179cp >gi|1170647|sp|P43637|KGS9...   188  1e-46
```

BLAST to dbEST:
gi|10204347 /dataset=dbest /taxon=96...                              555  e-155

EXPRESSION INFORMATION FOR MODULATORY USE:
library source:
Expression information from BLAST dbEST hit:
gi|10204347: Eye (retinoblastoma)

Expression information from PCR-based tissue screening panels:
Human Adult Brain

FIGURE 1B

```
  1 MEGGPAVCCQ DPRAELVERV AAIDVTHLEE ADGGPEPTRN GVDPPPRARA
 51 ASVIPGSTSR LLPARPSLSA RKLSLQERPA GSYLEAQAGP YATGPASHIS
101 PRAWRRPTIE SHHVAISDAE DCVQLNQYKL QSEIGKGAYG VVRLAYNESE
151 DRHYAMKVLS KKKLLKQYGF PRRPPPRGSQ AAQGGPAKQL LPLERVYQEI
201 AILKKLDHVN VVKLIEVLDD PAEDNLYLVF DLLRKGPVME VPCDKPFSEE
251 QARLYLRDVI LGLEYLHCQK IVHRDIKPSN LLLGDDGHVK IADFGVSNQF
301 EGNDAQLSST AGTPAFMAPE AISDSGQSFS GKALDVWATG VTLYCFVYGK
351 CPFIDDFILA LHRKIKNEPV VFPEEPEISE ELKDLILKML DKNPETRIGV
401 PDIKLHPWVT KNGEEPLPSE EEHCSVVEVT EGEVKNSVRL IPSWTTVILV
451 KSMLRKRSFG NPFEPQARRE ERSMSAPGNL LVKEGFGEGG KSPELPGVQE
501 DEAAS     (SEQ ID NO:2)
```

FEATURES:
Functional domains and key regions:
[1] PDOC00001 PS00001 ASN_GLYCOSYLATION
N-glycosylation site 147-150 NESE

[2] PDOC00004 PS00004 CAMP_PHOSPHO_SITE
cAMP- and cGMP-dependent protein kinase phosphorylation site Number of matches: 3
    1     71-74 RKLS
    2    105-108 RRPT
    3    455-458 RKRS

[3] PDOC00005 PS00005 PKC_PHOSPHO_SITE
Protein kinase C phosphorylation site

Number of matches: 6
    1     58-60 TSR
    2     69-71 SAR
    3    100-102 SPR
    4    160-162 SKK
    5    330-332 SGK
    6    437-439 SVR

[4] PDOC00006 PS00006 CK2_PHOSPHO_SITE
Casein kinase II phosphorylation site

Number of matches: 7
    1     26-29 THLE
    2     74-77 SLQE
    3     82-85 SYLE
    4    117-120 SDAE
    5    419-422 SEEE
    6    425-428 SVVE
    7    430-433 TEGE

FIGURE 2A

[5] PDOC00008 PS00008 MYRISTYL
N-myristoylation site

Number of matches: 2
    1    178-183 GSQAAQ
    2    326-331 GQSFSG

[6] PDOC00017 PS00017 ATP_GTP_A
ATP/GTP-binding site motif A (P-loop)

485-492 GFGEGGKS

[7] PDOC00100 PS00107 PROTEIN_KINASE_ATP
Protein kinases ATP-binding region signature 134-157 IGKGAYGVVRLAYNESEDRHYAMK

[8] PDOC00100 PS00108 PROTEIN_KINASE_ST
Serine/Threonine protein kinases active-site signature 271-283 IVHRDIKPSNLLL Membrane spanning structure and domains:
Helix Begin   End   Score Certainty
  1   339    359   0.946 Putative BLAST Alignment to Top Hit:
>gi|1836161|gb|AAB46910.1| (S83194) Ca2+/calmodulin-dependent
        protein kinase IV kinase isoform, CaM-kinase
        alpha [rats, brain, Peptide, 505 aa] [Rattus sp.]
        >gi|4512334|dbj|BAA75246.1| (AB023658)
        Ca/calmodulin-dependent protein kinase alpha,
        CaM-kinase alpha [Rattus norvegicus]
        Length = 505

Score =  965 bits (2468), Expect = 0.0
Identities = 472/505 (93%), Positives = 483/505 (95%)

Query:   1  MEGGPAVCCQDPRAELVERVAAIDVTHLEEADGGPEPTRNGVDPPPRARAASVIPGSTSR  60
            ME  PAVCCQDPRAELVERVAAI V HLEEA+  GPEP  NGVDPPPRARAASVIPGS SR
Sbjct:   1  MERSPAVCCQDPRAELVERVAAISVAHLEEAEEGPEPASNGVDPPPRARAASVIPGSASR  60

Query:  61  LLPARPSLSARKLSLQERPAGSYLEAQAGPYATGPASHISPRAWRRPTIESHHVAISDAE  120
               P RPSLSARK SLQERPAGS LEAQ GPY+TGPASH+SPRAWRRPTIESHHVAISD E
Sbjct:  61  PTPVRPSLSARKFSLQERPAGSCLEAQVGPYSTGPASHMSPRAWRRPTIESHHVAISDTE  120

Query: 121  DCVQLNQYKLQSEIGKGAYGVVRLAYNESEDRHYAMKVLSKKKLLKQYGFPRRPPPRGSQ  180
            DCVQLNQYKLQSEIGKGAYGVVRLAYNE EDRHYAMKVLSKKKLLKQYGFPRRPPPRGSQ
Sbjct: 121  DCVQLNQYKLQSEIGKGAYGVVRLAYNEREDRHYAMKVLSKKKLLKQYGFPRRPPPRGSQ  180

Query: 181  AAQGGPAKQLLPLERVYQEIAILKKLDHVNVVKLIEVLDDPAEDNLYLVFDLLRKGPVME  240
            A QGGPAKQLLPLERVYQEIAILKKLDHVNVVKLIEVLDDPAEDNLYLVFDLLRKGPVME
Sbjct: 181  APQGGPAKQLLPLERVYQEIAILKKLDHVNVVKLIEVLDDPAEDNLYLVFDLLRKGPVME  240

FIGURE 2B

```
Query: 241 VPCDKPFSEEQARLYLRDVILGLEYLHCQKIVHRDIKPSNLLLGDDGHVKIADFGVSNQF 300
            VPCDKPF EEQARLYLRD+ILGLEYLHCQKIVHRDIKPSNLLLGDDGHVKIADFGVSNQF
Sbjct: 241 VPCDKPFPEEQARLYLRDIILGLEYLHCQKIVHRDIKPSNLLLGDDGHVKIADFGVSNQF 300

Query: 301 EGNDAQLSSTAGTPAFMAPEAISDSGQSFSGKALDVWATGVTLYCFVYGKCPFIDDFILA 360
            EGNDAQLSSTAGTPAFMAPEAISD+GQSFSGKALDVWATGVTLYCFVYGKCPFID++ILA
Sbjct: 301 EGNDAQLSSTAGTPAFMAPEAISDTGQSFSGKALDVWATGVTLYCFVYGKCPFIDEYILA 360

Query: 361 LHRKIKNEPWFPEEPEISEELKDLILKMLDKNPETRIGVPDIKLHPWVTKNGEEPLPSE 420
            LHRKIKNE WFPEEPE+SEELKDLILKMLDKNPETRIGV DIKLHPWVTK+GEEPLPSE
Sbjct: 361 LHRKIKNEAWFPEEPEVSEELKDLILKMLDKNPETRIGVSDIKLHPWVTKHGEEPLPSE 420

Query: 421 EEHCSVVEVTEGEVKNSVRLIPSWTTVILVKSMLRKRSFGNPFEPQARREERSMSAPGNL 480
            EEHCSVVEVTE EVKNSV+LIPSWTTVILVKSMLRKRSFGNPFEPQARREERSMSAPGNL
Sbjct: 421 EEHCSVVEVTEEEVKNSVKLIPSWTTVILVKSMLRKRSFGNPFEPQARREERSMSAPGNL 480

Query: 481 LVKEGFGEGGKSPELPGVQEDEAAS 505
            L+KEG GEGGKSPELPGVQEDEAAS
Sbjct: 481 LLKEGCGEGGKSPELPGVQEDEAAS 505   (SEQ ID NO:4)

Hmmer search results (Pfam):
Model      Description                                  Score     E-value   N
PF00069    Eukaryotic protein kinase domain             275.1     8.8e-79   1
CE00022    CE00022 MAGUK_subfamily_d                     45.1     3.2e-13   1
CE00359    E00359 bone_morphogenetic_protein_receptor    26.1     1.1e-06   1
CE00031    CE00031 VEGFR                                 13.6     0.00033   1
CE00203    CE00203 ERBB_RECEPTOR                          6.7     0.16      1
CE00334    E00334 urotrophin_receptor                    6.6      0.047     1
CE00292    CE00292 PTK_membrane_span                    -66.6     4.1e-05   1
CE00287    CE00287 PTK_Eph_orphan_receptor              -81.5     0.0049    1
CE00291    CE00291 PTK_fgf_receptor                     -95.1     0.0027    1
CE00286    E00286 PTK_EGF_receptor                     -119.5     0.00094   1
CE00290    CE00290 PTK_Trk_family                      -132.1     2.8e-06   1
CE00016    CE00016 GSK_glycogen_synthase_kinase        -206.4     3.1e-05   1
CE00288    CE00288  PTK_Insulin_receptor               -225.0     0.18      1

Parsed for domains:
Model      Domain   seq-f  seq-t    hmm-f  hmm-t      score   E-value
CE00031    1/1       243    296 ..  1039   1092 ..     13.6   0.00033
CE00334    1/1       264    297 ..   670    703 ..      6.6   0.047
CE00203    1/1       262    307 ..   852    897 ..      6.7   0.16
CE00359    1/1       271    320 ..   272    325 ..     26.1   1.1e-06
CE00288    1/1       179    382 ..     1    269 []   -225.0   0.18
CE00291    1/1       128    382 ..     1    285 []    -95.1   0.0027
CE00290    1/1       129    390 ..     1    282 []   -132.1   2.8e-06
CE00286    1/1       128    403 ..     1    263 []   -119.5   0.00094
CE00292    1/1       128    405 ..     1    288 []    -66.6   4.1e-05
CE00287    1/1       128    407 ..     1    260 []    -81.5   0.0049
CE00022    1/1       247    409 ..   118    283 ..     45.1   3.2e-13
PF00069    1/1       128    409 ..     1    278 []    275.1   8.8e-79
CE00016    1/1        64    481 ..     1    433 []   -206.4   3.1e-05
```

FIGURE 2C

```
   1 CCGCCCGCGC ATCCATCTGG GCCTCAGCGT GTCCCGAGCA ATCACAACAG
  51 CAGCCGCACA ACAACAACTC ACTTTTACGG CCTCCTTAGT GGCAGGCACT
 101 GTTCTGAGCG CCTTACGGGC GTTCCCTCCT CAGCATCTCA CCACGTGCGG
 151 TGAGGTGAGG CCCGCTAGAA CCCCATCTTG CGGGCGAGGA AAACCCAAGG
 201 CACAGAGGCG AAGCCACCTG CTCACGGGCT CCCAGCCAGG AAAGGGTGCA
 251 GCCTGGCTGC CTGGCTTCAG AGCCTGGGCG CCAAACCGGG TAACAGGGCT
 301 CAGGCTGGAA CAGGAAACCT TCTGCCCCGA CTTGCTGGGT GACCCCGGGC
 351 CCATCCCCAC CCGCTGGGCC TCCCTCTACC TATCTAAGAA AAGCAGGGAA
 401 AGGTGTTCAA GGGTAAAGGA GGATGGCCTC TTGCTGGAAT GGCAACCTCA
 451 AGGAAATACG CAAATTTTAT GGGCCCGGGC AGCCTGTGGC TTCTGCCTGT
 501 GGCGGCTCTG AGTCCCGTAG TCCCTGCCTA GGGCCAAAAA GCAGGAGCTC
 551 CTGACTCTGG AGTTCATTCT GTTATATGTG CTGGGGCCTG AGGCTTGCTG
 601 GGGTTGCCTC TCTGAGGCTG CTTTCTCATC TGTCTAATGG GGACAGGGCT
 651 GTAACGATCA CTATGGCAAC CACTCATTTA TTCAACAAAT ATTTATCGAG
 701 TTCCTATCAC ATGCCAGGCA CTGATGATCT TTTGGAGACA AGGCAGATGA
 751 GCGTCCTAAT CTCATGAAAC TTACATTCGG GAGGGAAAAA CAAGGCATGC
 801 GGAGTGAGGG GAAGGGGCGG AGGGGTGGGC CACCTGCTGG GAGGAGCCTG
 851 GCGGGTCCTG GAGGGTGTTC CCAGCTTTGG CTTCCTCCTT CCTATGCTGT
 901 CTGGTTTCCA AGCTCTCCCC GAAGCTCCAG CCCCACTCAC TGTCCCTCTC
 951 ACCTCCTCCA GGGAGGCCTC CCTATGCCAC AGCCTCTCAC CTCCTCTGGG
1001 GAGGCCTCCT TATGCCACAG CCCCACTCTC TGTCCTCTCT CACCTCCTCC
1051 AGGGAGGCCT CCCTGTGCCA CAGCCCCACT CCCTGTCCCC TCTCACCTCC
1101 TCCAGGGAGG CCTCCTTGTG CCACAGCCGC ACTCACTGTC TCCTGCCCTC
1151 TCTTCCAGGG AGGCCTCCCT GATACTCTAG CCTCACTCAG CCTCCTCACC
1201 TCCTTCACCT CCTCCAGGGA GGCCTCCTTG ATGTTCCAGC CTCATTAACT
1251 CCCTCTCACT CCTCTGGGTC CAGCTTCCAT GACTTTTCCT GTTCCTAGTG
1301 TGGAGCCTCC TCTCTTCCTT TCTCCATGTC AGCACCAGCC CCACCGCCTC
1351 CAGGCTTCTA CTCATTCAAC ACACTGCGTA CCGGGCACAG GGGGTCTGGA
1401 CCTCACCCTT ACCCTCAGTC TACCTCCAAA CCCTGCTGTG AGCCTGGAAA
1451 ATATGGGAAG GCAGGGAATC CACAGGACAA GTCGGGAGAC TGGGGCTCAG
1501 AGTCGGGAAG GAGCTGGTCT AGGGCCCCTG GTGGGTCAGC AGGCAGGACT
1551 GGAACCCAGT CCTGGCTCCT CAGTGGCCGG TGGACTCCAG CCAGCCCTGC
1601 CTCGCTGACA TCTGTCAAAG CAAGGGGATG GGAACGAGC GGTAGAGCAG
1651 GCGCTTCACC ATGCGTACTC TGGGTCTCCC TGAGACCCAT GTTCTCAGTT
1701 GCTGTGTGGG TTCGGAGGAA GTTACCAGCA GACAGGAAGG ATGGAGGGTC
1751 AGGAGTTCAC TCACTTCCTT CTCCTGAGAA CATGCAGAGT CCAGCGCAAG
1801 CAGGGGGAAG GGCATCAGGT TGGGCATGGC CAGCGCTCTA CAAGCCTGGG
1851 ACAGAGATGG GGGTCTCAGG CTGAGTGTCA GGGTTCAGTC CGGGGTCAGG
1901 ATGTAGCCCA GGGTCATGGC TGAAGGTGAG GGCTGGGGT CACCTCCCTG
1951 ATGTTTCAGC CGCCACACAG TGAGTTTGAG AACATGAGTC TCAGGGGATG
2001 TCATGCCCCT GTTTCACCCC TCATTCCCCT CATTCCCATC CCCTTGCTTT
2051 TTTTTGAAAC CGAGTCTTGC TCCATCACCC AGGCTGGAGT GTAGTGGCGT
2101 GATCTTGGCT CACTGCAACC TCCACCTCCC AAGTTCACAC GATTCTCCTG
2151 CCTCAGCCTC CCGAGTAGAT GGGATTTCAG GTGCACGCCA CCATGCCTGG
2201 CTAATTTTTG TATTTTTAAT AGAGACAGAG TTTTGCCATG TTAGCCAGGC
2251 TAGTCTCGAA CTTCTGACCT CAGGTGATCC ACCTGCCTCG GCCTCCCAAA
2301 GTGCTGGGAT TACAAGTGTG AGCCACCATG TGGGGCCCAT CCCCTTGTTT
2351 TGACAGACGT CAATGAGGCA GGGCTGGCTG GAGTCGGGAG CCCCAGGGAA
2401 GTCTTCCTGG AAGCAGTGAG AGGGATGGGG GTAGGAGGCT GAAACATCAA
2451 GGAGGGCTCC CTGGAGGAGG CGGGTGGGTC TGAAGCATCA GCAAGGCTTC
2501 TGAGTTACTA GTGTCTAGCT CAGCTTCCAG GAGGCAGTGT CGGAGTGCTC
2551 TGCTGTCAAG GGTTGGGACT CATGACTCAC AGGGCTGCAT GCTGTGCTGG
2601 GGCTGAGCTG ACCCTGGGCT CTGCCCCTTC CAGTGCTGCT GGGCCTCCAG
2651 GCTTCTGCCC TGTCTGTCCT GATTCCAGAA TATCAGATTC TCTCTGCTTC
2701 CCTGTGAAGC CAGCAGGCAG AAGTGACTGC CTCTGTTACC GGCAGGGATA
2751 CTGAGGCCTA GAGGGCTGGC ATGCGGCAGA ACCGATGTGA ATTCATTCAG
2801 GTCATAGGGA CAGACTTGAG TTTGGGTGTT GGCAATCCCG GTAGAGGGAA
2851 CAGCCAGGGC AAAGGCATGG AGGTGGGACC CACAGCGCTG TGGCTACCTT
2901 ACCTGGTAGC CAGCCTGACA CCCAGGAGTG AAGCCTTCTC TGCCTTCTTT
```

FIGURE 3A

```
2951 TCTCAGGTTC CCAACAAGGC TACGCAGAAG AACCCCCTTG ACTGAAGCAA
3001 TGGAGGGGGG TCCAGCTGTC TGCTGCCAGG ATCCTCGGGC AGAGCTGGTA
3051 GAACGGGTGG CAGCCATCGA TGTGACTCAC TTGGAGGAGG CAGATGGTGG
3101 CCCAGAGCCT ACTAGAAACG GTGTGGACCC CCACCACGG GCCAGAGCTG
3151 CCTCTGTGAT CCCTGGCAGT ACTTCAAGAC TGCTCCCAGC CCGGCCTAGC
3201 CTCTCAGCCA GGAAGCTTTC CCTACAGGAG CGGCCAGCAG GAAGCTATCT
3251 GGAGGCGCAG GCTGGGCCTT ATGCCACGGG GCCTGCCAGC CACATCTCCC
3301 CCCGGGCCTG GCGGAGGCCC ACCATCGAGT CCCACCACGT GGCCATCTCA
3351 GATGCAGAGG TTGGTGGGGC AGAACGAGGG GTTGTTCATG AGCCCCTCAG
3401 TAGTCTGCAA TGAAGACTCT TTCCTGCCCC TGTCTGTGCC ACACGGCTAT
3451 CTAGCTTTGG TTTGCATACC CTCAGAGCTG GGGAGATCAC TACCTAACAA
3501 TATAGCTTCT TCCCAACCAG GGGAGCTCCA GCTGAGCCAA AGGCTGCCTT
3551 CCCTAAGTCC TGCTATTCCC ACTCCCAGCC CAGGCCTAGG AAATAGGTCT
3601 CTCCCTGGTC CCCTATGTAG TCTTCTTAGA GATGTGAAGA TAGATGCTAT
3651 GTCCCCCTTC CCCCCTAACT CTTCTCCAGC TTGCACCCCT CGCCTCTAAT
3701 TCTGCCTCTT AGAGTCTGCT GTGACTCAGA AGCGGCCGGC CTGCCTCCAG
3751 CCTCTGGGCT TCTGCTGGAG TTCTTGCCAT TTAGGTCTGA AAGTGAACTC
3801 AGGTTCCAAG CAGTCTACAG ATGTCAGGGG CTGAGCTTTC TGTGCCTGAA
3851 CCCAGGCTCT CAGCCTCTGT GCCCAGGGCT CCTCATCTTG TCCTTGGAGT
3901 CTAGACCTTC TCATTCAGCT GCTTCTGGAA ATAGTTGCTC ATGGGTTTCT
3951 CATGGATTAG GGTCTTCCAG ACTCCAGAAT CCAGACAGGA ATTAGCGTTT
4001 TCCCTTCACC ACTGCTTCTG GGGAACAAGG CACAGCCATG GCGTCACCAT
4051 CCATGTTTTC AAACATGAGC CACGTCTTCT CGTCACATAC GGGGGCGATG
4101 GCACCACCAA CTTCCCCATC CAAACTCAAA AGCTTGGTGA GACCTGGGGG
4151 TCCGGGAATG AGGAGCTTAT GGCCAGAATT GGACCCTGAA CGGGCTCTGA
4201 GGTAGGAGCA GTGCTGCCTC CGGACCCAGC TCCACCTGGT GCTCGCTCTT
4251 CCCCCACAGG ACTGCGTGCA GCTGAACCAG TACAAGCTGC AGAGTGAGAT
4301 TGGCAAGGTA GGAGTGGGCA GGCCGAGAGC AGTGGGGGCT TCGGGATTCT
4351 CTGTTTGGCG CTGCTCCTTC TCTCGTGTGG GAGGGAACGG GAGGCAGAGC
4401 CAGGCAAGTC CTAGCCTGGA GGTGAGGACA GTTTCGTGCC CTGTGGGAAG
4451 TACCCAGGTA CCCAGGGGA GGGTGGAAGA TGGCTCCTGA TTCCCGACTC
4501 TCTGAGTTCT TGACAGTGGA CAAGGAGGGA CTGAGGGAGG CATGGAGCCA
4551 TGTGGAGCCA AGCAGGGCA GTTACCAGGG CGCAGGAGTC CCCTCCCCAT
4601 CTGCTACAAT ATTTGCCCGT GAGCCAGCTG GTGGTGGGTA GTGCAGATGG
4651 GGTGCAGGAG AGACCAGAGC TGCTCGGCTC CCCACCTCCT GAGCTGGTCC
4701 TGGGAGGGGT TGCCCTGTCC AGGTGGGGCT GACTGATGCC TATCTGCAGG
4751 GTGCCTACGG TGTGGTGAGG CTGGCCTACA ACGAAAGTGA AGACAGACAC
4801 TATGTGAGTC TGGGGATACG AGGGAGGTGT TGCCCAAGCC AGGCCCTGGA
4851 AGCCTGAGGG GTGGGGCAGG AGTTGTGCTT AGGAGATAGA GGACAGGGCT
4901 GCCTGAGAGT GAGCTCCCTG TCCCTAGGGG TATGCAAAGG AATGAGCTTC
4951 CTAACCCTGG GGATATGCAA GCAGAGACTG GATTCCTCTG AGGGGAAAGC
5001 TCCAGAAAGG CTTGCTGGGG GAATAAGGGG AAGGGCTAGG CTCAGATATG
5051 GCCACCCCCA ACCCCGCTTA ACACTTACCT GGGCCACACC CTCAGGGCCA
5101 GTAGCAGATG TCCAGTGTGC CTCTCCGGAC CTCAGTCCAC ATGTACCAGC
5151 CTGTTCTAGC CCCTGGTGGC TGCACAGTAG TGACATTTCT GTCCCTCCTT
5201 CCTTAGGCAA TGAAAGTCCT TTCCAAAAAG AAGTTACTGA AGCAGTATGG
5251 CTTTCCACGT ATGTATCTTC TGATCCTGTC CCTGGGAGCT CCTAGCCTGG
5301 AGGCAGAGGA GGAGACCTCG ATCCTGAGCT AGTTTTGGCT AGGAATGGGG
5351 TAGAGAGGGA GACAGCGTGA GCAGAGGCCT GGGGACAGAA TGTGCCCTGT
5401 GGGTTGGGAC AAGACCACGG GCATGCAAGA CTCTTGCTTG AGACTGGTTT
5451 GGGGGCCACG GTGAGGCCCA GCCACCTGGA ACAGGTGTTT GAGTTCTCTT
5501 CCTGGTCACA GGTCGCCCTC CCCCGAGAGG GTCCCAGGCT GCCCAGGGAG
5551 GACCAGCCAA GCAGCTGCTG CCCCTGGAGC GGGTGTACCA GGAGATTGCC
5601 ATCCTGAAGA AGCTGGACCA CGTGAATGTG GTCAAACTGA TCGAGGTAGG
5651 GGGTGGTGGT GAGCAGGTGG GAACCAGCAC CTGAGTCTCA TGGGAGCCGC
5701 TTCTGGTGCT GGGGAGCCCC TAGCACAGAC CCAGGGATCT TGCCCAGGTG
5751 GCAGATGTGG CTGAGGCCTC TGAGGACAGG GCCAGACTTG GGGTGGGGCT
5801 GCAGGAAGGC TTTGGGGGCC CAGCCTGGTC AGGGATGTTC CCAAGTTCCC
5851 ATGGAGGGTG AGGGGCTGCC CCAGAGGCAA GAAGTGAGCC CCTCATTGCA
```

FIGURE 3B

5901 GCTGGAGGGG AGGAAGGCTG GATGTCGTGT GGCGGGCCAG GTTGGGGGTC
5951 GGTGACTTCT GAGGCCCCAT CAGTCTGGCA CCACCTGTAC ACTTCCTGCT
6001 TCCTTGTCTG GGGTGGTTGC ATGCATACTA AGGGTTCTGG GGCTGGCAAG
6051 GACCAGGAGG CCTGGGACCT CCAACCCCAC GCCTCCTCAA GCCCCACCCC
6101 CATGTCTGCT CCCTCTGACC AGGTCCTGGA TGACCCAGCT GAGGACAACC
6151 TCTATTTGGG TGAGTGACCT GGCTCATTCC CACAGCAGCT CACTCAGGGC
6201 TGGCCCAAGG GCTCCCTTGG GACATGTATG ACCTTCAGGT GGGCGGTGTA
6251 AATGCACTGA CCTCCTGGGG ACAGAAGAAA AACACACGTT CTGAAGCCCT
6301 GGATTCCCTT GCCCAGCCCT GCAGAACCAG GCCCAGAATA TCCAGTTAGA
6351 TTCAACAAAT ATCGCCAAGC CCCACTCCCT GCTTCCCTCT GAGCAGCAAG
6401 ACAGTGGATC CACGTGGGCT GCGCGCTCAG GTAGATGCAG GAAGCAGGCT
6451 GCATGGGTTC CCAGACACTG TAGCTCTGTG CCTCAGTTTT CCCACCTATA
6501 AAACAGGGAT ACTAGTGGTG TCTACCTCAT AGGGTTCCTG TGAAGAGTAA
6551 ATGAGTAATT ATATGTAAAG CACATTCGTT ATTATCCTTG TTAATAGTAA
6601 TGTTATTATT TTAGTTCCTT GTGTCTGGTT CAGGGCTGGG CTTAGAGGAG
6651 GCCTCAGAAA ATGGGGCAGA AGAAGAACTG GCTTAGGAAT TAGAGGCTGA
6701 GGCTTTAGTC TCCACTCCCT ACCCTACCTG CCTGTCTGCT ATGACCTTTA
6751 GGAAAATTTC TGCCCCTTCT CTGTGCCTCA GTTTCCCCCT CTGTAAAAGG
6801 GCCCCATGCT GATGCTGATG GTTCTCACCT GGCACCTGAG GATCAGATGA
6851 GACAGGTCCA TAGCAGACCC CACTCTCATG CATTTATTTG CTCTCATATC
6901 CCAGGGTCCC CTGTCCTGTC CCTGCCTCGA GTATGCCTGC ATGCCTGCCC
6951 CCTCTCCTAC CCTCCAGAAC AGGGAGGGAC CTTGGCATCG GCTGCTTTGC
7001 CAGCCAGCTA CACCTTACCT TCTTGTCTTT TCTTTCAGTG TTTGACCTCC
7051 TGAGAAAGGG GTGAGTTCCC CGTCCTGATC AGGCAGGTCA ATTCTCATCC
7101 AGGCCTTCCT TCCTTTCCCT CCCTGTGTCC CCAGCCCAGG GGTCAGCTAC
7151 TCTAGGAGAA GTCAGAGACG GAGGCCCTGC CCTTAGGGGT AAATAAGAGA
7201 CCAAGAGGAC CATTCTTTGA AGGCTGATGG GGGTCAGTGA GGCTGAAATA
7251 GTCAGGGAGA CCTCTGGAAA AGGGGACGGA TTTTGACCCA GGCCTTGAAG
7301 AACTAGGAAG ATAGGGATGG AGGAGAGGGG GAAGAAAGGA GTGTTTTTTA
7351 GGTAAAAGTA TATAGAGGTG GGACTCAACT CTTACCGGTA TTCAAATCAC
7401 AAAGGGTTTT TCAGCTTTCC AACAAGTCTG TGAATGGAGT GGGTGGGATT
7451 CCAGTTGCTC CCATTTGTGA GAGGGAAAGC TAAGGACCAG AGAAGGTACG
7501 TGGCTTGCTC AAGGTCACAC AGCAAGTCAC TGATGGAGCC CAGGCTTCCA
7551 CATGTCTGCC CTATGCGGCT TTTCAGGGTA TTTACAGAGC AGATGACATG
7601 GAGTAATGAG CACGGGGCTG GGTGGTCCGG GACCCTCACT GCCAAGGCTT
7651 GAATGCAGCC TGCGGCTTGT CCCTTTGCCT GGGCGGCTCC CTACAGACCA
7701 ATCTGGGGAG AGGGGCAGGG AGTGGTGTCC CTTTAAGACT TGGAGGCTTT
7751 CAAATGTTTT GACCTCTATC CAAAACAAGA AATATATATT TCTATTGCTA
7801 TCCATATCTG TAACTGAAAC CAAAATTTTA CAAAGCAGCA TATATCTTTA
7851 CTACATGCAA TATATTCTGA TATATTCTAC TTATTTAGGA AAAAAAAAA
7901 AAAGCAGTTG CCACCCACTA AATTGATTTC ATGATCCTCT CTTGGGTCTG
7951 GATCCACGGT TTGAAACAGT GCTCTAAATG GCATCTTTGC AATTGATTAT
8001 GGACAATTAA GTACTTAGAA GAAGGAATAT CAAGCCAATC AGAAATTAAG
8051 AGAAAGCTGA TTTGAAATTA TGATTGAAAT GGGATATGTA TGAGTATGTG
8101 TGCTTTAAGT TTTTTATTAT GTAGCAGAAA AAGCTAATAT CTTGAGTTGT
8151 AGGGACTCAT GTGGGCACAG GTTTCCCGGG ACGTCCCGAC CACCTGAATG
8201 GCCGGGTGCC CTGATTTCAG CTGAATGCCC CTCCCCGCAT CCTTCTCCAT
8251 AGGCCCGTCA TGGAAGTGCC CTGTGACAAG CCCTTCTCGG AGGAGCAAGC
8301 TCGCCTCTAC CTGCGGGACG TCATCCTGGG CCTCGAGTAC CTGCACGAGC
8351 GGGCAGCTTG CCCACTGGGG CTGGGGCTAG GGGATCTGGC AGGCGGCAGA
8401 GCCCAGGCTG AGCAGACTCT GAGCAGCTCC CGTCAGTCAG AGCTGACCTG
8451 CCAATCAGCT TCAGTGGGAG TGGGGCATGC ACGTGTGGCG GGGCCAAAGG
8501 CCTTTTTGTG GGGTGGGGCG GGCGGTGGAC TCCACTGGGC ATGTGCCAGA
8551 TCCTTCGTCG TGTCTGGTCC TGTGGGTCTG AGTCCTGGCT GTTCTGTATC
8601 TTTCTTCTGC TGAGTTCTTA GCCTAGCTTA GCGTTGCCAC GGGGCTTCAA
8651 GAGATGTGGG AAGGAAGGGA TTTATGTCCA GCTGCTGGGG AGAGTCTGTC
8701 CTGGCATGGG GCCGGGGCAT GGTGGCAGGG TGGATTTACC TGTGAGGGGC
8751 CCTAGTCTGA TAAGAGCTCA GGAGGGTGAT GTGAGCTTGG CCTCTGTCTC
8801 ATTTCATTCA TTAGCTACAT TCACTTGCCT GGGGGCATAG GGGTGAAAGA

FIGURE 3C

```
 8851 CCCAGACCCG AGTTCACGGC CTAGTGGGAG GGACAGGAAT CTAGGCAGGC
 8901 AGATAATACA GCGTGGTGCC TGCCAAGGCT GGGGAGCCTA GAGGCTGTAG
 8951 GAGTGCCGGG GGGCTGGGGA AGTCTCCCTG AAGAGGCTAC TTATGATTCG
 9001 GGTCCTGAGG GATGAGTAGA CTTCCCTGCT CAGGTTTTGA GGGATGGGCG
 9051 TGGAAGACGA TGTGCCTGGC ATAGGCGTGT ACTCTGAGTC TGGGGAGAAG
 9101 TGGAGTCTGG CTGAAGCCTC CAGTGGGCAG AGGAGGGCCG TGGTTAGTGA
 9151 AAGATGATGC TGGAAACACT GTCCGGGCCA CAGCATGAGG GCTGGGAATC
 9201 CCTCCCCTGA GGTCTTTGCT GACTGCATCC TGCCAGCTCT GTGAGGCCCT
 9251 GAGAGCTTTA AGCATGGGGA GGGGCGTGAT GGGATTTGTG CCTGAGAAAG
 9301 CTCTGTCTGG CAGCTGTGTG GTGGCTGGAT TGGAGTGTGT CATCGGAGGG
 9351 TGAGAGGCAG CCAGCTGGCC AGGGAGGAGG CTGTTTCTGC AGCCCAAGTG
 9401 ACAGATGGTG AGGCCTGGAT TAAGGCAGTG GCAGCAGGAT GGGGATAGGA
 9451 AGGAGGTGGG GTGGTCAGCA TGGAGTGACT TGCCGGTCTG GGGAGAGGAG
 9501 AGCCCCTAGA CACCTAGGGT CCTGGCGTGG GTTGGGGACC AGGGGAGATG
 9551 CCCATCTCTA AAATCTTAGC TTGGGCCAGG CGCAGGGGCT CATGCCTGTA
 9601 ATCCCAGCAC TTTGGGAGGC CGAGGTGGGT AGATCACCTG AGGTCAGGGG
 9651 TTTGAGACCA GCCTGGCCAA CGTGGCAAAA GCCTGTCTCT ACTACAAATA
 9701 CAAAAATTAG CCTTGTGTGG TGGTGGGCAC CTGTAATCCC AGCTACTCGG
 9751 GAGGCTGAGG CAGGAGAATC GCTTGAACCT GGGAGGTGGA GGTTGCAGTG
 9801 AGCCGAGATC ACGCCATTGC ACTCCAGCCT GGGTGACAAG AGTGAAACTC
 9851 CATCTCAAAA TAAATAAATA AATAAATGCA TACATACATA TATACATACA
 9901 TACATAAAAA TAAAAAATAA AATCTTAGCT TGGTTTCTTG GGAGCATATT
 9951 CTTTCCCTGG GGAACAGGG TGGGGATCTG GCTGAGGTTT GACCTGCAGT
10001 GACAGAAACA GGACTGTCTT TATCCTGCTC GAGCCTCTCC TTTGCCTTCA
10051 GATTAAGACT CTCTTTGCAC ATATGGGGAA ACTGAGGCAC ACAGAGGGGA
10101 GGGCTTTGCA GAAAATCCCT ACCAAGGGCC TAGAGGCATG GGATGGGAAG
10151 GGGACATTTT ACCCCGGTAC GGTCAGTGGC AGGCACAGTC CTGTACCAGC
10201 TTGGCTCCAC CTCCTTTCTG TTGTAGTCCC TTCTTTCCCC TGAAGTCCTG
10251 TTGTCTGCTA TCCCCTAGCC TCCACAAAGA AACGAGTTTA TCTTACCTGG
10301 TTCTTGGGTA AAGCCTCATC AGGACCCAGC TAATCACAGT GAAGGGCTTC
10351 CCTGGGGCAG AACGGTTAGC GCCAGGGGCT GGACAGGTGG ATGAACAGAG
10401 GCACGAGGGC GCTGAAGACC TGCCTTGTGA TTCTGGCCCC AAGAAGAGAG
10451 AGTTGAGGCT GCCATGAGAG GGCTCGGTGG TCAGGGCGGC CCAGGCCTGG
10501 TTCTCAGTTG ATGGGGGCAG GTGCAACGAT GCAGATGATG AGAAGCAGTT
10551 GGATCTGGAA TAGATGTGAG AAGCTGAGCT CACAGACCTT GCTGATGAGC
10601 AGGATGTGGG GTCTCAGAGG AGGAATTGAG GATGATCCTG AAGTTTTTGG
10651 CCTTTCACAG AATGGAAAAG AATGGGGAGC AGCAGGGGCG TTTTGTTTTG
10701 CTTTGTTTTG ATTTTGTTGG TGGTAGGCAT TGCAGGCAGA GAAATCAAGT
10751 TCTGAATTAG ACATGTTATT GCACTGTGTT CAGATATACA GAGACATATA
10801 TCGATGCCTA GCTGCCTAGT TATCTACCAA GATGTCTATT GGAAATCTAT
10851 GTGGGTAAAG AGCTGGAGTT CAAGGGAGAG GCTAGGGTTT GAGATAAGAA
10901 CATGAGACCA CTTTCCATGG TCAAATGTCC ACCCCCCTGA GCTTCTGTGC
10951 CCTGAAGGGT GTGTCAGATT CCTTGTGTGT GCCTGGCACA TAGTAGGCAA
11001 TCAAGAAAGT GCCACTGGTT TTATGGTTAT TGTTATACGG CACCCGCCTT
11051 CTCTGCCCGC AGCCTCCCTC TCCTCTTCTC CCTTCCTCTT TCTTCTCTCG
11101 CCTTCTCTCC TCCCTCCTCT CCAGCATCCT GGGGTCCGTT GGTCCAGATG
11151 AAGGTACTTG CCAAGGAGGG AGCCCACAGG TCGATGGTCG CGGGATGGGG
11201 TCAGTGGGGT CATTGTCTCT CTTGGCTGGG ACCTTACCAG TCATGTCAGC
11251 TTGAGCCACC TGTCACTTCG TGGTGGTGCT GGGCCCAGAA AGCAGGGCAG
11301 ACCTCCAGCC TATTAGGTCA TTTCTGATTT GGGATTCGTC CTACTATATG
11351 TGGCTGACCT TACACCCCAG CTGTGTCATC CTGCTTGTCC CAAGGCCTGG
11401 GGTGCCATCC ATCTCTCTGA AACCCCATCA GCCCAGATCC CGAGGGCTGA
11451 GATGGTACCT CTGTAGGATA GCAGAGTCCC TACAATCTTA CTCTCAGTCC
11501 CAGCAGCAGG GACATCTTTG CCTAGCCTGG GTGGGGATG GAACTGGAGA
11551 AAGGTTTTGA TTGGCTTTGG GCCTGCAGAC GGCACTCACA GGGAAGGGGC
11601 AGAGCTAGCC TAGGAAGAAC TCTGCTCCCA GCTGGGGCG GTGGCTCACG
11651 CCTGTAATCC CAGCACTTTG GGAGGCCGAG GTGGGTGGAT CACCTGAGGT
11701 CAGGAGTTCA AGACCAGCCT GACCAACATG GCGAAACCCT GTCTCTACTA
11751 AAAATACAAA AAGTAGCCGG GCGTGGTGGC AGACACCTGT AATCCCAACT
```

FIGURE 3D

```
11801 ACTCGGGAGG CTGAGGCAGG AGAATCTCTT GAACCTGGGA GGTGGAGGCT
11851 GCAGTGAGCC GAGATCACGC CATTGCACTC CAGCCTGGGG GACAGAGTGA
11901 GACTCTGTCT CAAAAAAAAA AAAAAAAAAC CAAAAAAAAA AACAGCAACA
11951 ACTCTCCTGC CCTAGTTTCC TCTGACCTCC CCACTCAGCA GCAGATCCCT
12001 TGTTTGTCAT GGAGAGGGTG CTGGACTTGG AGTCCAAAGA CTCCTAAGAT
12051 TCCAGTCCTG GCTCTGCTGC TCACAGCCTG GGCTCAGTGT CTGCACCTGC
12101 GTGGAGCAGA TGGCCCTGAC GTCCTCCTCC CAGGTCGTCA CCAGACGAAA
12151 GTGTGCATGG GCTGGGATGT CCCGGCCGGC GTCCCTGGCT GTGCAAGGAC
12201 GGGTGTGGGG TCCTGGCCAG CGGTGCCCAG GCCAGCGCTC AGCTCAAGCT
12251 CCCCTTCTCT GCAGTGCACT GCCAGAAGAT CGTCCACAGG GACATCAAGC
12301 CATCCAACCT GCTCCTGGGG GATGATGGGC ACGTGAAGAT CGCCGACTTT
12351 GGCGTCAGCA ACCAGTTTGA GGGGAACGAC GCTCAGCTGT CCAGCACGGC
12401 GGGAACCCCA GCATTCATGG CCCCCGAGGC CATTTCTGAT TCCGGCCAGA
12451 GCTTCAGTGG GAAGGTGACT CGCAGGCCCT GGGCCAGGCT GGGGTTCAAG
12501 TGGGGGGCGT AATAGCTTGC CGCAGTGGCC CAGTTTCTAA CCTGAGGGTG
12551 CCAGGGTCTT TGTGTCTAGG GAGTGACATA TTTGCCTCTT CCTTGGAGCC
12601 TGACAAACTC CACAACTTTG GCCTTCTCCT GTTTTCCAGC AAAGTGGTCC
12651 CAAATCTCCC TTGCAGATAT TTACTGTTGG TTGCTCTGTG CTGGGTTCTG
12701 GACCGGACTG TGGAAGAGGC AGAAACAAAG AGAACCCTGT TTCCTGCCCT
12751 CTGGATGGTT TCGGGGAAG TTGGGGGTCC CCGCAGATCT TGGGACATGG
12801 CAGGATTTGA ACTGGCCCTT GAAGAATGGG GAGGATCTGA GCAGGACCTG
12851 GAGCCTAGAG AATAAACCAG AGAACAGAAG GGCTCAGGGT GGGGGGCAGA
12901 GGGTATAAAG GGCCTGGAAG TTTGGGCTTT CTCCTAAGTG ACAGGAGCGT
12951 AGGCAAAGTT GTCTGAACAA GAGGTTACAC GGTCTGGCGC AGTTCCCTGG
13001 GCACATGGCT GTTTCACCTA TGGAGTGCCA GCCACCCCAC TGCCAGGGAG
13051 GCTGTGGGTG AGAGGCATTT GGACACGTGT GAGTATCCAG GAAAGAGGTC
13101 AGGAGGCCGG GCACAGTGGC TCATGCCTGT AATCCCAGTG CTTTGGGAGG
13151 CCAAGGTGGA TCTCTTAAGG CTAGGAATTT GAGATGAGCC TGGGCAACAT
13201 AGCAAGACCC CATTTCTACA AAAAAAAAAA TAAAACATT AGACAGGTGT
13251 GGTAGTGCAC ACCTGTAGTC CCAGCTACTT GGGAGGCCGA GGTGGGAGGA
13301 TCGCTTGAGT CCAGGAGTTG GGGGCTGTAG TGAGCTGTGA TGGTGTCTAG
13351 CCTGAGTGAC TGAGCGACAC CTTGTCTCGA AGAAAGAAAG AAAGACGTTG
13401 GGGATGTTGA TAAAGATTTT TTGAAATGTT TTATTTTGAT ATAATTCTAA
13451 ATTTACAGAA AAGTTGGAAG AATAGTACAA AGAAATCCCC TATATCTTTT
13501 TACCCAGATT CACCAATTAT TGACATTTTG TCCCACTGGC TTTTTCATCA
13551 TCTTTCTTTT TTTTTGAGCC GGAGTCTCGC TCCTGTCGCC CAGGCTGGAG
13601 TGCAGTGGCG CGATCTCAGC TCACTGCAAG CTCCACCTCC TGGGTTCACG
13651 CCATTCTCCT GCCTCAACCT CCCGAGTAGC TGGGACTACA GGCGCCCACC
13701 ACCACGCCCG GCTAATTTTT TGTATTTTTT AGTAGAGACG GGGTTTCACC
13751 GTGTTAGCCA GGATGGTCTG GATCTCCTGA CCTCGTGATC CGCCCGCCTC
13801 GGCCTCCCAA AGTGCTGGGA TTACAGGTGT GAGCCACCAC GCCCAGCCAG
13851 AAATTTATCA TTGATAAGAC TTATATATCG GTCAGGCATG GTGGCTCATG
13901 CCTGTAATTC CAGCCCTTTG GGAGGCCAAG GTAGGTGGAT CACCTGAGGT
13951 CAGGAGTTTG AGACCAGCCT GGCCAACGTG GTGAAACCCC GTCTCTACTA
14001 AAAAATACAA AAATTAGCCG GGCATGGTGG CGGGCACCTG TAATTCCAGC
14051 TACTTGGGAG GCCGAGGCAG GTGGATCACC TGAGGTCAGG AGTTTGAGAC
14101 CAGCCTGGCC AACGTGGTGA AACCCCGTCT CTACTAAAAA ATACAAAAAT
14151 TAGCCGGGCA TGGTGGCAGG CACCTGTAAT TCCAGCTACT TGGGAGGCTG
14201 AGGCAGAAGA ATCGTTCGAA CCCAGGAGGC AGAGGTTGCA GTGAGCTAAG
14251 ATCGTGCTAT TGCACTCTAG CCTGGGCGAC AGAGTGAGAC TCTGTCTGAA
14301 AAAAAAAAGA CATACATAAT CCACAGACCT TATTTAAATG TTATCAGTTG
14351 TCCTGATACT GTACTTCATA ACTTCTTCTT TTTCTGGTCC CGGAATCCAA
14401 TCGAGGACCA CTTGCTGCAT TCACCTTCTT GTCTGTGGTA TCCTTTCATC
14451 TGGAAGAGGG CCTTGGCCTG CCGTTGTCTT TCCTGATCTT GACATTTTGG
14501 AAGACAACCA GCCTGTTATT TTGTAGAATG TTGTCAGTTT GCATTTGTCT
14551 GGTGTTCCCT GGTTGGGATT CAGATGATGC ATCTGGGCA GGAATATGTA
14601 GGTAGAGATC GAGAATCACT CATATAAGCG AGAAAGTGGA TACCAGAAGA
14651 GGTGGCGTTC CGGAGCAGAA GGTAGAGAGA GCACACGCTG GAGTCCAGGG
14701 CGCGGGGAGG CCCAGGGGTG TTTGGGAGCC CAGAGGAGTT GTTGCAGTGG
```

FIGURE 3E

```
14751 CGGTGGATGA GGGCGTGAGA GGACAGGGCC TCTGTGTGGG CAGGGGCTGT
14801 TTGCAATATC AGGAAGAAGG TGGATTATGA GGAGAAGGGA TGACTCCTTG
14851 AAGCCCGAGC TGGTTTAGTG AGCAGAAGTT CCATATATAC CATCATTCCT
14901 GGGGTGCCGTC TGTGGCACGG GAGCGGCCCG TGTGACCCTC TGGATGAAGG
14951 AGGTTTTGTA CCTGTTGAGT TGGAAACGTA CCTGGTTAGA GTCTTTCCCA
15001 AGGAAACCCA GAACCCCTGG AGGGTGGAGG CCTTGTTCTG GCCGCCCCTG
15051 TGTCCTCAGC ACTCAGCACG GGGCCCAGCA TCGGGCAAGT ACCGCGGAGT
15101 GTTTGTCGAG TGAGTACATG ACAGAGGAAA GAGGTTCCCT GCAGGCCTCT
15151 CCTGCAGCCC GCTGGAGCTG GGTGGGCAGA GGTGGCTGTG CCTGTTGGGG
15201 ACTGATGTGA GCATGTTTCT TTCCAGGCCT TGGATGTATG GGCCACTGGC
15251 GTCACGTTGT ACTGCTTTGT CTATGGGAAG GTGAGTGCCA GGGATGCCAG
15301 CAGAGCTGGG GCGGGTCCAG TGAGGCGGGC ACGGGCGACG GATGCAGGCT
15351 CTTCCTTTTT GTCCTTAAGT GGCTTTTGAA AGAGCCCACC TGGCTCAGAG
15401 AAGGCTGAGA GAGAAGAGGC TTTTTCTATC TTTCTCTGGT CCCCTGCGGA
15451 GCGATTCTCG CGAAGGAGTC GCAGGACAGC AGACACCTAA GGGGAGGTGC
15501 CGACGATGGT GTTGCCACCG CCCCAGCCAG AGTGCTCCCC GTCCCTCTGT
15551 CCCTTGACGC CATTCACTTA TTGAGCCATG TGTTCACTCC CTTGCTCATT
15601 TATTCGACAA ATTGTCCTTC ACCCCTACCC TGGCTGAGGC TGGACCCTGG
15651 GGACACCCAA CGCTGACGTA TCGGTGATCC CTGCCCGCAG GTGTGCCTGC
15701 TCTGGTGACC ACACTAAGGG GCAGGGGGA ATTTCAGTGA ACATGTTCCC
15751 AAGCCCCAGG CCCTGGGAGT GGAGGCCTGG CCACAGGTGG CGGTAATGGT
15801 GGTGGGTGCA CCCAGCCTGG CCTGGCTTGG CCGCGGGTGG CAGTAACGGC
15851 GGTGGATGCA CCCAGCCTCA TTGTTCCCTC AGCAACTCAT TCATTCAGTC
15901 AACATTTGTT GAACATTTAC AGTGTGAGTT GAGGTCCTTC TCATGTAATG
15951 GGAGCCCAGA CCTGCCCCCT ACCCCTGCCC CCACCAAGGG AGGGGGGTTG
16001 ATCCCCTGGC ACAGGTCGAG GCCCTGGACC CACATCCTTT GTCTGCCTCT
16051 CCACCCCACA GTGCCCGTTC ATCGACGATT TCATCCTGGC CCTCCACAGG
16101 AAGATCAAGA ATGAGCCCGT GGTGTTTCCT GAGGGGTGAG TTGTCCACCC
16151 AGGGGAACAA GGGGGCTACC ACCCGCTCCT GGTGTCTGAG TTTTAGCAGA
16201 GCTTTTGCCC TCTGAGGACC CCACCCCAGC CTGCAGATAT GAAGGTGGCG
16251 GTGCTGTTCC CTGGGAGGGA CCCCTGAATA GATGGACGGG AGGGACTCTG
16301 GAGCCAAGGG TCTCCGCAAC GTCACTGTGT GGATGGGAAC CCTGAGATCC
16351 AGGGTTGGCC AGGGATGACC ACAGGCATCA TTCACACCAC TCCTTCACCG
16401 CAGGCCTGCC TGGGGTCAGT GGCGCCAGCC CCACCCAGCC CCTGGACTCA
16451 AGGGGAACTT CTCCTTCCCC CACTCAGGGT CAGGGAACTT CAAGATGCCA
16501 GTGCGTGCTC CCCATTTCAC AGATGGAAAA GAGGATGCTC TGGAGGAGAG
16551 CGGTCAGGGG GCTGGGACTC AAGCCACTCT TCCTCCCCAC TCTTCCCATT
16601 GTGACCGAGG TCTCTGAGCG TAGCAGGGAT GTCGGGGAGG CCTCTTGCTC
16651 ATGCATGGTT CGCCTCATGA CGGCCACCGT GGCAGCCACA GCCTGAGCTC
16701 CCAGGCTCCT CTTTTCAGCA GTGGATTTCA GGAGTGAAAT GGAGGCCGGG
16751 TGCGGTGGCT CACGCCTGTA ATCCCAGCAC TTTGGGAGGC TGAGGTGGGC
16801 AGATCACCTG AGTTAGGAGT TAGAGACCAG CCTGGCCAAC ATGGTGAAAC
16851 CCCATCTCTA CTAAAAATAC AAAAATTAGC CAGGCGTGGT GGCGCACATC
16901 TGTAGTCCCA GCTACTCGGG AGGCTGAAGC ACGAGAATTG CTTGAACCCA
16951 GGAGGCAGAG GTTGCAGTGA GCCTGGGCGA CAGAGCAAGA CTCTGTCTCA
17001 AAAAAAAAAA ACAGAAGAAA GAAACTGAAT AAGGCCGGGT GCGGTGGCTC
17051 ACACCTGTAA TTCCAGCACT TTGGGAGGCC AAGGAGGGCG GATCACGAGG
17101 TCAGGAGATC GAGACCATCC TGGCTAACAC GGTGAAACCC CATCTCTACT
17151 AAAAATAGAA AAAAATTAG CCGGGCGTGG TGGCGGGCGC CTGTAGTCCC
17201 AGCTACTCGA GAGGCTGAGG CAGGAGAACG GCGTGAACCC GGGAGGCAGA
17251 GGTTTCAGTG AGCTGAGACC GTGCTACTGC ACTCCAGCCT GGGCGACAGA
17301 GCGAGACTCT GTCTCAAAAA AAAAAAAAA AAAAAAAAAC AAAAAAAAAA
17351 AACAAAAAAC AACAAACAAA AAAAGAAAAT GAAACGGGAC TTGTACTCAG
17401 CGACTCCTGC TCTCTTCTGC TTATTTCCTG TGTGGTCCCC AAGCCCTGCT
17451 GAGCCCTCCT CTTCCCTGTC TCTGGGCCTT GTTGCCACTT ATACCCCTTG
17501 CCTCATTCAG GCCTCAGGCC CCTCCCCAGA CTTATCTAGC CACCTTCCCC
17551 CTGGTCTCGC TGCTGCTGGC CTCCCTCCAG TCCAGCCAAC ACATTCAGGC
17601 GGGGACAGCC CTGATAAAGC ACAACAAATC TGCCTGCATC TCTTGCCTGA
17651 AGTTTGTCTG AAGCTTCTCA AAGCCACACC TGGCGCTAG CATTCACACG
```

FIGURE 3F

```
17701 TCTCCGGGTT CTGCCACCCG CTCGTCTGGG GCCGCCTCAC TCCCTTTCCC
17751 GAGCACCAGC CAGCTGGCTT CTGTCCATTT CCTCCTCATC CTGTGGTTGC
17801 CTTCCCTCCC TGCCTCCACA GTTGTACCCC TGGTGCCTCT CTTCCTGCTA
17851 TACCCCCTGC TGAGGGGTGT CTTTCCCCTC AGCCCAGGAA TTTTAAAAGG
17901 GATGAAGCAT CTAAGACAAC AGGGGGAACC GAAGTCAACA GTCCTGAGAG
17951 TGGCTTTCTG CTCCCTACTC TTGGAAGGAT GGGCTCCCCA AGACCACTGG
18001 TGGCAAAGAA ACCTGGGGTT TGGCCGGGCG TGGTGGCTCA CGCCTGTAAT
18051 CCCAGCACTT TGGGAGGCCA AGGCAGGCGG ATCATGAGAT CAGGAGATCG
18101 AGATCATCCT GGCTAACACG GTGAAACCCC GTCTCTACTA AAAATACAAA
18151 AAATTAGCCG GGCACGGTGG CGGGCACCTG TAGTCCCAGC TACTCGGGAG
18201 GCTGAGGCAG GAGAATGGCA TGAACCTGGG AGGCGGAGCT TGCAGTGAGC
18251 CGAGATTGCG CCACTGCACT CCAGCCTGGG CCACAGAGCG AGACTCCATC
18301 TCAAAAAAAA AAAAGAACCC TGGGGTTTGG GCAGAGAGAG TTGGAGCTGA
18351 TGTGGCGCTG AGGGGGCTGC TCCCTCCCAT CTGAGTCTCC CATCTCTGCC
18401 TGCACTCTTC TGGCTGGCAC TGTGCCAGCC TGCTAACCTC CCTGGGCCTC
18451 AGTTTCCTCC TCTGTCAAAT GAGAGAGGAT CTTCTCTGGG TGTAGAAAAG
18501 GACGAGGTGG TGAGTGGGTC TGAAGGCCTC TGGTGTCCCA TAAAGCGACT
18551 CTCCTCACCA TCTTTGCCAC CCATTGGGGT GTCCAGCACC CATGGAACTC
18601 TGTCTGTGCC TCTGTCCTGG AGGGAGACTT GACCTCCTGC TCAGGAAAGG
18651 CTCTCCAAGC CCTTGTTGTG AAATTCCTGC CTGCTGTCCG GAACTCAGTC
18701 TTCCCATCCG AGGGACGAAG GTTTCGGGAA GAGAGGTGGA CAGGAAGGGG
18751 TCCTCATCAG CGGTCCCACC CTCCTCTCCT TCCTTCGCCC TCTCCAGGCC
18801 AGAAATCAGC GAGGAGCTCA AGGACCTGAT CCTGAAGATG TTAGACAAGA
18851 ATCCCGAGAC GAGAATTGGG GTGCCAGACA TCAAGGTCGG GAACTGGGG
18901 GTCTTGGGCT GGGCTGGGAC ACAGAAAACA GGAGTCACTT TCCCTTTCTG
18951 GAGGGATCAA CACCAGGATG CATGTGTGTT GGGTTTGAGT CTGTGGACTT
19001 TGGACCCCTC CAGGTGATTC TGGTAATGGC CTGACCTCTC CCCCTCTCCC
19051 TGCCCTCCCG GCCCCGACAG TTGCACCCTT GGGTGACCAA GAACGGGGAG
19101 GAGCCCCTTC CTTCGGAGGA GGAGCACTGC AGCGTGGTGG AGGTGACAGA
19151 GGAGGAGGTT AAGAACTCAG TCAGGCTCAT CCCCAGCTGG ACCACGGTGG
19201 TAAGAGAGCC GGGGTAGATG CTCCCTTGTC CTGGAGGGCC TGGGGGACCT
19251 GAGCCTTGCT CTGTGCCTGG CTCCTTGGGG GACAGAGGC CTGCCTGGCC
19301 AGCCAGCTGT GATCCTGGGC CACTGGAGCC GCCATTCTGC TGGAGGCCCA
19351 TGGAGAGGGA GGTCTTGTGG TCGGGAGACC AGGAGGCTTG GTGAGGAGAG
19401 TGACTGATTT AAAGAAATAG CGGGCGTGG GCCGGGCGCG GTGGCTCACG
19451 CCTGTAATCC CAGCACTTTG GGAGGCCAAG GCGGGCAGAT CACGAGGTCA
19501 GGAGATCGAG ACCATCCTTG AAACCCCGAC TCTACTAAAA ATATAGAAAA
19551 TTAGCTGGGC GTGGTGGCGG GCGCGTGTAG TCCCAGCTAC TCGGGAGGCT
19601 GAGGCAGGAG AATGGTGTGA ACCCGGGAGG TGGAGTTTGC CGTGAGCCGA
19651 GATCGCGCCA CTGCACTCCA GCCTGGGCCA CAGAGCGAGA CTGCGTCTCA
19701 AAAAAAAAAA AAGAAGAAAA GAAAAGAAAG AAATACCGGG CGCGGTGGCT
19751 CACGCCTGGA ATCCCAGCAC TTTGGGAGGC CGAGGCGGGT GGATCACGAG
19801 GTCAGGAGAT CGAGACCATC CTGGCTAATA CGGCGAAACC CCACCTCTAC
19851 TAAAAATACA AAAAATTAG CCGGGCGCAG TGGTGGGCAC CTGTAGTCCC
19901 AGCTACTGGG GAGGCCGAGG CAGGAGAATC GCTTGAACCT GGGAGGTGGA
19951 GGTTGTAGTG AGCCAAGATC ACGCCATTGC ACTCCAGCCT GGTTGACAGA
20001 ACGAGACTCC ATCTCAAAAA AAAAAGAAA GAAATAGATG GCCCTTGCTC
20051 AGCGGCAGCA GTCACCGTGA CTGGAAGAAG CATTTCATTC CGTCCAGACA
20101 GTTACTGAGC TTCCGTTCTC CAGGCACTGC ACAAGGTGCC GAGGACAAGG
20151 CAGGGGAACG GCCTGGGCAG CCTTTGGATT GGAGGAGTGG CCCCAAAGCC
20201 CACGTATCAG TTAGGCGGCG CCTGCGTCTC CCCCAGAGCC CACGTATCAG
20251 TTAGGCAGCA CCTGCGTCTC CCCCAGAGCC CACATATCAG TTAGACGGCG
20301 CCTGCTTCTC CCCCAGCGCC CACGTATCAG TTAGACGGCG CCTGCTTCTC
20351 CCCCAGAGCC CACGTATCAG TTAGACGGCG CCTGCTTCTC CCCCAGATCC
20401 TGTGTATCAG TTAGACTGCG CCTGCTTCTC CCCCAGAGCC CACGTATCAG
20451 TTAGACGGCG CCTGTTACTC CCCCAGAGCC CACGTATCAG TTAGACGGCG
20501 CTTGCTTCTC CCCCAGATCC CGCGTATCAG TTAGACGGGC CTGCGTCTCC
20551 CCCAGATCCC GCGTATCAGT TAGACGGGCC TGCGTCTCCC CAGAGCCCA
20601 CGTATCAGTT AGACGGGCCT GCGTCTCCCC CAGAGCCCAC GTATCAGTTA
```

FIGURE 3G

```
20651 GACGGCGCCT GCTTCTCCCC CAGAGCCCAC GTATCAGTTA GACGGGCCTG
20701 CGTCTCCCCC AGAGCCCACG TATCAGTTAG ACGGCGCCTG CTTCTCCCCC
20751 AGAGCCCGCG TATCAGTTAG ACGGTGCCTG CATCTCCCCC GTGCCCACGT
20801 ATCAGTTAGA CGGCGCCTGC TTCTCCCCCA GAGCCCACGT ATCAGTTAGA
20851 CGGGCCTGCG TCTCCCCCAG ATCCTGCGTA TCCATTAGAC AGTGCCTGTG
20901 TCTCCCCTAG TGCCCGCTCA CATTTCGGTT TTGCTCCTCT TCCTCTGCTC
20951 AGCTTCTGTG TTGGCACTTG GAAAGTGATT CACATAGTCC CCCGTGGCCA
21001 CCTGGGGCCA CTGAGAGCCC TGCCCTGCCC CTGCCTGACA GTCAAGTGAG
21051 TCAGGGCAAG CACAAGGCCA GGAGGAGAGC CAGGGCCACT GCCGTTGGCG
21101 GGGCCTGGCC TTGCACTTTA TCCCCCTCTG CAGGGTCCCG GCCCAGCTGG
21151 GACCAGCTGG CTCAATCCCT GCCCCCTATG CTTACTTGAC TCTGTGGGGT
21201 CGCTGGAACC AGGCAACTCC CACGGGGTCC CCATGACCAC TTGCCTGATC
21251 TTAGCCACCA TCTCCTCTCT CTCAGACCAC TGGAACAACC TCCCACGCTG
21301 TCCCTTGCTT CTACTCTCAC TCCCTGTCCC CCTGGTCAAT GCTCAACTCA
21351 GCACCCAGCA TGGTCCCAGT GGCATGAGTG TGTCACCTCC CAGCTCAGAG
21401 CCTGCTTCTC ACTCGGGCTG CTGTGTCCCT CAGAATCAGA CCTCCAGCCT
21451 GTGCCCCACC ACCCGCCCTG TTTTTCTGCG GGGCTCGTGC ACCGTCCCGC
21501 CATCATGCAC TCGTCTCTGG CCACGTGCCA TGGAAGGGGC TGCCCCAGAG
21551 CCTTCAGACT TCGCTTCCCT CTGCCCGGGG AGTCCCACCC CCGATGGCCA
21601 CGGGACTCGC TCCCTCACTT CCTTCGGCTT TTTACGCCAG GGTCCCCTCC
21651 TAGAGAGAAG CGAGCCTTCC CTGACCCTGT AGCTTCAGCC TCCCCTGCTT
21701 CACACCTCAT CGCCATTCCC TTGTTTTATT TTTTCCTTTC CACTTACTGA
21751 CATACATAAT TTACTGATTT TTCTTCTTTA CTTATCGCCT GTCTCCCCCA
21801 ACTAGAATAT AAGCTGTATG ATGGCTGGGC GCAGTGGCTC ACGCCTGTAA
21851 TCCCAGCACT TTGGGAGGCC AAGGCGGGAG GATCACTTGA GGTCAGGAGT
21901 TTGAGACCAG CCTGGCCAAC ATGCTGAAGC CCCGTCTCTT CTAAAAATAC
21951 AAAAAATTAG CCGGGTGTGG TGGTGGACGC CTGTAATCCA AGCTATTCAG
22001 GAGACTGAGG CGGAAGGATC ATTTGAAGCG GGGAGGCAGA GGTTGCAGTG
22051 AGCCGAGATT GTGCCACTGC ACTCCAGCCC TGGGCAACAA GAGCAAAACT
22101 CCGTCTGAAA AAAAAAAAGG CTATATGAGG GCAGGAATTC TGGCCTCAGT
22151 GTGGCCCCAG GGCCTAGAGT AGTGGCCAGC ACCCAGTAGG CAGCCAGTGG
22201 TGACCAGTGT TGACGGGATG GATGGACACA AGCGAGGGAG TGAAGGGACT
22251 GGCAAGTGTG CCGCTGCCTC TCTGCATGCG TGTGAGTCGG CGTGTCTGTG
22301 GGCACGGCAT GGAACCGTCC TTGTCACGGA GGAGGGACAA AGGCAGAGAG
22351 CCAGGCTGCG GCAGCTGTTC CCCTCCTGGC AGCCCCACTG ACTGGGCCAC
22401 CGGCTGCGGC TCAGCCGCTT CCCGGGCCGC CTGCAGTAG CATCTTGGCA
22451 TCTTCTCGGC GGCCGGAAGG CGGGAAGGAT GGCACAGCAT CCCTCCATGG
22501 CATTGCTGCC GTAGCGAGAA GGTATCTTCT AATGGACTCC CACTTCCAGC
22551 CCTGGCCCTC CCCACTCTTT CAGCCTGGCC TTGCGGACCC TTCATGGGCT
22601 GGTCCCGGCC CCCTCCTCAT GTACCAGTGG CATCCGGCTC CTCACCATTC
22651 CAGGAATATG CCCCCAGCTG CCAGCGCCCC GTGTTCTTGC CTCTGCCATT
22701 TCATGCTGTG CTGATTGAGA TGGGACCCGC ACTGCGGCCC CCTTGGCAGC
22751 TGCTCTCGGG GAATCGGAGC AGAGGCTGCG TGTCTGGGAG CCTGGGACCT
22801 GTGCTCCTCA CGCTGCCTTG TCCTCCTCAG ATCCTGGTGA AGTCCATGCT
22851 GAGGAAGCGT TCCTTTGGGA ACCCGTTTGA GCCCAAGCA CGGAGGGAAG
22901 AGCGATCCAT GTCTGCTCCA GGAAACCTAC TGGTGTAAGT ACTGGTGGGC
22951 CAGGGACTGC CGGGCACTCC CTGGAGTTGG GTGGGGAGGT CTGAGGCCCA
23001 TCCTCCCACT CTCACTGTCG TTGGGCCAAG GCCAGAGCCT GGGGACTTGG
23051 CCAGGTCTCG GTGTTGGCCC CATTTGCATC TCTGTCCCCA AGGTTAGTCG
23101 GGGCTAGAAG GGACCTTTTG GGCCCAGCTC TTGCTTCATT CCTGGGGCCA
23151 GCATCCCTCA CACACACACT TCCAGGGATG AGGAGCTCAC GCAGCCCCTC
23201 CATGGGACAG GAAGACCCTT CTTCCATGCA GCTTGATGTC ACTCTCTCAC
23251 TGGGTCCAGC CCCTCTGGGG CTTCAAATCT GTGGCCCCCT CAGCCCTTGG
23301 CAGCCTGGCA GAGGTTTGCA GACAGGCTGA TGTTGGCTTC CTGTAGGAGG
23351 CTGGCGGGCT GTAGAGGAGG GGTGCTGGCC CCTCTGCCTG GCCCTGGGGA
23401 CTGTTGGCTG CTCTCCCAAG TGGCCCAGGC TGCCTGCAGC CATTGCTGGG
23451 GCTCTGTGCC CAGTCAGCAC TTTGTGAGTG CTTGTTCAGT GAGTAAGCAG
23501 GGACAGGCTG GCCGGTGGAC CACGGGAGAG GAACCCGCAT TGGCCGAGGG
23551 CTCCCTATGG TGAGCCACGC CTGTGGGTTC ACCACCTCCT AGGAGGGTCC
```

FIGURE 3H

```
23601 AGAAAAGCAG CTCCCCAAGC CTGTGCGCCT CGTCCTCAGC AGATCCACCT
23651 TCTTCACTAT AATAAAAGCC AGTCTGGGAT GCTAATAAGG CCTGTGCTGG
23701 AGTTTGTACA CAAACCTGCA GAGAGAAAAC CAGTGGGGTC CTGAACCACA
23751 GCGTGGTCCT GGGACAGCCA CTGCCTTCCT CTGGCCCCGG AGGGAAGCTT
23801 TGGGGAAGGG GCTGGTGGGA GTTGTTTGCC CCACCCTGGC CTGCTCTGTG
23851 TGGAAGGCGC ACTCCCCAGA GGGGTGAGTG CCAGGCGCTG TCCGGGTGCC
23901 TTGGCTTCAC GCTGTCACCA GGCCTGTCCG GGACCACCAT GTTGGTTTCC
23951 CGTGAGGCCT CCCTCTCATA AGAGGGCCCT TCAGAAGGGT CGGGACCCCT
24001 CGTAGTGGAC AAGCTGACAT CTGCTCCCTG CTGGAGGTGG CTTGCACCCA
24051 GGGAGAGCCT CATAATGAGG TGGGGGGCCT GGGAGAGGCC TGGAGGTCCC
24101 AACTGCAGCT TTTCTGTCAT CTCTTCAGGG AGGTGGTTGG GGTTGGGGGA
24151 GGATTCTCTG AGCTCATCCA GGAATGTAGG CCCCTGATGC TGGAATTGTG
24201 CTTAGTGTAG GGGGAGAGGG GGCATATATA ATTTGACGTC CAAATGGGGA
24251 CATTTTTGAG AGTGAAAGGG GAAGCCATTA ATAATTATGC CAGCACGGCC
24301 GGGTGCGGTG GCTCACGCCT GTAATCCCAG CACTTTGGGA GGCCGAGGCT
24351 GGTGGATCAC AGGGTCAGGA GATCGAGACC ATCCTGGCTA ACACGGTGAA
24401 ACCCCGTCTC TACTAAAAAT ACAAAAAATC AGCTGGGCGT GGTGGCGGGC
24451 ACCTGGAGTC CCAGCTACTC AGGAGGCTGA GGCAGGAGAA TGGCGTGAAC
24501 CCGGGAGGCA GAGCTTGCAG TGAGCCAAGG TCACGCCACT GCACTCCAGC
24551 CTGGGCGACA GAGTGAGACT CCGTCTCAAA AAATAATAAT TATTATGCCA
24601 GCATGGTGGC TCATGCCTAT AATCCCAGCA CTTTGGGAGG CCAAGGCAGG
24651 ATTGCTTGAG GCCAGGAGTT CAAGACCAGC CTGGGCAACA TAGCAAGACC
24701 CCATCTCTAA AAAAAAAAA AATTAGCCGG GCGTGGTGG GGGTGCCTGT
24751 AGTCCCAGCA ACTCAGGAGG CTGAGGTGGG AGGATTGCTT GAGTCTGGGA
24801 GGTGGAGGTT GCAGTGAGCT GAGATTGCAC CACTGTACTC CAGCCTGGGT
24851 GACAGAGCCA GACCCTGTCT CAAAAAAAAA AAAGAAAAAA AAGTAATAAT
24901 AATTATGCCA GGACAGCAGG TGGACGGACA CCTGGTCCTT CTGACTCAGA
24951 GCCTGTGGTC CAGCACCCCC TAGTGGTGGA ACAAGCCAGA CACAGGATAA
25001 GGATACATTT AGTGTCTAGT TTGTACCTGG CAAACAGAGT GACAAGATTG
25051 GGCTTAATAC TTTCCAGCTA TAAATTCTA GAATTCTGTG ACCCAAGTTT
25101 AATTTGGGGT AGAGCTTTTT AAAAAAAAAA TAGAGATGGA GTCTTGCCAT
25151 GTTGCCCAGG CTGGACTTAA ACTCCTGGCC TCAAGCCATT TGCCCACCTT
25201 GGCCTCCGAA AGTGCCAGGT GATTACAGGC ATGAGCCACC ACACCCAGCC
25251 TCCACGTTTA ACTTTGAAAG AAGATTTTAC TTCATCATCA AGTCCCAATA
25301 TTTATCCTTG ATAGACTGCT TTGGTTTTTT GTTTGTTTGT TTTGAGATGG
25351 AGTTTCACTC TTGTTGCCCA GGCTGGAGTG CAGTGGCGCA AACTCAACTC
25401 ACTGCAGTCT CCGCCTCTCA CATTCAAGCA GTTCTCTTGC CTCAGCCTCC
25451 CAAGTAGCTG GGATTACAGG TGCATGCCAC CACCACACCG GCTAATTTTT
25501 GTATTTTTAT TAGAGACGGG ATTTCACCAT TTTGGCCAGG CTGGTCTCAA
25551 ACTCCTGACC TCAGGTAATC TGCCCACCTC AGCCTCCCAA AGTGCTGGGA
25601 TTACAGGCGT GAGCCACTGT GCCCGGCCAT AGAGTTTTTT ATACTTTGGG
25651 ATAATTGTAG AAAACTCAGTA GTAGAGTTAA GTGGAGTTGG TCCTTTTTAA
25701 AGATATCAAA ACCCATTTAC TGGTTATTTT AAAAAGAGAC ATTTTGGGAG
25751 GAAAACTAGA TATAGAAATC TGTTGAATAT GTGACAGAAT CCCAAGACTG
25801 ATAGATGGAC TCTGCCCTGT GAACAAGGCA AAGAAAAATG CAAAATGAAA
25851 GCCTCTCTAC CCAGATCTGC TGGGGATGA CTGAGGTCAA CACAGAAGGC
25901 CCTCAGGCCG GGCACGGTGG CTCACGCCTG CAATCCCAAC ACTTTAGGAG
25951 GCTGAGGTGG ATGGATCGCT TGAGCCCAGG AGTTTGAGAC CAGCCTGGGC
26001 AACATGGTGA AACCCTGTTT TTATAGAGAT AAAAAAATAC AAAAATTAGC
26051 TGGGCGTGGT GGCATGTGCC TGTAGTCTCA GCTACTCAGG AGGCTGAGGT
26101 GGGAGGATCG CTTGAGCCTG GAAGGCAGAG GTTGCAATGA GCTGAGATTG
26151 CACCACTGCA CTGCAGCCTG CACGACAGAG CGAGACGCTG TCTCAAAACA
26201 ACAACAAAAC CACACACACA GAGAGAAGGC CCTTGATTAG GCTGATAGTT
26251 GGAGGATGTA GGGAAGTCAG CTGGGTCAGA CTGTGAGCAG CTCCAGAGGC
26301 CGTGCTGGGA GGTTTAGACT TCATCTCTGG TCAATGGGGG GCCACGGAGG
26351 CGTTGCGGGC TGAGACTGGG GGCTGAGAGA CCGGCAAGGA GCAACTGCCG
26401 TGATGTAGGG AGGCCAGAGG GAGGCCAAGC TTGGGGCAGT GGGTGAAGGG
26451 GGCTTTGAGA GATGTGGGAT TCAGATTCCT GTGTGTGTGA GGGAGAGTGT
26501 CTCCCTGAGT GCATATTCTG ACCCTGAGGT CCCTCTGTCC CTGGTGTCCC
```

FIGURE 3I

```
26551 CTGAACAGGA AAGAAGGGTT TGGTGAAGGG GGCAAGAGCC CAGAGCTCCC
26601 CGGCGTCCAG GAAGACGAGG CTGCATCCTG AGCCCCTGCA TGCACCCAGG
26651 GCCACCCGGC AGCACACTCA TCCCGCGCCT CCAGAGGCCC ACCCCCTCAT
26701 GCAACAGCCG CCCCCGCAGG CAGGGGGCTG GGGACTGCAG CCCCACTCCC
26751 GCCCCTCCCC CATCGTGCTG CATGACCTCC ACGCACGCAC GTCCAGGGAC
26801 AGACTGGAAT GTATGTCATT TGGGGTCTTG GGGGCAGGGC TCCCACGAGG
26851 CCATCCTCCT CTTCTTGGAC CTCCTTGGCC TGACCCATTC TGTGGGGAAA
26901 CCGGGTGCCC ATGGAGCCTC AGAAATGCCA CCCGGCTGGT TGGCATGGCC
26951 TGGGGCAGGA GGCAGAGGCA GGAGACCAAG ATGGCAGGTG GAGGCCAGGC
27001 TTACCACAAC GGAAGAGACC TCCCGCTGGG GCCGGGCAGG CCTGGCTCAG
27051 CTGCCACAGG CATATGGTGG AGAGGGGGGT ACCCTGCCCA CCTTGGGGTG
27101 GTGGCACCAG AGCTCTTGTC TATTCAGACG CTGGTATGGG GGCTCGGACC
27151 CCTCACTGGG GACAGGGCCA GTGTTGGAGA ATTCTGATTC CTTTTTTGTT
27201 GTCTTTTACT TTTGTTTTTA ACCTGGGGGT TCGGGGAGAG GCCCTGCTTG
27251 GGAACATCTC ACGAGCTTTC CTACATCTTC CGTGGTTCCC AGCACAGCCC
27301 AAGATTATTT GGCAGCCAAG TGGATGGAAC TAACTTTCCT GGACTGTGTT
27351 TCGCATTCGG CGTTATCTGA AAAGTGACT GAACGGAATC AAGCTCTGAG
27401 CAGAGGCCTG AAGCGGAAGC ACCACATCGT CCCTGCCCAT CTCACTCTCT
27451 CCCTTGATGA TGCCCCTAGA GCTGAGGCTG GAGAAGACAC CAGGGCTGAC
27501 TTTGACCGAG GGCCATGGAC GCGACAGGCC TGTGGCCCTG CGCATGCTGA
27551 AATAACTGGA ACCCAGCCTC TCCTCCTACA CCGGCCTACC CATCTGGGCC
27601 CAAGAGCTGC ACTCACACTC CTACAACGAA GGACAAACTG TCCAGGTCGG
27651 AGGGATCACG AGACACAGAA CCTGGAGGGG TGTGCACGCT GGCAGGTGGC
27701 CTCTGCGGCA ATTGCCTCAC CCTGAGGACA TCAGCAGTCA GCCTGCTCAG
27751 AGCGGGGGTG CTGGAGCGCG TGCAGACACA GCTCTTCCGG AGCAGCCTTC
27801 ACCTTCTCTC TGGGATCAGT GTCCGGCTGG CCGACGTGGC ATTTGCTGAC
27851 CGAATGCTCA TAGAGGTTGA CCCCCACAGG GTCACGCAGG ACTCGGACAC
27901 TGCCCTGGAA ACATGGATGG ACAAGGGCTT TTGGCCACAG GTGTGGGTGT
27951 CCTGTTGGAG GAGGGCTTGT TTGGAGAAGG GAGGCTGGCT GGGGGAGAAA
28001 CCCGGATCCC GCTGCATCTC CGCGCCTGTG GGTGCATGTC GCGTGCTCAT
28051 CTGTTGCACA CAGCTCACTC GTATGTCCTG CACTGGTACA TGCATCTGTA
28101 ATACAGTTTC TACGTCTATT TAAGGCTAGG AGCCGAATGT GCCCCATTGT
28151 CAGTGGGTCC ACGTTTCTCC CCGGCTCCTC TGGGCTAAGG CAGTGTGGCC
28201 CGAAGCTTAA AAAGTTACTC GGTACTGTTT TTAAGAACAC TTTTATAGAG
28251 TTAGTGGAAG GCAAGTTAAG AGCCAATCAC TGATCCCCAA GTGTTTCTTG
28301 AGCATCTGGT CTGGGGGGAC CACTTTGATC GGACCCACCC TTGGAAAGCT
28351 CAGGGGTAGG CCCAGGTGGG ATGCTCACCC TGTCACTGAG GGTTTTGGTT
28401 GGCATCGTTG TTTTTGAATG TAGCACAAGC GATGAGCAAA CTCTATAAGA
28451 GTGTTTTAAA AATTAACTTC CCAGGAAGTG AGTTAAAAAC AATAAAAGCC
28501 CTTTCTTGAG TTAAAAAGAA AAAAAAAAGG TTTGTGCGTA CATTTTCTGC
28551 ATCTGGATAT ACGTTCTTTC TCAGCAGCTG GAACAGCTGG CTTTGTTGAA
28601 TTTTCTGGAA GCGTCTGAGG CACCCTAAGT CCCTGAGCAG GACAGTGGTG
28651 AGAAGTGGTC TTGGCGGAGG GAGGGAGAGG GAAGGGCTGG CTCAGGAGGT
28701 GACCGGGCTG CAGTCCAGGG TACAGCTGAG GCTCCTGGGC GGGTCCGTGG
28751 CCACTCCTTG GGAAGAACTG CCTGTTTCAC AGGGGCTCAG GATGCCAAGG
28801 TCTGGTCCGG GTAGGAGCCA TAGCTGCTGC TTTTGGGGCA GAGGTCCCTG
28851 TGGTGTCACA GGAGTGCCTG TGACACCAGC CCAGTGACCT CCCATCCCCG
28901 CTTAGCCTTG GACACTGGTA CAGACTTTTG GGACCCCACA CCTCTGTTCC
28951 CATGGTACAG CCCTCCAGGG CAGCGACGAA AAGAGTCATC CTTAAGGTCA
29001 CACAGCCCTG AGCTTGAATC CAAGCTTTGC TACTTAAAAA TTGTGTGACC
29051 TTTGGCAGGT CATTGGAGGA GCCTCAGTTC CCTTATTGAT TTAATGGGAA
29101 TGTTCCCGTG GGGTGTTTTG TTTGTTTGTT TGAGATTTTT TGAGACTTGC
29151 TCTGTCACCC AGGCTGGAGT GCAATGGCAA GATCTCGGCT CACTGCAACC
29201 TCTTCCTCCT GGGTTCAAGC GATTCTCCTG CCTCAGCCTC CCAAGTAGCT
29251 GGGACTACAG GTGCCCGCCA CCATGCCCCA GCTAATTTTT TGTACTTTTA
29301 GTAGAGACGG GGTTTCACCA TGTTGGCCAG GCTGGTCTTG AACTCCTGAC
29351 CTCAGGTGAT CTGCCCACCT CGGCCTCCCA AAGTGCTGGG ATTACAGGCG
29401 TGAGCCACCG CGCCCACCTC CCCATGGGGT TTGAATGCAA ACAATGCAAA
29451 CGTTTTCGTC TGCTCTCACA CTACAACAGT GAACACAGAA GACTTCTGTG
```

FIGURE 3J

```
29501 ACCGGCTGGG CGCGGTGGCT CACGCCTGTA ATCCCAGCAC TTTGGGAGGC
29551 TGAGGAAGGC GGATCATGAG GTCGGAGATC GAGACCATCC TGGCTGACAC
29601 GGTGAAACCC CGTCTCTACT AAAAATACA    (SEQ ID NO:3)
```

FEATURES:
Start:   3000
Exon:    3000-3359
Intron:  3360-4259
Exon:    4260-4307
Intron:  4308-4749
Exon:    4750-4803
Intron:  4804-5206
Exon:    5207-5258
Intron:  5259-5511
Exon:    5512-5645
Intron:  5646-6122
Exon:    6123-6159
Intron:  6160-7038
Exon:    7039-7060
Intron:  7061-8252
Exon:    8253-8341
Intron:  8342-12264
Exon:    12265-12464
Intron:  12465-15226
Exon:    15227-15280
Intron:  15281-16061
Exon:    16062-16135
Intron:  16136-18797
Exon:    18798-18885
Intron:  18886-19070
Exon:    19071-19199
Intron:  19200-22830
Exon:    22831-22934
Intron:  22935-26558
Exon:    26559-26628
Stop:    26629

CHROMOSOME MAP POSITION:
Bac accession number: AC005940
Chromosome: 17

ALLELIC VARIANTS (SNPs):

| DNA Position | Major | Minor | Domain | Protein Position | Major | Minor |
|---|---|---|---|---|---|---|
| 2082 | G | A | Beyond ORF(5') | | | |
| 2748 | - | C A | Beyond ORF(5') | | | |
| 8868 | G | A | Intron | | | |
| 10187 | G | A | Intron | | | |
| 10216 | T | C | Intron | | | |
| 11100 | G | A | Intron | | | |
| 11650 | G | A | Intron | | | |
| 11656 | A | C | Intron | | | |
| 15095 | C | T | Intron | | | |
| 15116 | A | G | Intron | | | |
| 15428 | A | G | Intron | | | |
| 15827 | T | C | Intron | | | |
| 16135 | G | A | Exon | 375 | G | E |
| 16557 | A | G | Intron | | | |

FIGURE 3K

| | | | | |
|---|---|---|---|---|
| 17375 | C | T | G | Intron |
| 17375 | G | C | | Intron |
| 17375 | A | C | G | Intron |
| 17375 | A | C | G | Intron |
| 17511 | C | T | G | Intron |
| 17928 | A | C | | Intron |
| 17968 | C | G | | Intron |
| 18574 | T | C | | Intron |
| 19654 | C | T | | Intron |
| 21498 | C | T | | Intron |
| 22729 | G | A | | Intron |
| 22757 | C | T | | Intron |
| 22779 | C | T | | Intron |
| 24350 | T | G | | Intron |
| 24558 | T | C | A | Intron |
| 24872 | - | A | | Intron |
| 25756 | C | T | | Intron |
| 25968 | G | A | | Intron |
| 26537 | G | C | | Intron |
| 28204 | C | T A G | | Beyond ORF(3') |

Context:

DNA
Position

2082
ATGCAGAGTCCAGCGCAAGCAGGGGGAAGGGCATCAGGTTGGGCATGGCCAGCGCTCTAC
AAGCCTGGGACAGAGATGGGGGTCTCAGGCTGAGTGTCAGGGTTCAGTCCGGGGTCAGGA
TGTAGCCCAGGGTCATGGCTGAAGGTGAGGGCTGGGGGTCACCTCCCTGATGTTTCAGCC
GCCACACAGTGAGTTTGAGAACATGAGTCTCAGGGGATGTCATGCCCCTGTTTCACCCCT
CATTCCCCTCATTCCCCATCCCCTTGCTTTTTTTTGAAACCGAGTCTTGCTCCATCACCCA
[G,A]
GCTGGAGTGTAGTGGCGTGATCTTGGCTCACTGCAACCTCCACCTCCCAAGTTCACACGA
TTCTCCTGCCTCAGCCTCCCGAGTAGATGGGATTTCAGGTGCACGCCACCATGCCTGGCT
AATTTTTTGTATTTTTAATAGAGACAGAGTTTTGCCATGTTAGCCAGGCTAGTCTCGAACT
TCTGACCTCAGGTGATCCACCTGCCTCGGCCTCCCAAAGTGCTGGGATTACAAGTGTGAG
CCACCATGTGGGGCCCATCCCCTTGTTTTGACAGACGTCAATGAGGCAGGGCTGGCTGGA

2748
CAAGGAGGGCTCCCTGGAGGAGGCGGGTGGGTCTGAAGCATCAGCAAGGCTTCTGAGTTA
CTAGTGTCTAGCTCAGCTTCCAGGAGGCAGTGTCGGAGTGCTCTGCTGTCAAGGGTTGGG
ACTCATGACTCACAGGGCTGCATGCTGTGCTGGGGCTGAGCTGACCCTGGGCTCTGCCCC
TTCCAGTGCTGCTGGGCCTCCAGGCTTCTGCCCTGTCTGTCCTGATTCCAGAATATCAGA
TTCTCTCTGCTTCCCTGTGAAGCCAGCAGGCAGAAGTGACTGCCTCTGTTACCGGCAGGG
[-,C,A]
TACTGAGGCCTAGAGGGCTGGCATGCCGGCAGAACCGATGTGAATTCATTCAGGTCATAGG
GACAGACTTGAGTTTGGGTGTTGGCAATCCCGGTAGAGGGAACAGCCAGGGCAAAGGCAT
GGAGGTGGGACCCACAGCGCTGTGGCTACCTTACCTGGTAGCCAGCCTGACACCCAGGAG
TGAAGCCTTCTCTGCCTTCTTTTCTCAGGTTCCCAACAAGGCTACGCAGAAGAACCCCCT
TGACTGAAGCAATGGAGGGGGGTCCAGCTGTCTGCTGCCAGGATCCTCGGGCAGAGCTGG

8868
TCCTGTGGGTCTGAGTCCTGGCTGTTCTGTATCTTTCTTCTGCTGAGTTCTTAGCCTAGC
TTAGCGTTGCCACGGGGCTTCAAGAGATGTGGGAAGGAAGGGATTTATGTCCAGCTGCTG
GGGAGAGTCTGTCCTGGCATGGGGCCGGGGCATGGTGGCAGGGTGGATTTACCTGTGAGG
GGCCCTAGTCTGATAAGAGCTCAGGAGGGTGATGTGAGCTTGGCCTCTGTCTCATTTCAT
TCATTAGCTACATTCACTTGCCTGGGGGCATAGGGGTGAAAGACCCAGACCCGAGTTCAC
[G,A]
GCCTAGTGGGAGGGACAGGAATCTAGGCAGGCAGATAATACAGCGTGGTGCCTGCCAAGG
CTGGGGAGCCTAGAGGCTGTAGGAGTGCCGGGGGGCTGGGGAAGTCTCCCTGAAGAGGCT
ACTTATGATTCGGGTCCTGAGGGATGAGTAGACTTCCCTGCTCAGGTTTTGAGGGATGGG
CGTGGAAGACGATGTGCCTGGCATAGGCGTGTACTCTGAGTCTGGGGAGAAGTGGAGTCT

FIGURE 3L

```
         GGCTGAAGCCTCCAGTGGGCAGAGGAGGGCCGTGGTTAGTGAAAGATGATGCTGGAAACA
10187    TTCCCTGGGGGAACAGGGTGGGGATCTGGCTGAGGTTTGACCTGCAGTGACAGAAACAGG
         ACTGTCTTTATCCTGCTCGAGCCTCTCCTTTGCCTTCAGATTAAGACTCTCTTTGCACAT
         ATGGGGAAACTGAGGCACACAGAGGGGAGGGCTTTGCAGAAAATCCCTACCAAGGGCCTA
         GAGGCATGGGATGGGAAGGGGACATTTTACCCCGGTACGGTCAGTGGCAGGCAC
         [G,A]
         GTCCTGTACCAGCTTGGCTCCACCTCCTTTCTGTTGTAGTCCCTTCTTTCCCCTGAAGTC
         CTGTTGTCTGCTATCCCCTAGCCTCCACAAAGAAACGAGTTTATCTTACCTGGTTCTTGG
         GTAAAGCCTCATCAGGACCCAGCTAATCACAGTGAAGGGCTTCCCTGGGGCAGAACGGTT
         AGCGCCAGGGGCTGGACAGGTGGATGAACAGAGGCACGAGGGCGCTGAAGACCTGCCTTG
         TGATTCTGGCCCCAAGAAGAGAGAGTTGAGGCTGCCATGAGAGGGCTCGGTGGTCAGGGC
10216    TTCCCTGGGGGAACAGGGTGGGGATCTGGCTGAGGTTTGACCTGCAGTGACAGAAACAGG
         ACTGTCTTTATCCTGCTCGAGCCTCTCCTTTGCCTTCAGATTAAGACTCTCTTTGCACAT
         ATGGGGAAACTGAGGCACACAGAGGGGAGGGCTTTGCAGAAAATCCCTACCAAGGGCCTA
         GAGGCATGGGATGGGAAGGGGACATTTTACCCCGGTACGGTCAGTGGCAGGCACAGTCCT
         GTACCAGCTTGGCTCCACCTCCT
         [T,C]
         TCTGTTGTAGTCCCTTCTTTCCCCTGAAGTCCTGTTGTCTGCTATCCCCTAGCCTCCACA
         AAGAAACGAGTTTATCTTACCTGGTTCTTGGGTAAAGCCTCATCAGGACCCAGCTAATCA
         CAGTGAAGGGCTTCCCTGGGGCAGAACGGTTAGCGCCAGGGGCTGGACAGGTGGATGAAC
         AGAGGCACGAGGGCGCTGAAGACCTGCCTTGTGATTCTGGCCCCAAGAAGAGAGAGTTGA
         GGCTGCCATGAGAGGGCTCGGTGGTCAGGGCGGCCCAGGCCTGGTTCTCAGTTGATGGGG
11100    ATCGATGCCTAGCTGCCTAGTTATCTACCAAGATGTCTATTGGAAATCTATGTGGGTAAA
         GAGCTGGAGTTCAAGGGAGAGGCTAGGGTTTGAGATAAGAACATGAGACCACTTTCCATG
         GTCAAATGTCCACCCCCCTGAGCTTCTGTGCCCTGAAGGGTGTGTCAGATTCCTTGTGTG
         TGCCTGGCACATAGTAGGCAATCAAGAAAGTGCCACTGGTTTTATGGTTATTGTTATACG
         GCACCCGCCTTCTCTGCCCGCAGCCTCCCTCTCCTCTTCTCCCTTCCTCTTTCTTCTCTC
         [G,A]
         CCTTCTCTCCTCCCTCCTCTCCAGCATCCTGGGGTCCGTTGGTCCAGATGAAGGTACTTG
         CCAAGGAGGGAGCCCACAGGTCGATGGTCGCGGGATGGGGTCAGTGGGGTCATTGTCTCT
         CTTGGCTGGGACCTTACCAGTCATGTCAGCTTGAGCCACCTGTCACTTCGTGGTGGTGCT
         GGGCCCAGAAAGCAGGGCAGACCTCCAGCCTATTAGGTCATTTCTGATTTGGGATTCGTC
         CTACTATATGTGGCTGACCTTACACCCCAGCTGTGTCATCCTGCTTGTCCCAAGGCCTGG
11650    GTGGCTGACCTTACACCCCAGCTGTGTCATCCTGCTTGTCCCAAGGCCTGGGGTGCCATC
         CATCTCTCTGAAACCCCATCAGCCCAGATCCCGAGGGCTGAGATGGTACCTCTGTAGGAT
         AGCAGAGTCCCTACAATCTTACTCTCAGTCCCAGCAGCAGGGACATCTTTGCCTAGCCTG
         GGTGGGGGATGGAACTGGAGAAAGGTTTTGATTGGCTTTGGGCCTGCAGACGGCACTCAC
         AGGGAAGGGGCAGAGCTAGCCTAGGAAGAACTCTGCTCCCAGCTGGGGGCGGTGGCTCAC
         [G,A]
         CCTGTAATCCCAGCACTTTGGGAGGCCGAGGTGGGTGGATCACCTGAGGTCAGGAGTTCA
         AGACCAGCCTGACCAACATGGCGAAACCCTGTCTCTACTAAAAATACAAAAAGTAGCCGG
         GCGTGGTGGCAGACACCTGTAATCCCAACTACTCGGGAGGCTGAGGCAGGAGAATCTCTT
         GAACCTGGGAGGTGGAGGCTGCAGTGAGCCGAGATCACGCCATTGCACTCCAGCCTGGGG
         ACAGAGTGAGACTCTGTCTCAAAAAAAAAAAAAAAAAACCAAAAAAAAAAACAGCAACA
11656    GACCTTACACCCCAGCTGTGTCATCCTGCTTGTCCCAAGGCCTGGGGTGCCATCCATCTC
         TCTGAAACCCCATCAGCCCAGATCCCGAGGGCTGAGATGGTACCTCTGTAGGATAGCAGA
         GTCCCTACAATCTTACTCTCAGTCCCAGCAGCAGGGACATCTTTGCCTAGCCTGGGTGGG
         GGATGGAACTGGAGAAAGGTTTTGATTGGCTTTGGGCCTGCAGACGGCACTCACAGGGAA
         GGGGCAGAGCTAGCCTAGGAAGAACTCTGCTCCCAGCTGGGGGCGGTGGCTCACGCCTGT
         [A,C]
         ATCCCAGCACTTTGGGAGGCCGAGGTGGGTGGATCACCTGAGGTCAGGAGTTCAAGACCA
         GCCTGACCAACATGGCGAAACCCTGTCTCTACTAAAAATACAAAAAGTAGCCGGGCGTGG
         TGGCAGACACCTGTAATCCCAACTACTCGGGAGGCTGAGGCAGGAGAATCTCTTGAACCT
         GGGAGGTGGAGGCTGCAGTGAGCCGAGATCACGCCATTGCACTCCAGCCTGGGGGACAGA
```

FIGURE 3M

```
        GTGAGACTCTGTCTCAAAAAAAAAAAAAAAAAAAACCAAAAAAAAAAACAGCAACAACTCTC
15095   GGCTGTTTGCAATATCAGGAAGAAGGTGGATTATGAGGAGAAGGGATGACTCCTTGAAGC
        CCGAGCTGGTTTAGTGAGCAGAAGTTCCATATATACCATCATTCCTGGGGTGCGTCTGTG
        GCACGGGAGCGGCCCGTGTGACCCTCTGGATGAAGGAGGTTTTGTACCTGTTGAGTTGGA
        AACGTACCTGGTTAGAGTCTTTCCCAAGGAAACCCAGAACCCCTGGAGGGTGGAGGCCTT
        GTTCTGGCCGCCCCTGTGTCCTCAGCACTCAGCACGGGGCCCAGCATCGGGCAAGTACCG
        [C,T]
        GGAGTGTTTGTCGAGTGAGTACATGACAGAGGAAAGAGGTTCCCTGCAGGCCTCTCCTGC
        AGCCCGCTGGAGCTGGGTGGGCAGAGGTGGCTGTGCCTGTTGGGGACTGATGTGAGCATG
        TTTCTTTCCAGGCCTTGGATGTATGGGCCACTGGCGTCACGTTGTACTGCTTTGTCTATG
        GGAAGGTGAGTGCCAGGGATGCCAGCAGAGCTGGGGCGGGTCCAGTGAGGCGGGCACGGG
        CGACGGATGCAGGCTCTTCCTTTTTGTCCTTAAGTGGCTTTTGAAAGAGCCCACCTGGCT

15116   GAAGGTGGATTATGAGGAGAAGGGATGACTCCTTGAAGCCCGAGCTGGTTTAGTGAGCAG
        AAGTTCCATATATACCATCATTCCTGGGGTGCGTCTGTGGCACGGGAGCGGCCCGTGTGA
        CCCTCTGGATGAAGGAGGTTTTGTACCTGTTGAGTTGGAAACGTACCTGGTTAGAGTCTT
        TCCCAAGGAAACCCAGAACCCCTGGAGGGTGGAGGCCTTGTTCTGGCCGCCCCTGTGTCC
        TCAGCACTCAGCACGGGGCCCAGCATCGGGCAAGTACCGCGGAGTGTTTGTCGAGTGAGT
        [A,G]
        CATGACAGAGGAAAGAGGTTCCCTGCAGGCCTCTCCTGCAGCCCGCTGGAGCTGGGTGGG
        CAGAGGTGGCTGTGCCTGTTGGGGACTGATGTGAGCATGTTTCTTTCCAGGCCTTGGATG
        TATGGGCCACTGGCGTCACGTTGTACTGCTTTGTCTATGGGAAGGTGAGTGCCAGGGATG
        CCAGCAGAGCTGGGGCGGGTCCAGTGAGGCGGGCACGGGCGACGGATGCAGGCTCTTCCT
        TTTTGTCCTTAAGTGGCTTTTGAAAGAGCCCACCTGGCTCAGAGAAGGCTGAGAGAGAAG

15428   AAAGAGGTTCCCTGCAGGCCTCTCCTGCAGCCCGCTGGAGCTGGGTGGGCAGAGGTGGCT
        GTGCCTGTTGGGGACTGATGTGAGCATGTTTCTTTCCAGGCCTTGGATGTATGGGCCACT
        GGCGTCACGTTGTACTGCTTTGTCTATGGGAAGGTGAGTGCCAGGGATGCCAGCAGAGCT
        GGGGCGGGTCCAGTGAGGCGGGCACGGGCGACGGATGCAGGCTCTTCCTTTTTGTCCTTA
        AGTGGCTTTTGAAAGAGCCCACCTGGCTCAGAGAAGGCTGAGAGAGAAGAGGCTTTTTCT
        [A,G]
        TCTTTCTCTGGTCCCCTGCGGAGCGATTCTCGCGAAGGAGTCGCAGGACAGCAGACACCT
        AAGGGGAGGTGCCGACGATGGTGTTGCCACCGCCCCAGCCAGAGTGCTCCCCGTCCCTCT
        GTCCCTTGACGCCATTCACTTATTGAGCCATGTGTTCACTCCCTTGCTCATTTATTCGAC
        AAATTGTCCTTCACCCCTACCCTGGCTGAGGCTGGACCCTGGGGACACCCAACGCTGACG
        TATCGGTGATCCCTGCCCGCAGGTGTGCCTGCTCTGGTGACCACACTAAGGGGCAGGGGG

15827   CCAGAGTGCTCCCCGTCCCTCTGTCCCTTGACGCCATTCACTTATTGAGCCATGTGTTCA
        CTCCCTTGCTCATTTATTCGACAAATTGTCCTTCACCCCTACCCTGGCTGAGGCTGGACC
        CTGGGGACACCCAACGCTGACGTATCGGTGATCCCTGCCCGCAGGTGTGCCTGCTCTGGT
        GACCACACTAAGGGGCAGGGGGAATTTCAGTGAACATGTTCCCAAGCCCCAGGCCCTGG
        GAGTGGAGGCCTGGCCACAGGTGGCGGTAATGGTGGTGGGTGCACCCAGCCTGGCCTGGC
        [T,C]
        TGGCCGCGGGTGGCAGTAACGGCGGTGGATGCACCCAGCCTCATTGTTCCCTCAGCAACT
        CATTCATTCAGTCAACATTTGTTGAACATTTACAGTGTGAGTTGAGGTCCTTCTCATGTA
        ATGGGAGCCCAGACCTGCCCCCTACCCCTGCCCCCACCAAGGGAGGGGGGTTGATCCCCT
        GGCACAGGTCGAGGCCCTGGACCCACATCCTTTGTCTGCCTCTCCACCCCACAGTGCCCG
        TTCATCGACGATTTCATCCTGGCCCTCCACAGGAAGATCAAGAATGAGCCCGTGGTGTTT

16135   GGGTGGCAGTAACGGCGGTGGATGCACCCAGCCTCATTGTTCCCTCAGCAACTCATTCAT
        TCAGTCAACATTTGTTGAACATTTACAGTGTGAGTTGAGGTCCTTCTCATGTAATGGGAG
        CCCAGACCTGCCCCCTACCCCTGCCCCCACCAAGGGAGGGGGGTTGATCCCCTGGCACAG
        GTCGAGGCCCTGGACCCACATCCTTTGTCTGCCTCTCCACCCCACAGTGCCCGTTCATCG
        ACGATTTCATCCTGGCCCTCCACAGGAAGATCAAGAATGAGCCCGTGGTGTTTCCTGAGG
        [G,A]
        GTGAGTTGTCCACCCAGGGGAACAAGGGGGCTACCACCCGCTCCTGGTGTCTGAGTTTTA
        GCAGAGCTTTTGCCCTCTGAGGACCCCACCCCAGCCTGCAGATATGAAGGTGGCGGTGCT
        GTTCCCTGGGAGGGACCCCTGAATAGATGGACGGGAGGGACTCTGGAGCCAAGGGTCTCC
```

FIGURE 3N

```
              GCAACGTCACTGTGTGGATGGGAACCCTGAGATCCAGGGTTGGCCAGGGATGACCACAGG
              CATCATTCACACCACTCCTTCACCGCAGGCCTGCCTGGGGTCAGTGGCGCCAGCCCCACC

16557   TTCCCTGGGAGGGACCCCTGAATAGATGGACGGGAGGGACTCTGGAGCCAAGGGTCTCCG
              CAACGTCACTGTGTGGATGGGAACCCTGAGATCCAGGGTTGGCCAGGGATGACCACAGGC
              ATCATTCACACCACTCCTTCACCGCAGGCCTGCCTGGGGTCAGTGGCGCCAGCCCCACCC
              AGCCCCTGGACTCAAGGGGAACTTCTCCTTCCCCCACTCAGGGTCAGGGAACTTCAAGAT
              GCCAGTGCGTGCTCCCCATTTCACAGATGGAAAAGAGGATGCTCTGGAGGAGAGCGGTCA
              [A,G]
              GGGGCTGGGACTCAAGCCACTCTTCCTCCCCACTCTTCCCATTGTGACCGAGGTCTCTGA
              GCGTAGCAGGGATGTCGGGGAGGCCTCTTGCTCATGCATGGTTCGCCTCATGACGGCCAC
              CGTGGCAGCCACAGCCTGAGCTCCCAGGCTCCTCTTTTCAGCAGTGGATTTCAGGAGTGA
              AATGGAGGCCGGGTGCGGTGGCTCACGCCTGTAAT

17375   GAGGCCAAGGAGGGCGGATCACGAGGTCAGGAGATCGAGACCATCCTGGCTAACACGGTG
              AAACCCCATCTCTACTAAAAATAGAAAAAAAATTAGCCGGGCGTGGTGGCGGGCGCCTGT
              AGTCCCAGCTACTCGAGAGGCTGAGGCAGGAGAACGGCGTGAACCCGGGAGGCAGAGGTT
              TCAGTGAGCTGAGACCGTGCTACTGCACTCCAGCCTGGGCGACAGAGCGAGACTCTGTCT
              CAAAAAAAAAAAAAAAAAAAAAAAAACAAAAAAAAAAAACAAAAACAACAAACAAAAAAA
              [C,T,G]
              AAAATGAAACGGGACTTGTACTCAGCGACTCCTGCTCTCTTCTGCTTATTTCCTGTGTGG
              TCCCCAAGCCCTGCTGAGCCCTCCTCTTCCCTGTCTCTGGGCCTTGTTGCCACTTATACC
              CCTTGCCTCATTCAGGCCTCAGGCCCCTCCCCAGACTTATCTAGCCACCTTCCCCCTGGT
              CTCGCTGCTGCTGGCCTCCCTCCAGTCCAGCCAACACATTCAGGCGGGGACAGCCCTGAT
              AAAGCACAACAAATCTGCCTGCATCTCTTGCCTGAAGTTTGTCTGAAGCTTCTCAAAGCC

17375   GAGGCCAAGGAGGGCGGATCACGAGGTCAGGAGATCGAGACCATCCTGGCTAACACGGTG
              AAACCCCATCTCTACTAAAAATAGAAAAAAAATTAGCCGGGCGTGGTGGCGGGCGCCTGT
              AGTCCCAGCTACTCGAGAGGCTGAGGCAGGAGAACGGCGTGAACCCGGGAGGCAGAGGTT
              TCAGTGAGCTGAGACCGTGCTACTGCACTCCAGCCTGGGCGACAGAGCGAGACTCTGTCT
              CAAAAAAAAAAAAAAAAAAAAAAAAACAAAAAAAAAAAACAAAAACAACAAACAAAAAAA
              [G,C]
              AAAATGAAACGGGACTTGTACTCAGCGACTCCTGCTCTCTTCTGCTTATTTCCTGTGTGG
              TCCCCAAGCCCTGCTGAGCCCTCCTCTTCCCTGTCTCTGGGCCTTGTTGCCACTTATACC
              CCTTGCCTCATTCAGGCCTCAGGCCCCTCCCCAGACTTATCTAGCCACCTTCCCCCTGGT
              CTCGCTGCTGCTGGCCTCCCTCCAGTCCAGCCAACACATTCAGGCGGGGACAGCCCTGAT
              AAAGCACAACAAATCTGCCTGCATCTCTTGCCTGAAGTTTGTCTGAAGCTTCTCAAAGCC

17375   GAGGCCAAGGAGGGCGGATCACGAGGTCAGGAGATCGAGACCATCCTGGCTAACACGGTG
              AAACCCCATCTCTACTAAAAATAGAAAAAAAATTAGCCGGGCGTGGTGGCGGGCGCCTGT
              AGTCCCAGCTACTCGAGAGGCTGAGGCAGGAGAACGGCGTGAACCCGGGAGGCAGAGGTT
              TCAGTGAGCTGAGACCGTGCTACTGCACTCCAGCCTGGGCGACAGAGCGAGACTCTGTCT
              CAAAAAAAAAAAAAAAAAAAAAAAAACAAAAAAAAAAAACAAAAACAACAAACAAAAAAA
              [A,C,G]
              AAAATGAAACGGGACTTGTACTCAGCGACTCCTGCTCTCTTCTGCTTATTTCCTGTGTGG
              TCCCCAAGCCCTGCTGAGCCCTCCTCTTCCCTGTCTCTGGGCCTTGTTGCCACTTATACC
              CCTTGCCTCATTCAGGCCTCAGGCCCCTCCCCAGACTTATCTAGCCACCTTCCCCCTGGT
              CTCGCTGCTGCTGGCCTCCCTCCAGTCCAGCCAACACATTCAGGCGGGGACAGCCCTGAT
              AAAGCACAACAAATCTGCCTGCATCTCTTGCCTGAAGTTTGTCTGAAGCTTCTCAAAGCC

17375   GAGGCCAAGGAGGGCGGATCACGAGGTCAGGAGATCGAGACCATCCTGGCTAACACGGTG
              AAACCCCATCTCTACTAAAAATAGAAAAAAAATTAGCCGGGCGTGGTGGCGGGCGCCTGT
              AGTCCCAGCTACTCGAGAGGCTGAGGCAGGAGAACGGCGTGAACCCGGGAGGCAGAGGTT
              TCAGTGAGCTGAGACCGTGCTACTGCACTCCAGCCTGGGCGACAGAGCGAGACTCTGTCT
              CAAAAAAAAAAAAAAAAAAAAAAAAACAAAAAAAAAAAACAAAAACAACAAACAAAAAAA
              [A,C,G]
              AAAATGAAACGGGACTTGTACTCAGCGACTCCTGCTCTCTTCTGCTTATTTCCTGTGTGG
              TCCCCAAGCCCTGCTGAGCCCTCCTCTTCCCTGTCTCTGGGCCTTGTTGCCACTTATACC
              CCTTGCCTCATTCAGGCCTCAGGCCCCTCCCCAGACTTATCTAGCCACCTTCCCCCTGGT
```

FIGURE 30

```
       CTCGCTGCTGCTGGCCTCCCTCCAGTCCAGCCAACACATTCAGGCGGGGACAGCCCTGAT
       AAAGCACAACAAATCTGCCTGCATCTCTTGCCTGAAGTTTGTCTGAAGCTTCTCAAAGCC

17511  GAGGCTGAGGCAGGAGAACGGCGTGAACCCGGGAGGCAGAGGTTTCAGTGAGCTGAGACC
       GTGCTACTGCACTCCAGCCTGGGCGACAGAGCGAGACTCTGTCTCAAAAAAAAAAAAAAA
       AAAAAAAAACAAAAAAAAAAAACAAAAAACAACAAACAAAAAAAGAAAATGAAACGGGAC
       TTGTACTCAGCGACTCCTGCTCTCTTCTGCTTATTTCCTGTGTGGTCCCCAAGCCCTGCT
       GAGCCCTCCTCTTCCCTGTCTCTGGGCCTTGTTGCCACTTATACCCCTTGCCTCATTCAG
       [C,T,G]
       CCTCAGGCCCCTCCCCAGACTTATCTAGCCACCTTCCCCCTGGTCTCGCTGCTGCTGGCC
       TCCCTCCAGTCCAGCCAACACATTCAGGCGGGGACAGCCCTGATAAAGCACAACAAATCT
       GCCTGCATCTCTTGCCTGAAGTTTGTCTGAAGCTTCTCAAAGCCACACCCTGGCGCTAGC
       ATTCACACGTCTCCGGGTTCTGCCACCCGCTCGTCTGGGGCCGCCTCACTCCCTTTCCCG
       AGCACCAGCCAGCTGGCTTCTGTCCATTTCCTCCTCATCCTGTGGTTGCCTTCCCTCCCT

17928  ATCTGCCTGCATCTCTTGCCTGAAGTTTGTCTGAAGCTTCTCAAAGCCACACCCTGGCGC
       TAGCATTCACACGTCTCCGGGTTCTGCCACCCGCTCGTCTGGGGCCGCCTCACTCCCTTT
       CCCGAGCACCAGCCAGCTGGCTTCTGTCCATTTCCTCCTCATCCTGTGGTTGCCTTCCCT
       CCCTGCCTCCACAGTTGTACCCCTGGTGCCTCTCTTCCTGCTATACCCCCTGCTGAGGGG
       TGTCTTTCCCCTCAGCCCAGGAATTTTAAAAGGGATGAAGCATCTAAGACAACAGGGGGA
       [A,C]
       CCGAAGTCAACAGTCCTGAGAGTGGCTTTCTGCTCCCTACTCTTGGAAGGATGGGCTCCC
       CAAGACCACTGGTGGCAAAGAAACCTGGGGTTTGGCCGGGCGTGGTGGCTCACGCCTGTA
       ATCCCAGCACTTTGGGAGGCCAAGGCAGGCGGATCATGAGATCAGGAGATCGAGATCATC
       CTGGCTAACACGGTGAAACCCCGTCTCTACTAAAAATACAAAAAATTAGCCGGGCACGGT
       GGCGGGCACCTGTAGTCCCAGCTACTCGGGAGGCTGAGGCAGGAGAATGGCATGAACCTG

17968  TCAAAGCCACACCCTGGCGCTAGCATTCACACGTCTCCGGGTTCTGCCACCCGCTCGTCT
       GGGGCCGCCTCACTCCCTTTCCCGAGCACCAGCCAGCTGGCTTCTGTCCATTTCCTCCTC
       ATCCTGTGGTTGCCTTCCCTCCCTGCCTCCACAGTTGTACCCCTGGTGCCTCTCTTCCTG
       CTATACCCCCTGCTGAGGGGTGTCTTTCCCCTCAGCCCAGGAATTTTAAAAGGGATGAAG
       CATCTAAGACAACAGGGGGAACCGAAGTCAACAGTCCTGAGAGTGGCTTTCTGCTCCCTA
       [C,G]
       TCTTGGAAGGATGGGCTCCCCAAGACCACTGGTGGCAAAGAAACCTGGGGTTTGGCCGGG
       CGTGGTGGCTCACGCCTGTAATCCCAGCACTTTGGGAGGCCAAGGCAGGCGGATCATGAG
       ATCAGGAGATCGAGATCATCCTGGCTAACACGGTGAAACCCCGTCTCTACTAAAAATACA
       AAAAATTAGCCGGGCACGGTGGCGGGCACCTGTAGTCCCAGCTACTCGGGAGGCTGAGGC
       AGGAGAATGGCATGAACCTGGGAGGCGGAGCTTGCAGTGAGCCGAGATTGCGCCACTGCA

18574  GCCTGGGCCACAGAGCGAGACTCCATCTCAAAAAAAAAAAAAAGAACCCTGGGGTTTGGGCA
       GAGAGAGTTGGAGCTGATGTGGCGCTGAGGGGGCTGCTCCCTCCCATCTGAGTCTCCCAT
       CTCTGCCTGCACTCTTCTGGCTGGCACTGTGCCAGCCTGCTAACCTCCCTGGGCCTCAGT
       TTCCTCCTCTGTCAAATGAGAGAGGATCTTCTCTGGGTGTAGAAAAGGACGAGGTGGTGA
       GTGGGTCTGAAGGCCTCTGGTGTCCCATAAAGCGACTCTCCTCACCATCTTTGCCACCCA
       [T,C]
       TGGGGTGTCCAGCACCCATGGAACTCTGTCTGTGCCTCTGTCCTGGAGGGAGACTTGACC
       TCCTGCTCAGGAAAGGCTCTCCAAGCCCTTGTTGTGAAATTCCTGCCTGCTGTCCGGAAC
       TCAGTCTTCCCATCCGAGGGACGAAGGTTTCGGGAAGAGAGGTGGACAGGAAGGGGTCCT
       CATCAGCGGTCCCACCCTCCTCTCCTTCCTTCGCCCTCTCCAGGCCAGAAATCAGCGAGG
       AGCTCAAGGACCTGATCCTGAAGATGTTAGACAAGAATCCCGAGACGAGAATTGGGGTGC

19654  AGAGGGAGGTCTTGTGGTCGGGAGACCAGGAGGCTTGGTGAGGAGAGTGACTGATTTAAA
       GAAATAGCGGGCGTGGGGCCGGGCGCGGTGGCTCACGCCTGTAATCCCAGCACTTTGGGA
       GGCCAAGGCGGGCAGATCACGAGGTCAGGAGATCGAGACCATCCTTGAAACCCCGACTCT
       ACTAAAAATATAGAAAATTAGCTGGGCGTGGTGGCGGGCGCGTGTAGTCCCAGCTACTCG
       GGAGGCTGAGGCAGGAGAATGGTGTGAACCCGGGAGGTGGAGTTTGCCGTGAGCCGAGAT
       [C,T]
       GCGCCACTGCACTCCAGCCTGGGCCACAGAGCGAGACTGCGTCTCAAAAAAAAAAAAAGA
       AGAAAAGAAAAGAAAGAAATACCGGGCGCGGTGGCTCACGCCTGGAATCCCAGCACTTTG
```

FIGURE 3P

```
          GGAGGCCGAGGCGGGTGGATCACGAGGTCAGGAGATCGAGACCATCCTGGCTAATACGGC
          GAAACCCCACCTCTACTAAAAATACAAAAAAAATTAGCCGGGCGCAGTGGTGGGCACCTGT
          AGTCCCAGCTACTGGGGAGGCCGAGGCAGGAGAATCGCTTGAACCTGGGAGGTGGAGGTT

21498     GGTCGCTGGAACCAGGCAACTCCCACGGGGTCCCCATGACCACTTGCCTGATCTTAGCCA
          CCATCTCCTCTCTCTCAGACCACTGGAACAACCTCCCACGCTGTCCCTTGCTTCTACTCT
          CACTCCCTGTCCCCCTGGTCAATGCTCAACTCAGCACCCAGCATGGTCCCAGTGGCATGA
          GTGTGTCACCTCCCAGCTCAGAGCCTGCTTCTCACTCGGGCTGCTGTGTCCCTCAGAATC
          AGACCTCCAGCCTGTGCCCCACCACCCGCCCTGTTTTTCTGCGGGGCTCGTGCACCGTCC
          [C,T]
          GCCATCATGCACTCGTCTCTGGCCACGTGCCATGGAAGGGGCTGCCCCAGAGCCTTCAGA
          CTTCGCTTCCCTCTGCCCGGGGAGTCCCACCCCCGATGGCCACGGGACTCGCTCCCTCAC
          TTCCTTCGGCTTTTTACGCCAGGGTCCCCTCCTAGAGAAGCGAGCCTTCCCTGACCCT
          GTAGCTTCAGCCTCCCCTGCTTCACACCTCATCGCCATTCCCTTGTTTTATTTTTTCCTT
          TCCACTTACTGACATACATAATTTACTGATTTTTCTTCTTTACTTATCGCCTGTCTCCCC

22729     GCCCTGCAGTAGCATCTTGGCATCTTCTCGGCGGCCGGAAGGCGGGAAGGATGGCACAGC
          ATCCCTCCATGGCATTGCTGCCGTAGCGAGAAGGTATCTTCTAATGGACTCCCACTTCCA
          GCCCTGGCCCTCCCCACTCTTTCAGCCTGGCCTTGCGGACCCTTCATGGGCTGGTCCCGG
          CCCCCTCCTCATGTACCAGTGGCATCCGGCTCCTCACCATTCCAGGAATATGCCCCCAGC
          TGCCAGCGCCCCGTGTTCTTGCCTCTGCCATTTCATGCTGTGCTGATTGAGATGGGACCC
          [G,A]
          CACTGCGGCCCCCTTGGCAGCTGCTCTCGGGGAATCGGAGCAGAGGCTGCGTGTCTGGGA
          GCCTGGGACCTGTGCTCCTCACGCTGCCTTGTCCTCCTCAGATCCTGGTGAAGTCCATGC
          TGAGGAAGCGTTCCTTTGGGAACCCGTTTGAGCCCCAAGCACGGAGGGAAGAGCGATCCA
          TGTCTGCTCCAGGAAACCTACTGGTGTAAGTACTGGTGGGCCAGGGACTGCCGGGCACTC
          CCTGGAGTTGGGTGGGGAGGTCTGAGGCCCATCCTCCCACTCTCACTGTCGTTGGGCCAA

22757     CGGCGGCCGGAAGGCGGGAAGGATGGCACAGCATCCCTCCATGGCATTGCTGCCGTAGCG
          AGAAGGTATCTTCTAATGGACTCCCACTTCCAGCCCTGGCCCTCCCCACTCTTTCAGCCT
          GGCCTTGCGGACCCTTCATGGGCTGGTCCCGGCCCCCTCCTCATGTACCAGTGGCATCCG
          GCTCCTCACCATTCCAGGAATATGCCCCCAGCTGCCAGCGCCCCGTGTTCTTGCCTCTGC
          CATTTCATGCTGTGCTGATTGAGATGGGACCCGCACTGCGGCCCCCTTGGCAGCTGCTCT
          [C,T]
          GGGGAATCGGAGCAGAGGCTGCGTGTCTGGGAGCCTGGGACCTGTGCTCCTCACGCTGCC
          TTGTCCTCCTCAGATCCTGGTGAAGTCCATGCTGAGGAAGCGTTCCTTTGGGAACCCGTT
          TGAGCCCCAAGCACGGAGGGAAGAGCGATCCATGTCTGCTCCAGGAAACCTACTGGTGTA
          AGTACTGGTGGGCCAGGGACTGCCGGGCACTCCCTGGAGTTGGGTGGGGAGGTCTGAGGC
          CCATCCTCCCACTCTCACTGTCGTTGGGCCAAGGCCAGAGCCTGGGGACTTGGCCAGGTC

22779     ATGGCACAGCATCCCTCCATGGCATTGCTGCCGTAGCGAGAAGGTATCTTCTAATGGACT
          CCCACTTCCAGCCCTGGCCCTCCCCACTCTTTCAGCCTGGCCTTGCGGACCCTTCATGGG
          CTGGTCCCGGCCCCCTCCTCATGTACCAGTGGCATCCGGCTCCTCACCATTCCAGGAATA
          TGCCCCCAGCTGCCAGCGCCCCGTGTTCTTGCCTCTGCCATTTCATGCTGTGCTGATTGA
          GATGGGACCCGCACTGCGGCCCCCTTGGCAGCTGCTCTCGGGGAATCGGAGCAGAGGCTG
          [C,T]
          GTGTCTGGGAGCCTGGGACCTGTGCTCCTCACGCTGCCTTGTCCTCCTCAGATCCTGGTG
          AAGTCCATGCTGAGGAAGCGTTCCTTTGGGAACCCGTTTGAGCCCCAAGCACGGAGGGAA
          GAGCGATCCATGTCTGCTCCAGGAAACCTACTGGTGTAAGTACTGGTGGGCCAGGGACTG
          CCGGGCACTCCCTGGAGTTGGGTGGGGAGGTCTGAGGCCCATCCTCCCACTCTCACTGTC
          GTTGGGCCAAGGCCAGAGCCTGGGGACTTGGCCAGGTCTCGGTGTTGGCCCCATTTGCAT

24350     AGGGAGAGCCTCATAATGAGGTGGGGGGCCTGGGAGAGGCCTGGAGGTCCCAACTGCAGC
          TTTTCTGTCATCTCTTCAGGGAGGTGGTTGCGGTTGGGGGAGGATTCTCTGAGCTCATCC
          AGGAATGTAGGCCCCTGATGCTGGAATTGTGCTTAGTGTAGGGGGAGAGGGGGCATATAT
          AATTTGACGTCCAAATGGGGACATTTTTTGAGAGTGAAAGGGGAAGCCATTAATAATTATG
          CCAGCACGGCCGGGTGCGGTGGCTCACGCCTGTAATCCCAGCACTTTGGGAGGCCGAGGC
          [T,G]
          GGTGGATCACAGGGTCAGGAGATCGAGACCATCCTGGCTAACACGGTGAAACCCCGTCTC
```

FIGURE 3Q

```
         TACTAAAAAATACAAAAAAATCAGCTGGGCGTGGTGGCGGGCACCTGGAGTCCCAGCTACTC
         AGGAGGCTGAGGCAGGAGAATGGCGTGAACCCGGGAGGCAGAGCTTGCAGTGAGCCAAGG
         TCACGCCACTGCACTCCAGCCTGGGCGACAGAGTGAGACTCCGTCTCAAAAAATAATAAT
         TATTATGCCAGCATGGTGGCTCATGCCTATAATCCCAGCACTTTGGGAGGCCAAGGCAGG

24558    GAGAGTGAAAGGGGAAGCCATTAATAATTATGCCAGCACGGCCGGGTGCGGTGGCTCACG
         CCTGTAATCCCAGCACTTTGGGAGGCCGAGGCTGGTGGATCACAGGGTCAGGAGATCGAG
         ACCATCCTGGCTAACACGGTGAAACCCCGTCTCTACTAAAAATACAAAAAATCAGCTGGG
         CGTGGTGGCGGGCACCTGGAGTCCCAGCTACTCAGGAGGCTGAGGCAGGAGAATGGCGTG
         AACCCGGGAGGCAGAGCTTGCAGTGAGCCAAGGTCACGCCACTGCACTCCAGCCTGGGCG
         [T,C,A]
         CAGAGTGAGACTCCGTCTCAAAAAATAATAATTATTATGCCAGCATGGTGGCTCATGCCT
         ATAATCCCAGCACTTTGGGAGGCCAAGGCAGGATTGCTTGAGGCCAGGAGTTCAAGACCA
         GCCTGGGCAACATAGCAAGACCCCATCTCTAAAAAAAAAAAAAATTAGCCGGGCGTGGTG
         GTGGGTGCCTGTAGTCCCAGCAACTCAGGAGGCTGAGGTGGGAGGATTGCTTGAGTCTGG
         GAGGTGGAGGTTGCAGTGAGCTGAGATTGCACCACTGTACTCCAGCCTGGGTGACAGAGC

24872    CAAGACCCCATCTCTAAAAAAAAAAAAAATTAGCCGGGCGTGGTGGTGGGTGCCTGTAGT
         CCCAGCAACTCAGGAGGCTGAGGTGGGAGGATTGCTTGAGTCTGGGAGGTGGAGGTTGCA
         GTGAGCTGAGATTGCACCACTGTACTCCAGCCTGGGTGACAGAGCCAGACCCTGTCTC
         [-,A]
         AAAAAAAAAAAAGAAAAAAAAAGTAATAATAATTATGCCAGGACAGCAGGTGGACGGACACC
         TGGTCCTTCTGACTCAGAGCCTGTGGTCCAGCACCCCCTAGTGGTGGAACAAGCCAGACA
         CAGGATAAGGATACATTTAGTGTCTAGTTTGTACCTGGCAAACAGAGTGACAAGATTGGG
         CTTAATACTTTCCAGCTATAAAATTCTAGAATTCTGTGACCCAAGTTTAATTTGGGGTAG
         AGCTTTTTAAAAAAAAAAATAGAGATGGAGTCTTGCCATGTTGCCCAGGCTGGACTTAAAC

25756    AGCTGGGATTACAGGTGCATGCCACCACCACACCGGCTAATTTTTGTATTTTTATTAGAG
         ACGGGATTTCACCATTTTGGCCAGGCTGGTCTCAAACTCCTGACCTCAGGTAATCTGCCC
         ACCTCAGCCTCCCAAAGTGCTGGGATTACAGGCGTGAGCCACTGTGCCCGGCCATAGAGT
         TTTTTATACTTTGGGATAATTGTAGAAACTCAGTAGTAGAGTTAAGTGGAGTTGGTCCTT
         TTTAAAGATATCAAAACCCATTTACTGGTTATTTTAAAAAGAGACATTTTGGGAGGAAAA
         [C,T]
         TAGATATAGAAATCTGTTGAATATGTGACAGAATCCCAAGACTGATAGATGGACTCTGCC
         CTGTGAACAAGGCAAAGAAAAATGCAAAATGAAAGCCTCTCTACCCAGATCTGCTGGGGG
         ATGACTGAGGTCAACACAGAAGGCCCTCAGGCCGGGCACGGTGGCTCACGCCTGCAATCC
         CAACACTTTAGGAGGCTGAGGTGGATGGATCGCTTGAGCCCAGGAGTTTGAGACCAGCCT
         GGGCAACATGGTGAAACCCTGTTTTTATAGAGATAAAAAAATACAAAAATTAGCTGGGCG

25968    GTAGTAGAGTTAAGTGGAGTTGGTCCTTTTTAAAGATATCAAAACCCATTTACTGGTTAT
         TTTAAAAAGAGACATTTTGGGAGGAAAACTAGATATAGAAATCTGTTGAATATGTGACAG
         AATCCCAAGACTGATAGATGGACTCTGCCCTGTGAACAAGGCAAAGAAAAATGCAAAATG
         AAAGCCTCTCTACCCAGATCTGCTGGGGGATGACTGAGGTCAACACAGAAGGCCCTCAGG
         CCGGGCACGGTGGCTCACGCCTGCAATCCCAACACTTTAGGAGGCTGAGGTGGATGGATC
         [G,A]
         CTTGAGCCCAGGAGTTTGAGACCAGCCTGGGCAACATGGTGAAACCCTGTTTTTATAGAG
         ATAAAAAAATACAAAAATTAGCTGGGCGTGGTGGCATGTGCCTGTAGTCTCAGCTACTCA
         GGAGGCTGAGGTGGGAGGATCGCTTGAGCCTGGAAGGCAGAGGTTGCAATGAGCTGAGAT
         TGCACCACTGCACTGCAGCCTGCACGACAGAGCGAGACGCTGTCTCAAAACAACAACAAA
         ACCACACACACAGAGAGAAGGCCCTTGATTAGGCTGATAGTTGGAGGATGTAGGGAAGTC

26537    TTAGGCTGATAGTTGGAGGATGTAGGGAAGTCAGCTGGGTCAGACTGTGAGCAGCTCCAG
         AGGCCGTGCTGGGAGGTTTAGACTTCATCTCTGGTCAATGGGGGCCACGGAGGCGTTGC
         GGGCTGAGACTGGGGGCTGAGAGACCGGCAAGGAGCAACTGCCGTGATGTAGGGAGGCCA
         GAGGGAGGCCAAGCTTGGGGCAGTGGGTGAAGGGGGCTTTGAGAGATGTGGGATTCAGAT
         TCCTGTGTGTGTGAGGGAGAGTGTCTCCCTGAGTGCATATTCTGACCCTGAGGTCCCTCT
         [G,C]
         TCCCTGGTGTCCCCTGAACAGGAAAGAAGGGTTTGGTGAAGGGGCAAGAGCCCAGAGCT
         CCCCGGCGTCCAGGAAGACGAGGCTGCATCCTGAGCCCCTGCATGCACCCAGGGCCACCC
```

FIGURE 3R

```
       GGCAGCACACTCATCCCGCGCCTCCAGAGGCCCACCCCCTCATGCAACAGCCGCCCCCGC
       AGGCAGGGGGCTGGGGACTGCAGCCCCACTCCCGCCCCTCCCCCATCGTGCTGCATGACC
       TCCACGCACGCACGTCCAGGGACAGACTGGAATGTATGTCATTTGGGGTCTTGGGGGCAG
28204  CCTGGAAACATGGATGGACAAGGGCTTTTGGCCACAGGTGTGGGTGTCCTGTTGGAGGAG
       GGCTTGTTTGGAGAAGGGAGGCTGGCTGGGGGAGAAACCCGGATCCCGCTGCATCTCCGC
       GCCTGTGGGTGCATGTCGCGTGCTCATCTGTTGCACACAGCTCACTCGTATGTCCTGCAC
       TGGTACATGCATCTGTAATACAGTTTCTACGTCTATTTAAGGCTAGGAGCCGAATGTGCC
       CCATTGTCAGTGGGTCCACGTTTCTCCCCGGCTCCTCTGGGCTAAGGCAGTGTGGCCCGA
       [C,T,A,G]
       GCTTAAAAAGTTACTCGGTACTGTTTTTAAGAACACTTTTATAGAGTTAGTGGAAGGCAA
       GTTAAGAGCCAATCACTGATCCCCAAGTGTTTCTTGAGCATCTGGTCTGGGGGGACCACT
       TTGATCGGACCCACCCTTGGAAAGCTCAGGGGTAGGCCCAGGTGGGATGCTCACCCTGTC
       ACTGAGGGTTTTGGTTGGCATCGTTGTTTTTGAATGTAGCACAAGCGATGAGCAAACTCT
       ATAAGAGTGTTTTAAAAATTAACTTCCCAGGAAGTGAGTTAAAAACAATAAAAGCCCTTT
```

FIGURE 3S

SEQUENCE LISTING

<160> NUMBER OF SEQ ID NOS: 4

<210> SEQ ID NO 1
<211> LENGTH: 2190
<212> TYPE: DNA
<213> ORGANISM: Homo sapiens

<400> SEQUENCE: 1

```
cgcccgcggg ctgagctcgg cgatctgggc cccagcgagg cggtggggcg gggcggggcg      60
gggcggggcg cgcagcagga gcgagtgggg ccgcccgccg ggccacggac actgtcgccc     120
ggcgcccagg ttcccaacaa ggctacgcag aagaaccccc ttgactgaag caatggaggg     180
gggtccagct gtctgctgcc aggatcctcg ggcagagctg gtagaacggg tggcagccat     240
cgatgtgact cacttggagg aggcagatgg tggcccagag cctactagaa acggtgtgga     300
cccccacca cgggccagag ctgcctctgt gatccctggc agtacttcaa gactgctccc     360
agcccggcct agcctctcag ccaggaagct ttccctacag gagcggccag caggaagcta     420
tctggaggcg caggctgggc cttatgccac ggggcctgcc agccacatct ccccccgggc     480
ctggcggagg cccaccatcg agtcccacca cgtggccatc tcagatgcag aggactgcgt     540
gcagctgaac cagtacaagc tgcagagtga gattggcaag ggtgcctacg tgtggtgag      600
gctggcctac aacgaaagtg aagacagaca ctatgcaatg aaagtccttt ccaaaaagaa     660
gttactgaag cagtatggct ttccacgtcg ccctcccccg agagggtccc aggctgccca     720
gggaggacca gccaagcagc tgctgcccct ggagcgggtg taccaggaga ttgccatcct     780
gaagaagctg gaccacgtga atgtggtcaa actgatcgag gtcctggatg acccagctga     840
ggacaacctc tatttggtgt ttgacctcct gagaaagggg cccgtcatgg aagtgccctg     900
tgacaagccc ttctcggagg agcaagctcg cctctacctg cgggacgtca tcctgggcct     960
cgagtacttg cactgccaga agatcgtcca cagggacatc aagccatcca acctgctcct    1020
gggggatgat gggcacgtga agatcgccga ctttggcgtc agcaaccagt ttgagggaa    1080
cgacgctcag ctgtccagca cggcgggaac cccagcattc atggccccg aggccatttc    1140
tgattccggc cagagcttca gtgggaaggc cttggatgta tgggcactg gcgtcacgtt    1200
gtactgcttt gtctatggaa agtgcccatt catcgacgat ttcatcctgg ccctccacag    1260
gaagatcaag aatgagcccg tggtgtttcc tgaggagcca gaaatcagcg aggagctcaa    1320
ggacctgatc ctgaagatgt tagacaagaa tcccgagacg agaattgggg tgccagacat    1380
caagttgcac ccttgggtga ccaagaacgg ggaggagccc cttccttcgg aggaggagca    1440
ctgcagcgtg gtggaggtga cagaggggga ggttaagaac tcagtcaggc tcatcccag     1500
ctggaccacg gtgatcctgg tgaagtccat gctgaggaag cgttcctttg gaacccgtt     1560
tgagcccag gcacggaggg aagagcgatc catgtctgct ccaggaaacc tactggtgaa    1620
agaagggttt ggtgaagggg gcaagagccc agagctcccc ggcgtccagg aagacgaggc    1680
```

-continued

```
tgcatcctga gccctgcat gcacccaggg ccacccggca gcacactcat cccgcgcctc    1740
cagaggccca ccctcatgc aacagccgcc ccgcaggca gggggctggg gactgcagcc     1800
ccactcccgc cctccccca tcgtgctgca tgacctccac gcacgcacgt ccagggacag    1860
actggaatgt atgtcatttg ggtcttggg gcagggctc ccacgaggcc atcctcctct     1920
tcttggccct ccttggcctg acccattctg tggggaaacc gggtgcccat ggagcctcag   1980
aaatgccacc cggctggttg gcatggcctg ggcaggagg cagaggcagg agaccaagat    2040
ggcaggtgga ggccaggctt accacaacg aagagacctc ccgctgggc cgggcaggcc     2100 tggctcagct gccacaggca tatggtggag aggggggtac cctgcccacc ttggggtggt  2160
ggcaccagag ctcttgtcta ttcagacgct                                    2190
```

<210> SEQ ID NO 2
<211> LENGTH: 505
<212> TYPE: PRT
<213> ORGANISM: Homo sapiens

<400> SEQUENCE: 2

```
Met Glu Gly Gly Pro Ala Val Cys Cys Gln Asp Pro Arg Ala Glu Leu
 1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Gly Asp Asp Gly His
        275                 280                 285
```

Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
            340                 345                 350

Phe Ile Asp Asp Phe Ile Leu Ala Leu His Arg Lys Ile Lys Asn Glu
        355                 360                 365

Pro Val Val Phe Pro Glu Glu Pro Glu Ile Ser Glu Glu Leu Lys Asp
    370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly Glu Glu Pro
                405                 410                 415

Leu Pro Ser Glu Glu Glu His Cys Ser Val Val Glu Val Thr Glu Gly
            420                 425                 430

Glu Val Lys Asn Ser Val Arg Leu Ile Pro Ser Trp Thr Thr Val Ile
        435                 440                 445

Leu Val Lys Ser Met Leu Arg Lys Arg Ser Phe Gly Asn Pro Phe Glu
    450                 455                 460

Pro Gln Ala Arg Arg Glu Glu Arg Ser Met Ser Ala Pro Gly Asn Leu
465                 470                 475                 480

Leu Val Lys Glu Gly Phe Gly Glu Gly Gly Lys Ser Pro Glu Leu Pro
                485                 490                 495

Gly Val Gln Glu Asp Glu Ala Ala Ser
                500                 505

<210> SEQ ID NO 3
<211> LENGTH: 29629
<212> TYPE: DNA
<213> ORGANISM: Homo sapiens

<400> SEQUENCE: 3
ccgcccgcgc atccatctgg gcctcagcgt gtcccgagca atcacaacag cagccgcaca        60
acaacaactc acttttacgg cctccttagt ggcaggcact gttctgagcg ccttacgggc       120
gttccctcct cagcatctca ccacgtgcgg tgaggtgagg cccgctagaa ccccatcttg       180
cgggcgagga aaacccaagg cacagaggcg aagccacctg ctcacgggct cccagccagg       240
aaagggtgca gcctggctgc ctggcttcag agcctgggcg ccaaaccggg taacagggct       300
caggctggaa caggaaacct tctgccccga cttgctgggt gaccccgggc ccatccccac       360
ccgctgggcc tccctctacc tatctaagaa aagcaggaa aggtgttcaa ggtaaagga        420 ggatggcctc ttgctggaat ggcaacctca aggaaatacg caaattttat gggcccgggc       480
agcctgtggc ttctgcctgt gcggctctg agtcccgtag tccctgccta gggccaaaaa        540
gcaggagctc ctgactctgg agttcattct gttatatgtg ctggggcctg aggcttgctg       600
gggttgcctc tctgaggctg ctttctcatc tgtctaatgg ggacagggct gtaacgatca       660
ctatggcaac cactcattta ttcaacaaat atttatcgag ttcctatcac atgccaggca       720
ctgatgatct tttggagaca aggcagatga gcgtcctaat ctcatgaaac ttacattcgg       780
gagggaaaaa caaggcatgc ggagtgaggg gaaggggcgg aggggtgggc cacctgctgg       840

-continued

| | |
|---|---|
| gaggagcctg gcgggtcctg gagggtgttc ccagctttgg cttcctcctt cctatgctgt | 900 |
| ctggtttcca agctctcccc gaagctccag ccccactcac tgtccctctc acctcctcca | 960 |
| gggaggcctc cctatgccac agcctctcac ctcctctggg gaggcctcct tatgccacag | 1020 |
| ccccactctc tgtcctctct cacctcctcc agggaggcct ccctgtgcca cagccccact | 1080 |
| ccctgtcccc tctcacctcc tccagggagg cctccttgtg ccacagccgc actcactgtc | 1140 |
| tcctgccctc tcttccaggg aggcctccct gatactctag cctcactcag cctcctcacc | 1200 |
| tccttcacct cctccaggga ggcctccttg atgttccagc tcattaact ccctctcact | 1260 |
| cctctgggtc cagcttccat gacttttcct gttcctagtg tggagcctcc tctcttcctt | 1320 |
| tctccatgtc agcaccagcc ccaccgcctc caggcttcta ctcattcaac acactgcgta | 1380 |
| ccgggcacag ggggtctgga cctcacccctt accctcagtc tacctccaaa ccctgctgtg | 1440 |
| agcctggaaa atatgggaag gcagggaatc cacaggacaa gtcgggagac tggggctcag | 1500 |
| agtcgggaag gagctggtct agggcccctg gtgggtcagc aggcaggact ggaacccagt | 1560 |
| cctggctcct cagtggccgg tggactccag ccagccctgc ctcgctgaca tctgtcaaag | 1620 |
| caaggggatg gggaacgagc ggtagagcag gcgcttcacc atgcgtactc tgggtctccc | 1680 |
| tgagacccat gttctcagtt gctgtgtggg ttcggaggaa gttaccagca gacaggaagg | 1740 |
| atggagggtc aggagttcac tcacttcctt ctcctgagaa catgcagagt ccagcgcaag | 1800 |
| caggggaag gcatcaggt tgggcatggc agcgctcta caagcctggg acagagatgg | 1860 |
| gggtctcagg ctgagtgtca gggttcagtc cggggtcagg atgtagccca gggtcatggc | 1920 |
| tgaaggtgag ggctgggggt cacctccctg atgtttcagc cgccacacag tgagtttgag | 1980 |
| aacatgagtc tcagggggatg tcatgcccct gtttcacccc tcattcccct cattcccatc | 2040 |
| ccccttgcttt tttttgaaac cgagtcttgc tccatcaccc aggctggagt gtagtggcgt | 2100 |
| gatcttggct cactgcaacc tccacctccc aagttcacac gattctcctg cctcagcctc | 2160 |
| ccgagtagat gggatttcag gtgcacgcca ccatgcctgg ctaattttttg tattttttaat | 2220 |
| agagacagag ttttgccatg ttagccaggc tagtctcgaa cttctgacct caggtgatcc | 2280 |
| acctgcctcg gcctcccaaa gtgctgggat tacaagtgtg agccaccatg tggggcccat | 2340 |
| cccccttgttt tgacagacgt caatgaggca gggctggctg gagtcgggag ccccagggaa | 2400 |
| gtcttcctgg aagcagtgag agggatgggg gtaggaggct gaaacatcaa ggagggctcc | 2460 |
| ctggaggagg cgggtgggtc tgaagcatca gcaaggcttc tgagttacta gtgtctagct | 2520 |
| cagcttccag gaggcagtgt cggagtgctc tgctgtcaag ggttgggact catgactcac | 2580 |
| agggctgcat gctgtgctgg ggctgagctg accctgggct ctgccccttc cagtgctgct | 2640 |
| gggcctccag gcttctgccc tgtctgtcct gattccagaa tatcagattc tctctgcttc | 2700 |
| cctgtgaagc cagcaggcag aagtgactgc ctctgttacc ggcagggata ctgaggccta | 2760 |
| gagggctggc atgcggcaga accgatgtga attcattcag gtcatagga cagacttgag | 2820 |
| tttggtgtt ggcaatcccg gtagagggaa cagccaggc aaaggcatgg aggtgggacc | 2880 |
| cacagcgctg tggctacctt acctggtagc cagcctgaca cccaggagtg aagccttctc | 2940 |
| tgccttcttt tctcaggttc caacaaggc tacgcagaag aacccccttg actgaagcaa | 3000 |
| tggagggggg tccagctgtc tgctgccagg atcctcgggc agagctggta gaacgggtgg | 3060 |
| cagccatcga tgtgactcac ttggaggagg cagatggtgg cccagagcct actagaaacg | 3120 |
| gtgtggaccc cccaccacgg gccagagctg cctctgtgat ccctggcagt acttcaagac | 3180 |
| tgctcccagc ccggcctagc ctctcagcca ggaagctttc cctacaggag cggccagcag | 3240 |

-continued

```
gaagctatct ggaggcgcag gctgggcctt atgccacggg gcctgccagc cacatctccc    3300
cccgggcctg gcggaggccc accatcgagt cccaccacgt ggccatctca gatgcagagg    3360
ttggtggggc agaacgaggg gttgttcatg agcccctcag tagtctgcaa tgaagactct    3420
ttcctgcccc tgtctgtgcc acacggctat ctagctttgg tttgcatacc ctcagagctg    3480
gggagatcac tacctaacaa tatagcttct tcccaaccag gggagctcca gctgagccaa    3540
aggctgcctt ccctaagtcc tgctattccc actcccagcc caggcctagg aaataggtct    3600
ctccctggtc cctatgtag tcttcttaga gatgtgaaga tagatgctat gtcccccttc     3660 cccctaact cttctccagc ttgcacccct cgcctctaat tctgcctctt agagtctgct     3720
gtgactcaga agcggccggc ctgcctccag cctctgggct tctgctggag ttcttgccat    3780
ttaggtctga aagtgaactc aggttccaag cagtctacag atgtcagggg ctgagctttc    3840
tgtgcctgaa cccaggctct cagcctctgt gcccagggcc cctcatcttg tccttggagt    3900
ctagaccttc tcattcagct gcttctggaa atagttgctc atgggtttct catggattag    3960
ggtcttccag actccagaat ccagacagga attagcgttt tcccttcacc actgcttctg    4020
gggaacaagg cacagccatg gcgtcaccat ccatgttttc aaacatgagc cacgtcttct    4080
cgtcacatac gggggcgatg gcaccaccaa cttccccatc caaactcaaa agcttggtga    4140
gacctggggg tccgggaatg aggagcttat ggccagaatt ggaccctgaa cgggctctga    4200
ggtaggagca gtgctgcctc cggacccagc tccacctggt gctcgctctt cccccacagg    4260
actgcgtgca gctgaaccag tacaagctgc agagtgagat tggcaaggta ggagtgggca    4320
ggccgagagc agtgggggct tcgggattct ctgtttggcg ctgctccttc tctcgtgtgg    4380
gagggaacgg gaggcagagc caggcaagtc ctagcctgga ggtgaggaca gtttcgtgcc    4440
ctgtgggaag tacccaggta cccaggggga gggtggaaga tggctcctga ttcccgactc    4500
tctgagttct tgacagtgga caaggaggga ctgagggagg catggagcca tgtggagcca    4560
agcaggggca gttaccaggg cgcaggagtc ccctccccat ctgctacaat atttgcccgt    4620
gagccagctg gtggtgggta gtgcagatgg ggtgcaggag agaccagagc tgctcggctc    4680
cccacctcct gagctggtcc tgggaggggt tgccctgtcc aggtggggct gactgatgcc    4740
tatctgcagg gtgcctacgg tgtggtgagg ctggcctaca acgaaagtga agacagacac    4800
tatgtgagtc tggggatacg agggaggtgt tgcccaagcc aggccctgga agcctgaggg    4860
gtggggcagg agttgtgctt aggagataga ggacagggct gcctgagagt gagctccctg    4920 tcccctagggg tatgcaaagg aatgagcttc ctaaccctgg ggatatgcaa gcagagactg    4980
gattcctctg aggggaaagc tccagaaagg cttgctgggg gaataagggg aagggctagg    5040
ctcagatatg gccaccccca accccgctta acacttacct gggccacacc ctcagggcca    5100
gtagcagatg tccagtgtgc ctctccggac ctcagtccac atgtaccagc ctgttctagc    5160
ccctggtggc tgcacagtag tgacatttct gtccctcctt ccttaggcaa tgaaagtcct    5220
ttccaaaaag aagttactga agcagtatgg ctttccacgt atgtatcttc tgatcctgtc    5280
cctgggagct cctagcctgg aggcagagga ggagacctcg atcctgagct agttttggct    5340
aggaatgggg tagagaggga gacagcgtga gcagaggcct ggggacagaa tgtgccctgt    5400
gggttgggac aagaccacgg gcatgcaaga ctcttgcttg agactggttt ggggggccacg    5460 gtgaggccca gccacctgga acaggtgttt gagttctctt cctggtcaca ggtcgccctc    5520
ccccgagagg gtcccaggct gcccagggag gaccagccaa gcagctgctg ccctggagc     5580
```

```
gggtgtacca ggagattgcc atcctgaaga agctggacca cgtgaatgtg gtcaaactga   5640
tcgaggtagg gggtggtggt gagcaggtgg gaaccagcac ctgagtctca tgggagccgc   5700
ttctggtgct ggggagcccc tagcacagac ccagggatct tgcccaggtg gcagatgtgg   5760
ctgaggcctc tgaggacagg gccagacttg gggtggggct gcaggaaggc tttggggggcc  5820 cagcctggtc agggatgttc ccaagttccc atggagggtg aggggctgcc ccagaggcaa   5880
gaagtgagcc cctcattgca gctggagggg aggaaggctg gatgtcgtgt ggcgggccag   5940
gttgggggtc ggtgacttct gaggccccat cagtctggca ccacctgtac acttcctgct   6000
tccttgtctg gggtggttgc atgcatacta agggttctgg ggctggcaag gaccaggagg   6060
cctgggacct ccaaccccac gcctcctcaa gccccacccc catgtctgct ccctctgacc   6120
aggtcctgga tgacccagct gaggacaacc tctatttggg tgagtgacct ggctcattcc   6180
cacagcagct cactcagggc tggcccaagg gctcccttgg gacatgtatg accttcaggt   6240
gggcggtgta aatgcactga cctcctgggg acagaagaaa aacacacgtt ctgaagccct   6300
ggattccctt gcccagccct gcagaaccag gcccagaata tccagttaga ttcaacaaat   6360
atcgccaagc cccactccct gcttccctct gagcagcaag acagtggatc cacgtgggct   6420
gcgcgctcag gtagatgcag gaagcaggct gcatgggttc ccagacactg tagctctgtg   6480
cctcagtttt cccacctata aaacagggat actagtggtg tctacctcat agggttcctg   6540
tgaagagtaa atgagtaatt atatgtaaag cacattcgtt attatccttg ttaatagtaa   6600
tgttattatt ttagttcctt gtgtctggtt cagggctggg cttagaggag gcctcagaaa   6660
atggggcaga agaagaactg gcttaggaat tagaggctga ggctttagtc tccactccct   6720
accctacctg cctgtctgct atgaccttta ggaaaatttc tgccccttct ctgtgcctca   6780 gtttcccccct ctgtaaaagg gccccatgct gatgctgatg ttctcacct ggcacctgag   6840 gatcagatga gacaggtcca tagcagaccc cactctcatg catttatttg ctctcatatc   6900
ccagggtccc ctgtcctgtc cctgcctcga gtatgcctgc atgcctgccc cctctcctac   6960
cctccagaac agggagggac cttggcatcg gctgctttgc cagccagcta caccttacct   7020
tcttgtcttt tcttttcagtg tttgacctcc tgagaaaggg gtgagttccc cgtcctgatc   7080
aggcaggtca attctcatcc aggccttcct tcctttccct ccctgtgtcc ccagcccagg   7140
ggtcagctac tctaggagaa gtcagagacg gaggccctgc ccttaggggt aaataagaga   7200
ccaagaggac cattctttga aggctgatgg gggtcagtga ggctgaaata gtcagggaga   7260
cctctggaaa aggggacgga ttttgaccca ggccttgaag aactaggaag atagggatgg   7320
aggagagggg gaagaaagga gtgttttttta ggtaaaagta tatagaggtg ggactcaact   7380
cttaccggta ttcaaatcac aaagggtttt tcagctttcc aacaagtctg tgaatggagt   7440
gggtgggatt ccagttgctc ccatttgtga gaggaaagc taaggaccag agaaggtacg   7500
tggcttgctc aaggtcacac agcaagtcac tgatggagcc caggcttcca catgtctgcc   7560
ctatgcggct tttcagggta tttacagagc agatgacatg gagtaatgag cacgggctg    7620 ggtggtccgg gaccctcact gccaaggctt gaatgcagcc tgcggcttgt ccctttgcct   7680
gggcggctcc ctacagacca atctggggag aggggcaggg agtggtgtcc ctttaagact   7740
tggaggcttt caaatgtttt gacctctatc caaaacaaga aatatatatt tctattgcta   7800
tccatatctg taactgaaac caaaattttta caaagcagca tatatcttta ctacatgcaa   7860
tatattctga tatattctac ttatttagga aaaaaaaaa aaagcagttg ccacccacta   7920
aattgatttc atgatcctct cttgggtctg gatccacggt ttgaaacagt gctctaaatg   7980
```

-continued

```
gcatctttgc aattgattat ggacaattaa gtacttagaa gaaggaatat caagccaatc    8040
agaaattaag agaaagctga tttgaaatta tgattgaaat gggatatgta tgagtatgtg    8100
tgctttaagt tttttattat gtagcagaaa aagctaatat cttgagttgt agggactcat    8160
gtgggcacag gtttcccggg acgtcccgac cacctgaatg gccgggtgcc ctgatttcag    8220
ctgaatgccc ctccccgcat ccttctccat aggcccgtca tggaagtgcc ctgtgacaag    8280
cccttctcgg aggagcaagc tcgcctctac ctgcgggacg tcatcctggg cctcgagtac    8340
tgtgagtgcg gggcagcttg cccactgggg ctggggctag gggatctggc aggcggcaga    8400
gcccaggctg agcagactct gagcagctcc cgtcagtcag agctgacctg ccaatcagct    8460
tcagtgggag tggggcatgc acgtgtggcg gggccaaagg cctttttgtg gggtggggcg    8520
ggcggtggac tccactgggc atgtgccaga tccttcgtcg tgtctggtcc tgtgggtctg    8580
agtcctggct gttctgtatc tttcttctgc tgagttctta gcctagctta gcgttgccac    8640
ggggcttcaa gagatgtggg aaggaaggga tttatgtcca gctgctgggg agagtctgtc    8700
ctggcatggg gccggggcat ggtggcaggg tggatttacc tgtgaggggc cctagtctga    8760
taagagctca ggagggtgat gtgagcttgg cctctgtctc atttcattca ttagctacat    8820
tcacttgcct gggggcatag gggtgaaaga cccagacccg agttcacggc ctagtgggag    8880
ggacaggaat ctaggcaggc agataataca gcgtggtgcc tgccaaggct ggggagccta    8940
gaggctgtag gagtgccggg gggctgggga agtctccctg aagaggctac ttatgattcg    9000
ggtcctgagg gatgagtaga cttccctgct caggttttga gggatgggcg tggaagacga    9060
tgtgcctggc ataggcgtgt actctgagtc tggggagaag tggagtctgg ctgaagcctc    9120
cagtgggcag aggagggccg tggttagtga agatgatgc tggaaacact gtccgggcca    9180
cagcatgagg gctgggaatc cctcccctga ggtctttgct gactgcatcc tgccagctct    9240
gtgaggccct gagagcttta agcatgggga ggggcgtgat gggatttgtg cctgagaaag    9300
ctctgtctgg cagctgtgtg gtggctggat tggagtgtgt catcggaggg tgagaggcag    9360
ccagctggcc agggaggagg ctgtttctgc agcccaagtc acagatggtg aggcctggat    9420
taaggcagtg gcagcaggat ggggatagga aggaggtggg gtggtcagca tggagtgact    9480
tgccggtctg gggagaggag agcccctaga cacctagggt cctggcgtgg gttggggacc    9540
aggggagatg cccatctcta aaatcttagc ttgggccagg cgcagggct catgcctgta    9600 atcccagcac tttgggaggc cgaggtgggt agatcacctg aggtcagggg tttgagacca    9660
gcctggccaa cgtggcaaaa gcctgtctct actacaaata caaaattag ccttgtgtgg    9720 tggtgggcac ctgtaatccc agctactcgg gaggctgagg caggagaatc gcttgaacct    9780
gggaggtgga ggttgcagtg agccgagatc acgccattgc actccagcct gggtgacaag    9840
agtgaaactc catctcaaaa taataaata aataaatgca tacatacata tatcatacata    9900 tacataaaaa taaaaataa aatcttagct tggtttcttg ggagcatatt ctttccctgg    9960
gggaacaggg tgggatctg gctgaggttt gacctgcagt gacagaaaca ggactgtctt   10020
tatcctgctc gagcctctcc tttgccttca gattaagact ctctttgcac atatggggaa   10080
actgaggcac acagaggga gggctttgca gaaaatccct accaagggcc tagaggcatg   10140
ggatgggaag gggacatttt accccggtac ggtcagtggc aggcacagtc ctgtaccagc   10200
ttggctccac ctccttctg ttgtagtccc ttctttcccc tgaagtcctg ttgtctgcta   10260
tcccctagcc tccacaaaga aacgagttta tcttacctgg ttcttgggta aagcctcatc   10320
```

-continued

```
aggacccagc taatcacagt gaagggcttc cctggggcag aacggttagc gccagggget    10380 ggacaggtgg atgaacagag gcacgagggc gctgaagacc tgccttgtga ttctggcccc    10440
aagaagagag agttgaggct gccatgagag ggctcggtgg tcagggcggc ccaggcctgg    10500
ttctcagttg atgggggcag gtgcaacgat gcagatgatg agaagcagtt ggatctggaa    10560
tagatgtgag aagctgagct cacagacctt gctgatgagc aggatgtggg gtctcagagg    10620
aggaattgag gatgatcctg aagttttttgg cctttcacag aatggaaaag aatggggagc    10680
agcaggggcg ttttgttttg ctttgttttg attttgttgg tggtaggcat tgcaggcaga    10740
gaaatcaagt tctgaattag acatgttatt gcactgtgtt cagatataca gagacatata    10800
tcgatgccta gctgcctagt tatctaccaa gatgtctatt ggaaatctat gtgggtaaag    10860
agctggagtt caagggagag gctagggttt gagataagaa catgagacca ctttccatgg    10920
tcaaatgtcc acccccctga gcttctgtgc cctgaagggt gtgtcagatt ccttgtgtgt    10980
gcctggcaca tagtaggcaa tcaagaaagt gccactggtt ttatggttat tgttatacgg    11040
cacccgcctt ctctgcccgc agcctccctc tcctcttctc ccttcctctt tcttctctcg    11100
ccttctctcc tccctcctct ccagcatcct ggggtccgtt ggtccagatg aaggtacttg    11160
ccaaggaggg agcccacagg tcgatggtcg cgggatgggg tcagtggggt cattgtctct    11220
cttggctggg accttaccag tcatgtcagc ttgagccacc tgtcacttcg tggtggtgct    11280
gggcccagaa agcagggcag acctccagcc tattaggtca tttctgattt gggattcgtc    11340
ctactatatg tggctgacct tacaccccag ctgtgtcatc ctgcttgtcc caaggcctgg    11400
ggtgccatcc atctctctga aaccccatca gcccagatcc cgagggctga gatggtacct    11460
ctgtaggata gcagagtccc tacaatctta ctctcagtcc cagcagcagg gacatctttg    11520
cctagcctgg gtgggggatg gaactggaga aaggttttga ttggcttttgg gcctgcagac    11580 ggcactcaca gggaagggge agagctagcc taggaagaac tctgctccca gctggggggcg    11640 gtggctcacg cctgtaatcc cagcactttg ggaggccgag gtgggtggat cacctgaggt    11700
caggagttca agaccagcct gaccaacatg gcgaaaccct gtctctacta aaaatacaaa    11760
aagtagccgg gcgtggtggc agacacctgt aatcccaact actcgggagg ctgaggcagg    11820
agaatctctt gaacctggga ggtggaggct gcagtgagcc gagatcacgc cattgcactc    11880
cagcctgggg gacagagtga gactctgtct caaaaaaaaa aaaaaaaaac caaaaaaaaa    11940
aacagcaaca actctcctgc cctagtttcc tctgacctcc ccactcagca gcagatccct    12000
tgtttgtcat ggagagggtg ctggacttgg agtccaaaga ctcctaagat tccagtcctg    12060
gctctgctgc tcacagcctg ggctcagtgt ctgcacctgc gtggagcaga tggccctgac    12120
gtcctcctcc caggtcgtca ccagacgaaa gtgtgcatgg gctgggatgt cccggccggc    12180 gtccctgget gtgcaaggac gggtgtgggg tcctggccag cggtgcccag ccagcgctc    12240 agctcaagct ccccttctct gcagtgcact gccagaagat cgtccacagg gacatcaagc    12300
catccaacct gctcctgggg gatgatgggc acgtgaagat cgccgacttt ggcgtcagca    12360 accagttttga ggggaacgac gctcagctgt ccagcacggc gggaaccca gcattcatgg    12420 ccccgaggc catttctgat tccggccaga gcttcagtgg gaaggtgact cgcaggccct    12480
gggccaggct ggggttcaag tggggggcgt aatagcttgc cgcagtggcc cagttctaa    12540 cctgaggtg ccagggtctt tgtgtctagg gagtgacata tttgcctctt ccttggagcc    12600
tgacaaactc cacaactttg gccttctcct gttttccagc aaagtggtcc caaatctccc    12660
ttgcagatat ttactgttgg ttgctctgtg ctgggttctg gaccggactg tggaagaggc    12720
```

-continued

| | |
|---|---|
| agaaacaaag agaaccctgt ttcctgccct ctggatggtt tcgggggaag ttgggggtcc | 12780 |
| ccgcagatct tgggacatgg caggatttga actggcccctt gaagaatggg gaggatctga | 12840 |
| gcaggacctg gagcctagag aataaaccag agaacagaag ggctcaggct gggggggcaga | 12900 |
| gggtataaag ggcctggaag tttgggcttt ctcctaagtg acaggagcgt aggcaaagtt | 12960 |
| gtctgaacaa gaggttacac ggtctggcgc agttccctgg gcacatggct gtttcaccta | 13020 |
| tggagtgcca gccaccccac tgccagggag gctgtgggtg agaggcattt ggacacgtgt | 13080 |
| gagtatccag gaaagaggtc aggaggccgg gcacagtggc tcatgcctgt aatcccagtg | 13140 |
| ctttgggagg ccaaggtgga tctcttaagg ctaggaattt gagatgagcc tgggcaacat | 13200 |
| agcaagaccc catttctaca aaaaaaaaaa taaaaacatt agacaggtgt ggtagtgcac | 13260 |
| acctgtagtc ccagctactt gggaggccga ggtgggagga tcgcttgagt ccaggagttg | 13320 |
| ggggctgtag tgagctgtga tggtgtctag cctgagtgac tgagcgacac cttgtctcga | 13380 |
| agaaagaaag aaagacgttg gggatgttga taaagatttt ttgaaatgtt ttattttgat | 13440 |
| ataattctaa atttacagaa aagttggaag aatagtacaa agaaatcccc tatatctttt | 13500 |
| tacccagatt caccaattat tgacattttg tcccactggc ttttttcatca tcttctttt | 13560 |
| tttttgagcc ggagtctcgc tcctgtcgcc caggctggag tgcagtggcg cgatctcagc | 13620 |
| tcactgcaag ctccacctcc tgggttcacg ccattctcct gcctcaacct cccgagtagc | 13680 |
| tgggactaca ggcgcccacc accacgcccg gctaattttt tgtattttt agtagagacg | 13740 |
| gggtttcacc gtgttagcca ggatggtctg gatctcctga cctcgtgatc cgcccgcctc | 13800 |
| ggcctcccaa agtgctggga ttacaggtgt gagccaccac gcccagccag aaatttatca | 13860 |
| ttgataagac ttatatatcg gtcaggcatg gtggctcatg cctgtaattc cagcccttg | 13920 |
| ggaggccaag gtaggtggat cacctgaggt caggagtttg agaccagcct ggccaacgtg | 13980 |
| gtgaaacccc gtctctacta aaaatacaa aaattagccg ggcatggtgg cgggcacctg | 14040 |
| taattccagc tacttgggag gccgaggcag gtggatcacc tgaggtcagg agtttgagac | 14100 |
| cagcctggcc aacgtggtga acccccgtct ctactaaaaa atacaaaaat tagccgggca | 14160 |
| tggtggcagg cacctgtaat tccagctact tgggaggctg aggcagaaga tcgttcgaa | 14220 |
| cccaggaggc agaggttgca gtgagctaag atcgtgctat tgcactctag cctgggcgac | 14280 |
| agagtgagac tctgtctgaa aaaaaaaaga catacataat ccacagacct tatttaaatg | 14340 |
| ttatcagttg tcctgatact gtacttcata acttcttctt tttctggtcc cggaatccaa | 14400 |
| tcgaggacca cttgctgcat tcaccttctt gtctgtggta tcctttcatc tggaagaggg | 14460 |
| ccttggcctg ccgttgtctt tcctgatctt gacattttgg aagacaacca gcctgttatt | 14520 |
| ttgtagaatg ttgtcagttt gcatttgtct ggtgttccct ggttgggatt cagatgatgc | 14580 |
| atctggggca ggaatatgta ggtagagatc gagaatcact catataagcg agaaagtgga | 14640 |
| taccagaaga ggtggcgttc cggagcagaa ggtagagaga gcacacgctg gagtccaggg | 14700 |
| cgcggggagg cccaggggtg tttggagcc cagaggagtt gttgcagtgg cggtggatga | 14760 |
| gggcgtgaga ggacagggcc tctgtgtggg caggggctgt ttgcaatatc aggaagaagg | 14820 |
| tggattatga ggagaaggga tgactccttg aagcccgagc tggtttagtg agcagaagtt | 14880 |
| ccatatatac catcattcct ggggtgcgtc tgtggcacgg gagcggcccg tgtgaccctc | 14940 |
| tggatgaagg aggttttgta cctgttgagt tggaaacgta cctggttaga gtcttcccca | 15000 |
| aggaaaccca gaaccctgg agggtggagg ccttgttctg gccgcccctg tgtcctcagc | 15060 |

-continued

```
actcagcacg gggcccagca tcgggcaagt accgcggagt gtttgtcgag tgagtacatg   15120
acagaggaaa gaggttccct gcaggcctct cctgcagccc gctggagctg ggtgggcaga   15180
ggtggctgtg cctgttgggg actgatgtga gcatgtttct ttccaggcct tggatgtatg   15240
ggccactggc gtcacgttgt actgctttgt ctatgggaag gtgagtgcca gggatgccag   15300
cagagctggg gcgggtccag tgaggcgggc acgggcgacg gatgcaggct cttccttttt   15360
gtccttaagt ggcttttgaa agagcccacc tggctcagag aaggctgaga gagaagaggc   15420
tttttctatc tttctctggt cccctgcgga gcgattctcg cgaaggagtc gcaggacagc   15480
agacacctaa ggggaggtgc cgacgatggt gttgccaccg ccccagccag agtgctcccc   15540
gtccctctgt cccttgacgc cattcactta ttgagccatg tgttcactcc cttgctcatt   15600
tattcgacaa attgtccttc accctaccc tggctgaggc tggaccctgg ggacacccaa   15660
cgctgacgta tcggtgatcc ctgcccgcag gtgtgcctgc tctggtgacc acactaaggg   15720 gcaggggga atttcagtga acatgttccc aagccccagg ccctgggagt ggaggcctgg   15780
ccacaggtgg cggtaatggt ggtgggtgca cccagcctgg cctggcttgg ccgcgggtgg   15840
cagtaacggc ggtggatgca cccagcctca ttgttccctc agcaactcat tcattcagtc   15900
aacatttgtt gaacatttac agtgtgagtt gaggtcctc tcatgtaatg ggagcccaga   15960
cctgccccct acccctgccc ccaccaaggg agggggttg atccctggc acaggtcgag   16020 gccctggacc cacatccttt gtctgcctct ccaccccaca gtgcccgttc atcgacgatt   16080
tcatcctggc cctccacagg aagatcaaga atgagcccgt ggtgtttcct gagggtgag   16140 ttgtccaccc aggggaacaa gggggctacc acccgctcct ggtgtctgag ttttagcaga   16200
gcttttgccc tctgaggacc ccaccccagc ctgcagatat gaaggtggcg gtgctgttcc   16260
ctgggaggga cccctgaata gatggacggg agggactctg gagccaaggg tctccgcaac   16320
gtcactgtgt ggatgggaac cctgagatcc agggttggcc agggatgacc acaggcatca   16380
ttcacaccac tccttcaccg caggcctgcc tggggtcagt ggcgccagcc ccacccagcc   16440
cctggactca aggggaactt ctccttcccc cactcagggt cagggaactt caagatgcca   16500
gtgcgtgctc cccatttcac agatggaaaa gaggatgctc tggaggagag cggtcagggg   16560
gctgggactc aagccactct tcctccccac tcttcccatt gtgaccgagg tctctgagcg   16620
tagcagggat gtcggggagg cctcttgctc atgcatggtt cgcctcatga cggccaccgt   16680
ggcagccaca gcctgagctc ccaggctcct cttttcagca gtggatttca ggagtgaaat   16740
ggaggccggg tgcggtggct cacgcctgta atcccagcac tttgggaggc tgaggtgggc   16800
agatcacctg agttaggagt tagagaccag cctggccaac atggtgaaac ccatctctac   16860
ctaaaaatac aaaaattagc caggcgtggt ggcgcacatc tgtagtccca gctactcggg   16920
aggctgaagc acgagaattg cttgaaccca ggaggcagag gttgcagtga gcctgggcga   16980
cagagcaaga ctctgtctca aaaaaaaaa acagaagaaa gaaactgaat aaggccgggt   17040
gcggtggctc acacctgtaa ttccagcact tgggaggcc aaggagggcg gatcacgagg   17100
tcaggagatc gagaccatcc tggctaacac ggtgaaaccc catctctact aaaaatagaa   17160 aaaaattag ccgggcgtgg tggcgggcgc ctgtagtccc agctactcga gaggctgagg   17220
caggagaacg gcgtgaaccc gggaggcaga ggtttcagtg agctgagacc gtgctactgc   17280
actccagcct gggcgacaga gcgagactct gtctcaaaaa aaaaaaaaa aaaaaaaac   17340 aaaaaaaaa aacaaaaaac aacaaacaaa aaaagaaaat gaaacgggac ttgtactcag   17400
cgactcctgc tctcttctgc ttatttcctg tgtggtcccc aagccctgct gagccctcct   17460
```

-continued

```
cttccctgtc tctgggcctt gttgccactt ataccccttg cctcattcag gcctcaggcc      17520
cctccccaga cttatctagc caccttcccc ctggtctcgc tgctgctggc ctccctccag      17580
tccagccaac acattcaggc ggggacagcc ctgataaagc acaacaaatc tgcctgcatc      17640
tcttgcctga agtttgtctg aagcttctca aagccacacc ctggcgctag cattcacacg      17700
tctccgggtt ctgccacccg ctcgtctggg ccgcctcac tcccttccc gagcaccagc       17760 cagctggctt ctgtccattt cctcctcatc ctgtggttgc cttccctccc tgcctccaca     17820
gttgtacccc tggtgcctct cttcctgcta taccccctgc tgagggggtgt ctttccccctc   17880 agcccaggaa ttttaaaagg gatgaagcat ctaagacaac aggggggaacc gaagtcaaca    17940 gtcctgagag tggcttttctg ctccctactc ttggaaggat gggctcccca agaccactgg    18000
tggcaaagaa acctggggtt tggccgggcg tggtggctca cgcctgtaat cccagcactt     18060
tgggaggcca aggcaggcgg atcatgagat caggagatcg agatcatcct ggctaacacg     18120
gtgaaacccc gtctctacta aaatacaaa aaattagccg ggcacggtgg cgggcacctg     18180
tagtcccagc tactcgggag ctgaggcag gagaatggca tgaacctggg aggcggagct     18240
tgcagtgagc cgagattgcg ccactgcact ccagcctggg ccacagagcg agactccatc    18300
tcaaaaaaaa aaaagaaccc tggggttttgg gcagagagag ttggagctga tgtggcgctg   18360 aggggggctgc tccctcccat ctgagtctcc catctctgcc tgcactcttc tggctggcac   18420
tgtgccagcc tgctaacctc cctgggcctc agtttcctcc tctgtcaaat gagagaggat    18480
cttctctggg tgtagaaaag gacgaggtgg tgagtgggtc tgaaggcctc tggtgtccca    18540
taaagcgact ctcctcacca tctttgccac ccattgggggt gtccagcacc catggaactc   18600
tgtctgtgcc tctgtcctgg agggagactt gacctcctgc tcaggaaagg ctctccaagc    18660
ccttgttgtg aaattcctgc ctgctgtccg gaactcagtc ttcccatccg agggacgaag   18720
gtttcgggaa gagaggtgga caggaagggg tcctcatcag cggtcccacc ctcctctcct    18780
tccttcgccc tctccaggcc agaaatcagc gaggagctca aggacctgat cctgaagatg    18840
ttagacaaga atcccgagac gagaattggg gtgccagaca tcaaggtcgg ggaactgggg    18900
gtcttgggct gggctgggac acagaaaaca ggagtcactt tcccttttctg gagggatcaa   18960 caccaggatg catgtgtgtt gggtttgagt ctgtggactt tggacccctc caggtgattc    19020
tggtaatggc ctgacctctc cccctctccc tgccctcccg gccccgacag ttgcacccctt   19080 gggtgaccaa gaacggggag gagccccttc cttcggagga ggagcactgc agcgtggtgg    19140
aggtgacaga ggaggaggtt aagaactcag tcaggctcat ccccagctgg accacggtgg    19200
taagagagcc ggggtagatg ctcccttgtc ctggagggcc tgggggacct gagccttgct    19260
ctgtgcctgg ctccttgggg ggacagaggc ctgcctggcc agccagctgt gatcctgggc     19320
cactggagcc gccattctgc tggaggccca tggagaggga ggtcttgtgg tcggagacc    19380 aggaggcttg gtgaggagag tgactgattt aaagaaatag cgggcgtggg gccgggcgcg   19440
gtggctcacg cctgtaatcc cagcactttg ggaggccaag gcgggcagat cacgaggtca     19500
ggagatcgag accatccttg aaaccccgac tctactaaaa atatagaaaa ttagctgggc    19560
gtggtggcgc gcgcgtgtag tcccagctac tcggaggct gaggcaggag aatggtgtga    19620
acccgggagg tggagtttgc cgtgagccga gatcgcgcca ctgcactcca gcctgggcca    19680
cagagcgaga ctgcgtctca aaaaaaaaa aagaagaaaa gaaagaaag aaataccggg     19740 cgcggtggct cacgcctgga atcccagcac tttgggaggc cgaggcgggt ggatcacgag    19800
```

```
gtcaggagat cgagaccatc ctggctaata cggcgaaacc ccacctctac taaaaataca   19860
aaaaaattag ccgggcgcag tggtgggcac ctgtagtccc agctactggg gaggccgagg   19920
caggagaatc gcttgaacct gggaggtgga ggttgtagtg agccaagatc acgccattgc   19980
actccagcct ggttgacaga acgagactcc atctcaaaaa aaaaagaaa gaaatagatg    20040
gcccttgctc agcggcagca gtcaccgtga ctggaagaag catttcattc cgtccagaca   20100
gttactgagc ttccgttctc caggcactgc acaaggtgcc gaggacaagg caggggaacg   20160
gcctgggcag cctttggatt ggaggagtgg ccccaaagcc cacgtatcag ttaggcggcg   20220
cctgcgtctc ccccagagcc cacgtatcag ttaggcagca cctgcgtctc ccccagagcc   20280
cacatatcag ttagacggcg cctgcttctc ccccagcgcc cacgtatcag ttagacggcg   20340
cctgcttctc ccccagagcc cacgtatcag ttagacggcg cctgcttctc ccccagatcc   20400
tgtgtatcag ttagactgcg cctgcttctc ccccagagcc cacgtatcag ttagacggcg   20460
cctgttactc ccccagagcc cacgtatcag ttagacggcg cttgcttctc ccccagatcc   20520
cgcgtatcag ttagacgggc ctgcgtctcc cccagatccc gcgtatcagt tagacgggcc   20580
tgcgtctccc ccagagccca cgtatcagtt agacgggcct gcgtctcccc cagagcccac   20640
gtatcagtta gacggcgcct gcttctcccc cagagcccac gtatcagtta gacgggcctg   20700
cgtctccccc agagcccacg tatcagttag acggcgcctg cttctccccc agagcccgcg   20760
tatcagttag acggtgcctg catctccccc gtgcccacgt atcagttaga cggcgcctgc   20820
ttctccccca gagcccacgt atcagttaga cgggcctgcg tctcccccag atcctgcgta   20880
tccattagac agtgcctgtg tctcccctag tgcccgctca catttcggtt ttgctcctct   20940
tcctctgctc agcttctgtg ttggcacttg gaaagtgatt cacatagtcc cccgtggcca   21000
cctggggcca ctgagagccc tgccctgccc ctgcctgaca gtcaagtgag tcaggcaag   21060
cacaaggcca ggaggagagc cagggccact gccgttggcg gggcctggcc ttgcacttta   21120
tccccctctg cagggtcccg gcccagctgg gaccagctgg ctcaatccct gcccctatg    21180
cttacttgac tctgtggggt cgctggaacc aggcaactcc cacggggtcc ccatgaccac   21240
ttgcctgatc ttagccacca tctcctctct ctcagaccac tggaacaacc tcccacgctg   21300
tcccttgctt ctactctcac tccctgtccc cctggtcaat gctcaactca gcacccagca   21360
tggtcccagt ggcatgagtg tgtcacctcc cagctcagag cctgcttctc actcgggctg   21420
ctgtgtccct cagaatcaga cctccagcct gtgcccacc acccgccctg tttttctgcg    21480
gggctcgtgc accgtcccgc catcatgcac tcgtctctgg ccacgtgcca tggaagggc    21540
tgcccccagag ccttcagact tcgcttccct ctgcccgggg agtcccaccc ccgatggcca   21600
cgggactcgc tccctcactt ccttcggctt tttacgccag ggtcccctcc tagagagaag   21660
cgagccttcc ctgaccctgt agcttcagcc tcccctgctt cacacctcat cgccattccc   21720
ttgtttatt tttccttc cacttactga catacataat ttactgatttt tcttcttta    21780
cttatcgcct gtctccccca actagaatat aagctgtatg atggctgggc gcagtggctc   21840
acgcctgtaa tcccagcact tgggaggcc aaggcggag gatcacttga ggtcaggagt     21900
ttgagaccag cctggccaac atgctgaagc ccgtctctt ctaaaaatac aaaaaattag    21960
ccgggtgtgg tggtggacgc ctgtaatccc agctattcag gagactgagg cggaaggatc   22020
atttgaagcg gggaggcaga ggttgcagtg agccgagatt gtgccactgc actccagccc   22080
tgggcaacaa gagcaaaact ccgtctgaaa aaaaaaagg ctatatgagg gcaggaattc    22140
tggcctcagt gtggccccag ggcctagagt agtggccagc acccagtagg cagccagtgg   22200
```

-continued

```
tgaccagtgt tgacgggatg gatggacaca agcgagggag tgaagggact ggcaagtgtg   22260
ccgctgcctc tctgcatgcg tgtgagtcgg cgtgtctgtg ggcacggcat ggaaccgtcc   22320
ttgtcacgga ggagggacaa aggcagagag ccaggctgcg gcagctgttc ccctcctggc   22380
agccccactg actgggccac cggctgcggc tcagccgctt cccggccgc cctgcagtag    22440 catcttggca tcttctcggc ggccggaagg cgggaaggat ggcacagcat ccctccatgg   22500
cattgctgcc gtagcgagaa ggtatcttct aatggactcc cacttccagc cctgccctc    22560 cccactcttt cagcctggcc ttgcggaccc ttcatgggct ggtcccggcc cctcctcat    22620 gtaccagtgg catccggctc ctcaccattc caggaatatg cccccagctg ccagcgcccc   22680
gtgttcttgc ctctgccatt tcatgctgtg ctgattgaga tgggacccgc actgcggccc   22740
ccttggcagc tgctctcggg gaatcggagc agaggctgcg tgtctgggag cctgggacct   22800
gtgctcctca cgctgccttg tcctcctcag atcctggtga agtccatgct gaggaagcgt   22860
tcctttggga acccgtttga gccccaagca cggagggaag agcgatccat gtctgctcca   22920
ggaaacctac tggtgtaagt actggtgggc caggactgc cgggcactcc ctggagttgg    22980
gtggggaggt ctgaggccca tcctcccact ctcactgtcg ttgggccaag gccagagcct   23040
ggggacttgg ccaggtctcg gtgttggccc catttgcatc tctgtcccca aggttagtcg   23100
gggctagaag ggacctttg ggcccagctc ttgcttcatt cctggggcca gcatccctca    23160
cacacacact tccagggatg aggagctcac gcagcccctc catgggacag aagaccctt    23220 cttccatgca gcttgatgtc actctctcac tgggtccagc ccctctgggg cttcaaatct   23280
gtggccccct cagcccttgg cagcctggca gaggtttgca gacaggctga tgttggcttc   23340
ctgtaggagg ctggcgggct gtagaggagg ggtgctggcc cctctgcctg gccctgggga   23400
ctgttggctg ctctcccaag tggcccaggc tgcctgcagc cattgctggg gctctgtgcc   23460
cagtcagcac tttgtgagtg cttgttcagt gagtaagcag ggacaggctg gccggtggac   23520
cacgggagag gaacccgcat tggccgaggg ctccctatgg tgagccacgc ctgtgggttc   23580
accacctcct aggagggtcc agaaaagcag ctccccaagc ctgtgcgcct cgtcctcagc   23640
agatccacct tcttcactat aataaaagcc agtctgggat gctaataagg cctgtgctgg   23700
agtttgtaca caaacctgca gagagaaaac cagtggggtc ctgaaccaca gcgtggtcct   23760
gggacagcca ctgccttcct ctggccccgg agggaagctt tggggaaggg gctggtggga   23820
gttgtttgcc ccaccctggc ctgctctgtg tggaaggcgc actccccaga ggggtgagtg   23880
ccaggcgctg tccgggtgcc ttggcttcac gctgtcacca ggcctgtccg ggaccaccat   23940
gttggtttcc cgtgaggcct ccctctcata agagggccct tcagaagggt cgggacccct   24000
cgtagtggac aagctgacat ctgctccctg ctggaggtgg cttgcaccca gggagagcct   24060
cataatgagg tgggggcct gggagaggcc tggaggtccc aactgcagct tttctgtcat    24120
ctcttcaggg aggtggttgc ggttggggga ggattctctg agctcatcca ggaatgtagg   24180 ccctgatgc tggaattgtg cttagtgtag ggggagaggg ggcatatata atttgacgtc    24240
caaatgggga cattttgag agtgaaaggg gaagccatta ataattatgc cagcacggcc    24300
gggtgcggtg gctcacgcct gtaatcccag cactttggga ggccgaggct ggtggatcac   24360
agggtcagga gatcgagacc atcctggcta acacggtgaa accccgtctc tactaaaaat   24420
acaaaaaatc agctgggcgt ggtggcgggc acctggagtc ccagctactc aggaggctga   24480
ggcaggagaa tggcgtgaac ccgggaggca gagcttgcag tgagccaagg tcacgccact   24540
```

```
gcactccagc ctgggcgaca gagtgagact ccgtctcaaa aataataat tattatgcca    24600 gcatggtggc tcatgcctat aatcccagca ctttgggagg ccaaggcagg attgcttgag    24660
gccaggagtt caagaccagc ctgggcaaca tagcaagacc ccatctctaa aaaaaaaaa    24720 aattagccgg gcgtggtggt gggtgcctgt agtcccagca actcaggagg ctgaggtggg    24780
aggattgctt gagtctggga ggtggaggtt gcagtgagct gagattgcac cactgtactc    24840
cagcctgggt gacagagcca gaccctgtct caaaaaaaaa aaagaaaaaa aagtaataat    24900
aattatgcca ggacagcagg tggacggaca cctggtcctt ctgactcaga gcctgtggtc    24960
cagcaccccc tagtggtgga acaagccaga cacaggataa ggatacattt agtgtctagt    25020
ttgtacctgg caaacagagt gacaagattg ggcttaatac tttccagcta taaaattcta    25080
gaattctgtg acccaagttt aatttggggt agagcttttt aaaaaaaaaa tagagatgga    25140
gtcttgccat gttgcccagg ctggacttaa actcctggcc tcaagccatt tgcccacctt    25200
ggcctccgaa agtgccaggt gattacaggc atgagccacc acacccagcc tccacgttta    25260
actttgaaag aagattttac ttcatcatca agtcccaata tttatccttg atagactgct    25320
ttggtttttt gtttgtttgt tttgagatgg agtttcactc ttgttgccca ggctggagtg    25380
cagtggcgca aactcaactc actgcagtct ccgcctctca cattcaagca gttctcttgc    25440
ctcagcctcc caagtagctg ggattacagg tgcatgccac caccacaccg ctaatttttt    25500
gtatttttat tagagacggg atttcaccat tttggccagg ctggtctcaa actcctgacc    25560
tcaggtaatc tgcccacctc agcctcccaa agtgctggga ttacaggcgt gagccactgt    25620
gcccggccat agagtttttt atactttggg ataattgtag aaactcagta gtagagttaa    25680
gtggagttgg tcctttttaa agatatcaaa acccatttac tggttatttt aaaaagagac    25740
attttgggag gaaaactaga tatagaaatc tgttgaatat gtgacagaat cccaagactg    25800
atagatggac tctgccctgt gaacaaggca agaaaaatg caaatgaaa gcctctctac    25860 ccagatctgc tgggggatga ctgaggtcaa cacagaaggc cctcaggccg gcacggtgg    25920 ctcacgcctg caatcccaac actttaggag gctgaggtgg atggatcgct tgagcccagg    25980
agtttgagac cagcctgggc aacatggtga accctgtttt ttatagagat aaaaaaatac    26040
aaaaattagc tgggcgtggt ggcatgtgcc tgtagtctca gctactcagg aggctgaggt    26100
gggaggatcg cttgagcctg aaggcagag gttgcaatga gctgagattg caccactgca    26160
ctgcagcctg cacgacagag cgagacgctg tctcaaaaca acaacaaaac cacacacaca    26220
gagagaaggc ccttgattag gctgatagtt ggaggatgta gggaagtcag ctgggtcaga    26280
ctgtgagcag ctccagaggc cgtgctggga ggtttagact tcatctctgg tcaatggggg    26340
gccacggagg cgttgcgggc tgagactggg ggctgagaga ccggcaagga gcaactgccg    26400
tgatgtaggg aggccagagg gaggccaagc ttggggcagt gggtgaaggg ggctttgaga    26460
gatgtgggat tcagattcct gtgtgtgtga gggagagtgt ctccctgagt gcatattctg    26520
accctgaggt ccctctgtcc ctggtgtccc ctgaacagga agaagggtt tggtgaaggg    26580 ggcaagagcc cagagctccc cggcgtccag gaagacgagg ctgcatcctg agcccctgca    26640
tgcacccagg gccacccggc agcacactca tcccgcgcct ccagaggccc accccctcat    26700
gcaacagccg ccccgcagg caggggctg gggactgcag ccccactccc gccctcccc    26760 catcgtgctg catgacctcc acgcacgcac gtccagggac agactggaat gtatgtcatt    26820 tgggtcttg gggcagggc tcccacgagg ccatcctcct cttcttggac ctccttggcc    26880
tgacccattc tgtggggaaa ccgggtgccc atggagcctc agaaatgcca cccggctggt    26940
```

```
tggcatggcc tggggcagga ggcagaggca ggagaccaag atggcaggtg gaggccaggc   27000
ttaccacaac ggaagagacc tcccgctggg gccgggcagg cctggctcag ctgccacagg   27060
catatggtgg agagggggt accctgccca ccttggggtg gtggcaccag agctcttgtc   27120
tattcagacg ctggtatggg ggctcggacc cctcactggg gacagggcca gtgttggaga   27180
attctgattc cttttttgtt gtcttttact tttgttttta acctgggggt tcggggagag   27240
gccctgcttg ggaacatctc acgagctttc ctacatcttc cgtggttccc agcacagccc   27300
aagattattt ggcagccaag tggatggaac taactttcct ggactgtgtt tcgcattcgg   27360
cgttatctgg aaagtggact gaacggaatc aagctctgag cagaggcctg aagcggaagc   27420
accacatcgt ccctgcccat ctcactctct cccttgatga tgcccctaga gctgaggctg   27480
gagaagacac cagggctgac tttgaccgag ggccatggac gcgacaggcc tgtggccctg   27540
cgcatgctga ataactgga acccagcctc tcctcctaca ccggcctacc catctgggcc   27600
caagagctgc actcacactc ctacaacgaa ggacaaactg tccaggtcgg agggatcacg   27660
agacacagaa cctggagggg tgtgcacgct ggcaggtggc ctctgcggca attgcctcac   27720
cctgaggaca tcagcagtca gcctgctcag agcgggggtg ctggagcgcg tgcagacaca   27780
gctcttccgg agcagcctttc accttctctc tgggatcagt gtccggctgg ccgacgtggc   27840
atttgctgac cgaatgctca tagaggttga ccccacagg gtcacgcagg actcggacac   27900
tgccctggaa acatggatgg acaagggctt ttggccacag gtgtgggtgt cctgttggag   27960
gagggcttgt ttggagaagg gaggctggct gggggagaaa cccggatccc gctgcatctc   28020
cgcgcctgtg ggtgcatgtc gcgtgctcat ctgttgcaca cagctcactc gtatgtcctg   28080
cactggtaca tgcatctgta atacagtttc tacgtctatt taaggctagg agccgaatgt   28140
gccccattgt cagtgggtcc acgtttctcc ccggctcctc tgggctaagg cagtgtggcc   28200
cgaagcttaa aaagttactc ggtactgttt ttaagaacac ttttatagag ttagtggaag   28260
gcaagttaag agccaatcac tgatccccaa gtgtttcttg agcatctggt ctgggggggac  28320 cactttgatc ggacccaccc ttggaaagct caggggtagg cccaggtggg atgctcaccc   28380
tgtcactgag ggttttggtt ggcatcgttg ttttttgaatg tagcacaagc gatgagcaaa   28440
ctctataaga gtgtttaaa aattaacttc ccaggaagtg agttaaaaac aataaaagcc   28500 cttcttgag ttaaaagaa aaaaaaaagg tttgtgcgta catttctgc atctggatat   28560 acgttctttc tcagcagctg gaacagctgg cttgttgaa ttttctggaa gcgtctgagg   28620
caccctaagt ccctgagcag gacagtggtg agaagtggtc ttggcggagg gagggagagg   28680
gaagggctgg ctcaggaggt gaccgggctg cagtccaggg tacagctgag gctcctgggc   28740
gggtccgtgg ccactccttg ggaagaactg cctgtttcac agggggctcag gatgccaagg   28800 tctggtccgg gtaggagcca tagctgctgc ttttgggggca gaggtccctg tggtgtcaca   28860
ggagtgcctg tgacaccagc ccagtgacct cccatccccg cttagccttg gacactggta   28920 cagactttg ggacccccaca cctctgttcc catggtacag ccctccagggg cagcgacgaa   28980 aagagtcatc cttaaggtca cacagccctg agcttgaatc caagctttgc tacttaaaaa   29040
ttgtgtgacc tttggcaggt cattggagga gcctcagttc ccttattgat ttaatgggaa   29100
tgttcccgtg gggtgttttg tttgtttgtt tgagattttt tgagacttgc tctgtcaccc   29160
aggctggagt gcaatggcaa gatctcggct cactgcaacc tcttcctcct gggttcaagc   29220
gattctcctg cctcagcctc ccaagtagct gggactacag gtgcccgcca ccatgcccca   29280
```

```
gctaattttt tgtactttta gtagagacgg ggtttcacca tgttggccag gctggtcttg    29340
aactcctgac ctcaggtgat ctgcccacct cggcctccca aagtgctggg attacaggcg    29400
tgagccaccg cgcccacctc cccatggggt ttgaatgcaa acaatgcaaa cgttttcgtc    29460
tgctctcaca ctacaacagt gaacacagaa gacttctgtg accggctggg cgcggtggct    29520
cacgcctgta atcccagcac tttgggaggc tgaggaaggc ggatcatgag gtcggagatc    29580
gagaccatcc tggctgacac ggtgaaaccc cgtctctact aaaaataca                29629
```

<210> SEQ ID NO 4
<211> LENGTH: 505
<212> TYPE: PRT
<213> ORGANISM: Rattus norvegicus

<400> SEQUENCE: 4

```
Met Glu Arg Ser Pro Ala Val Cys Cys Gln Asp Pro Arg Ala Glu Leu
 1               5                  10                  15

Val Glu Arg Val Ala Ala Ile Ser Val Ala His Leu Glu Glu Ala Glu
            20                  25                  30

Glu Gly Pro Glu Pro Ala Ser Asn Gly Val Asp Pro Pro Arg Ala
        35                  40                  45

Arg Ala Ala Ser Val Ile Pro Gly Ser Ala Ser Arg Pro Thr Pro Val
    50                  55                  60

Arg Pro Ser Leu Ser Ala Arg Lys Phe Ser Leu Gln Glu Arg Pro Ala
65                  70                  75                  80

Gly Ser Cys Leu Glu Ala Gln Val Gly Pro Tyr Ser Thr Gly Pro Ala
                85                  90                  95

Ser His Met Ser Pro Arg Ala Trp Arg Arg Pro Thr Ile Glu Ser His
            100                 105                 110

His Val Ala Ile Ser Asp Thr Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Arg Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Pro Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Pro Glu Glu Gln Ala Arg Leu Tyr Leu
                245                 250                 255

Arg Asp Ile Ile Leu Gly Leu Glu Tyr Leu His Cys Gln Lys Ile Val
            260                 265                 270

His Arg Asp Ile Lys Pro Ser Asn Leu Leu Gly Asp Asp Gly His
        275                 280                 285

Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
305                 310                 315                 320
```

```
Ala Ile Ser Asp Thr Gly Gln Ser Phe Ser Gly Lys Ala Leu Asp Val
            325                 330                 335

Trp Ala Thr Gly Val Thr Leu Tyr Cys Phe Val Tyr Gly Lys Cys Pro
            340                 345                 350

Phe Ile Asp Glu Tyr Ile Leu Ala Leu His Arg Lys Ile Lys Asn Glu
            355                 360                 365

Ala Val Val Phe Pro Glu Glu Pro Glu Val Ser Glu Glu Leu Lys Asp
    370                 375                 380

Leu Ile Leu Lys Met Leu Asp Lys Asn Pro Glu Thr Arg Ile Gly Val
385                 390                 395                 400

Ser Asp Ile Lys Leu His Pro Trp Val Thr Lys His Gly Glu Glu Pro
                405                 410                 415

Leu Pro Ser Glu Glu Glu His Cys Ser Val Val Glu Val Thr Glu Glu
                420                 425                 430

Glu Val Lys Asn Ser Val Lys Leu Ile Pro Ser Trp Thr Thr Val Ile
            435                 440                 445

Leu Val Lys Ser Met Leu Arg Lys Arg Ser Phe Gly Asn Pro Phe Glu
        450                 455                 460

Pro Gln Ala Arg Arg Glu Glu Arg Ser Met Ser Ala Pro Gly Asn Leu
465                 470                 475                 480

Leu Leu Lys Glu Gly Cys Gly Glu Gly Gly Lys Ser Pro Glu Leu Pro
                485                 490                 495

Gly Val Gln Glu Asp Glu Ala Ala Ser
            500                 505
```

ISOLATED HUMAN KINASE PROTEINS, NUCLEIC ACID MOLECULES ENCODING HUMAN KINASE PROTEINS, AND USES THEREOF

RELATED APPLICATIONS

The present application is a divisional of U.S. application Ser. No. 09/729,995, filed Dec. 6, 2000, issued on Jul. 30, 2002 as U.S. Pat. No. 6,426,206, which claims benefit of U.S. Provisional Application No. 60/247,031, filed Nov. 13, 2000 now abandoned.

FIELD OF THE INVENTION

The present invention is in the field of kinase proteins that are related to the calcium/calmodulin-dependent protein kinase kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Serine/Threonine Protein Kinases, including Calcium/Calmodulin-Dependent Protein Kinases Calcium/calmodulin (CaM) dependent protein kinases are members of the serine/threonine protein kinases (STK) family. Serine/threonine protein kinases add phosphate moiety to a serine or threonine residue of the substrate. Protein kinase substrates include elements of signal transduction pathways such as transcription factors or ion channels, as well as structural proteins such as filaments and cellular motors. The protein kinase gene family is one of the largest gene families in the genome. Classification of kinases are based on their sequence, tissue localization, and domain topology. Primary structures of kinases are rather conserved. A number of soluble and transmembrane proteins contain kinase domains along with other structural components; these multi-domain proteins also are often referred to as kinases. Tissue specific expression of kinases is often defined by transcription regulatory elements.

Calmodulin is a calcium receptor that mediates many calcium regulated processes by binding to target proteins in response to the binding of calcium. The principal target protein in these processes is CaM-dependent protein kinases (also referred to as CaM kinases). CaM-kinases are involved in regulating smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade" (Tokumitsu et al., *J. Biol. Chem.* 1995 270:19320–19324).

The kinase provided by the present invention shows a high degree of similarity to calmodulin-dependent kinase kinase, an enzyme that activates CaM-kinase IV. CaM-kinase IV is markedly activated upon phosphorylation by CaM-kinase IV kinase. CaM kinase IV, as well as its activating kinase, CaM kinase IV kinase, are the key elements of the calcium-dependent signal transduction cascade in neurons and lymphocytes.

Northern and Western blot analyses of CaM-kinase IV kinase showed relatively weak reactions in the rat cerebellum, where the activity of CaM-kinase IV kinase has been demonstrated to exist, indicating that CaM-kinase IV kinase isoforms distinct from the enzyme cloned from the cerebral cortex may exist in the cerebellum. Immunoprecipitation techniques have indicated that at least two distinct isoforms of CaM-kinase IV kinase exist in the brain (Okuno et al., *J. Biochem* (Tokyo) June 1996; 119(6):1176–81).

Furthermore, the CaM kinase cascade in myeloid cells may play a critical role in mediating the effects of calcium on neutrophil function and maturation. It has been found by Western analysis that CaM protein kinase kinase alpha (CaMKKalpha) is upregulated during retinoic acid induced neutrophil maturation. In addition, neutrophil progenitor cells express both CaMKI and CaMKIV transcripts; CaMKIV is downregulated during neutrophil maturation and CaMKI is expressed in uninduced cells and is induced by all-trans retinoic acid. (Lawson et al., *Exp Hematol* November 1999; 27(11):1682–90).

The gene provided by the present invention can be expressed in yeast to identify possible ligands or substrates of the kinase protein; this can be done by means of a complementation assay or a two-hybrid experiment. Artificially synthesized enzymes as well as derived peptides can be used to activate or inhibit cellular processes modulated by this kinase. Immunoassay or PCR may be used to measure the concentration of this protein and detect abnormally developing tissue or cancerous growth.

For a further review of calcium/calmodulin-dependent protein kinase kinases, see Park et al., *J .Biol Chem* Dec. 22, 1995;270(51):30464–9; Sakagami et al., *Brain Res Mol Brain Res* Mar. 1, 1998;54(2):311–5; and Enslen et al., *Biochem Biophys Res Commun* Feb. 27, 1995;207(3): 1038–43.

Kinase proteins, particularly members of the calcium/calmodulin-dependent protein kinase kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the calcium/calmodulin-dependent protein kinase kinase subfamily.

SUMMARY OF THE INVENTION

The present invention is based in part on the identification of amino acid sequences of human kinase peptides and proteins that are related to the calcium/calmodulin-dependent protein kinase kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in the eye (retinoblastomas) and brain.

DESCRIPTION OF THE FIGURE SHEETS

FIGS. 1A–1B provide the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the eye (retinoblastomas) and brain.

FIGS. 2A–2C provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3S provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 34 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the calcium/calmodulin-dependent protein kinase kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the calcium/calmodulin-dependent protein kinase kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the calcium/calmodulin-dependent protein kinase kinase subfamily and the expression pattern observed. Experimental data as provided in FIG. 1 indicates expression in humans in the eye (retinoblastomas) and brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known calcium/calmodulin-dependent protein kinase kinase family or subfamily of kinase proteins.

Specific Embodiments

Peptide Molecules

The present invention provides nucleic acid sequences that encode protein molecules that have been identified as being members of the kinase family of proteins and are related to the calcium/calmodulin-dependent protein kinase kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in the eye (retinoblastomas) and brain. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York; 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the gene encoding the novel human kinase protein of the present invention is positioned on public BAC AC005940, which is known to be located on human chromosome 17.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the gene encoding the novel human kinase protein of the present invention is positioned on public BAC AC005940, which is known to be located on human chromosome 17. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the novel human kinase protein of the present invention. SNPs were identified at 34 different nucleotide positions, including a non-synonymous cSNP at position 16135 and SNPs at two positions (2082 and 2748) 5' of the ORF that may affect control/regulatory elements. The change in the amino acid sequence caused by the G16135A SNP is indicated in FIG. 3 and can readily be determined using the universal genetic code and the protein sequence provided in FIG. 2 as a reference.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182:626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain. A large percentage of pharmaceutical agents are being developed that modulate the activity of kinase proteins, particularly members of the calcium/calmodulin-dependent protein kinase kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the eye (retinoblastomas) and brain. Such uses can readily be determined using the information provided herein, that which is known in the art, and routine experimentation.

The proteins of the present invention (including variants and fragments that may have been disclosed prior to the present invention) are useful for biological assays related to kinases that are related to members of the calcium/calmodulin-dependent protein kinase kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in the eye (retinoblastomas) and brain. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in the eye (retinoblastomas) and brain. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the eye (retinoblastomas) and brain. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254(1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the eye (retinoblastomas) and brain. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the eye (retinoblastomas) and brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the eye (retinoblastomas) and brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, iso-electric point, tryptic peptide digest, and other physical assays known to those in the art.

The antibodies are also useful for tissue typing. Experimental data as provided in FIG. 1 indicates expression in humans in the eye (retinoblastomas) and brain. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence).

Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the gene encoding the novel human kinase protein of the present invention is positioned on public BAC AC005940, which is known to be located on human chromosome 17.

FIG. 3 provides information on SNPs that have been found in the gene encoding the novel human kinase protein of the present invention. SNPs were identified at 34 different nucleotide positions, including a non-synonymous cSNP at position 16135 and SNPs at two positions (2082 and 2748) 5' of the ORF that may affect control/regulatory elements. The change in the amino acid sequence caused by the G16135A SNP is indicated in FIG. 3 and can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 34 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the gene encoding the novel human kinase protein of the present invention is positioned on public BAC AC005940, which is known to be located on human chromosome 17.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are-mediated by the kinase in cells and tissues that express it. Experimental data as provided in FIG. 1 indicates expression in humans in the eye (retinoblastomas) and brain. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in the eye (retinoblastomas) and brain.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the novel human kinase protein of the present invention. SNPs were identified at 34 different nucleotide positions, including a non-synonymous cSNP at position 16135 and SNPs at two positions (2082 and 2748)

5' of the ORF that may affect control/regulatory elements. The change in the amino acid sequence caused by the G16135A SNP is indicated in FIG. 3 and can readily be determined using the universal genetic code and the protein sequence provided in FIG. 2 as a reference. As indicated by the data presented in FIG. 3, the gene encoding the novel human kinase protein of the present invention is positioned on public BAC AC005940, which is known to be located on human chromosome 17. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the novel human kinase protein of the present invention. SNPs were identified at 34 different nucleotide positions, including a non-synonymous cSNP at position 16135 and SNPs at two positions (2082 and 2748) 5' of the ORF that may affect control/regulatory elements. The change in the amino acid sequence caused by the G16135A SNP is indicated in FIG. 3 and can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in the eye (retinoblastomas) and brain. Specifically, a virtual northern blot shows expression in retinoblastomas and PCR-based tissue screening panels indicate expression in the brain. For example, the kit can comprise reagents such as a labeled or labelable nucleic acid or agent capable of detecting kinase nucleic acid in a biological sample; means for determining the amount of kinase nucleic acid in the sample;

and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the novel human kinase protein of the present invention. SNPs were identified at 34 different nucleotide positions, including a non-synonymous cSNP at position 16135 and SNPs at two positions (2082 and 2748) 5' of the ORF that may affect control/regulatory elements. The change in the amino acid sequence caused by the G16135A SNP is indicated in FIG. 3 and can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1

(1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.
2. An isolated polypeptide having an amino acid sequence comprising SEQ ID NO:2.
3. A composition comprising the polypeptide of claim 1 and a carrier.
4. A composition comprising the polypeptide of claim 2 and a carrier.
5. The isolated polypeptide of claim 1, except that residue 375 of SEQ ID NO:2 is glycine.
6. The isolated polypeptide of claim 2, except that residue 375 of SEQ ID NO:2 is glycine.
7. A composition comprising the polypeptide of claim 5 and a carrier.
8. A composition comprising the polypeptide of claim 6 and a carrier.

* * * * *